(12) United States Patent
Kazmierczak et al.

(10) Patent No.: US 7,452,705 B2
(45) Date of Patent: Nov. 18, 2008

(54) N4 VIRION SINGLE-STRANDED DNA DEPENDENT RNA POLYMERASE

(75) Inventors: Krystyna M. Kazmierczak, Park Ridge, IL (US); Elena K. Davydova, Chicago, IL (US); Lucia B. Rothman-Denes, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 10/153,219

(22) Filed: May 22, 2002

(65) Prior Publication Data

US 2003/0096349 A1     May 22, 2003

Related U.S. Application Data

(60) Provisional application No. 60/292,845, filed on May 22, 2001.

(51) Int. Cl.
    *C12N 9/12*     (2006.01)
    *C12N 1/20*     (2006.01)
    *C12N 15/63*     (2006.01)
    *C07H 21/04*     (2006.01)

(52) U.S. Cl. .............. 435/194; 435/183; 435/252.3; 435/320.1; 435/6; 536/23.2

(58) Field of Classification Search ............ 435/194, 435/320.1, 252.3, 183, 8; 536/23.1, 23.2; 530/350
See application file for complete search history.

(56) References Cited

U.S. PATENT DOCUMENTS

| | | | |
|---|---|---|---|
| 5,700,667 A | 12/1997 | Marble et al. | 435/91.3 |
| 5,869,320 A | 2/1999 | Studier et al. | 435/252.33 |
| 5,981,247 A * | 11/1999 | Hagedorn et al. | 435/194 |
| 6,218,145 B1 | 4/2001 | Bogosian et al. | 435/69.1 |

FOREIGN PATENT DOCUMENTS

| | | |
|---|---|---|
| WO | WO 00/11160 | 3/2000 |
| WO | WO 01/75067 | 10/2001 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
GenEMBL Database Accession No. Z82091, Nov. 1996.*
Abravaya and Rothman-Denes, "N4 RNA polymerase II sites of transcription initiation," *J. Mol. Biol.*, 211:359-372, 1990.
Butler and Chamberlin, "Bacteriophage SP6-specific RNA polymerase. I. Isolation and characterization of the enzyme," *J. Biol. Chem.*, 257: 5772-5778, 1982.
Cermakian et al., "Sequences homologous to the yeast mitochondrial and bacteriophage T3 and T7 RNA polymerases are widespread throughout the eukaryotic lineage," *Nuc. Acids Res.*, 24:648-654, 1996.
Cheetham and Steitz, "Insights into transcription: structure and function of single-subunit DNA-dependent RNA polymerases," *Curr. Op. In Struc. Biol.*, 10:117-123, 2000.
Cramer et al., "Structural basis of transcription: RNA polymerase II at 2.8 Ångstrom resolution," *Science*, 292(5523):1863-1876, 2001.
Dai and Rothman-Denes, "Sequence and DNA structural determinants of N4 virion RNA polymerase-promoter recognition," *Genes Devepmnt.*, 12:2782-2790, 1998.
Delarue et al., "An attempt to unify the structure of polymerases," *Protein Engineering*, 3:461-467, 1990.
Falco and Rothman-Denes, "Bacteriophage N4-induced transcribing activities in *E. coli*: I. Detection and characterization in cell extracts," *Virology*, 95:454-465, 1979.
Falco and Rothman-Denes, "Bacteriophage N4-induced transcribing activities in *E. coli*: II. Association of the N4 transcriptional apparatus with the cytoplasmic memebrane," *Virology*, 95:466-475, 1979.
Falco et al., "Virion-associated RNA polymerase required for bacteriophage N4 development," *Proc. Natl. Acad.Sci. USA*, 74:520-523, 1977.
Falco et al., "DNA-dependent RNA polymerase from bacteriophage N4 varions: purification and characterization," *J. Biol. Chem.*, 255: 4339-4347, 1980.
Falco et al., "Novel template requirements of N4 virion RNA polymerase," *Proc. Natl. Acad. Sci. USA*, 75: 3220-3224, 1978.
Glucksmann et al., "Specific sequences and a hairpin structure in the template strand are required for N4 virion RNA polymerase-promoter recognition," *Cell*, 70:491-500, 1992.
Glucksmann-Kuis et al., "*E. coli* SSB activation of N4 virion RNA polymerase: specific stabilization of an essential DNA hairpin required for promoter recognition," *Cell*, 84:147-154, 1996.
Gross et al., "The functional and regulatory roles of sigma factors in transcription," In: *Mechanisms of Transcription*, Cold Spring Harbor *Symp. Quant. Biol.*, 63: 141-155, 1998.
Haynes and Rothman-Denes, "N4 virion RNA polymerase sites of transcription initiation," *Cell*, 41:597-605, 1985.
Hedtke et al., "Mitochondrial and chloroplast phage-type RNA polymerases in Arabidopsis," *Science*, 277:809-811, 1997.

(Continued)

*Primary Examiner*—Richard G Hutson
(74) *Attorney, Agent, or Firm*—Fulbright & Jaworski L.L.P.

(57) ABSTRACT

A histidine-tagged, deletion mutant of bacteriophage N4-coded, virion RNA polymerase (mini-vRNAP) which is active has been developed. The his-tagged mini-vRNAP has been cloned under the control of the pBAD promoter, is stable and is purified in a single step yielding large amounts (10 mg/liter of *E. coli* expressing cells). This RNA polymerase uses single-stranded DNA containing 17 bases (the promoter) upstream of the transcribed regions as a template. In the presence of *E. coli* SSB protein, it transcribes this template efficiently, providing a unique system to synthesize RNAs of the desired sequence using single-stranded DNA templates. The enzyme incorporates derivatized nucleoside triphosphates with high efficiency. A mutant of mini-vRNAP has been generated that incorporates deoxynucleoside triphosphates. In addition, the inventors have developed an in vivo system to express RNAs and proteins under mini vRNA polymerase promoter control.

27 Claims, 17 Drawing Sheets

OTHER PUBLICATIONS

Hochschild and Dove,"Protein-protein contacts that activate and repress prokaryotic transcription," *Cell*, 92:597-600, 1998.

Malone et al., "Cloning and generation of a genetic map of bacteriophage N4 DNA," *Virology*, 162: 328-336, 1988.

Markiewicz et al., "*E. coli* single-stranded DNA binding (SSB) protein is a supercoiled-template dependent transcriptional activator of N4 virion RNA polymerase," *Genes and Dev.*, 6:2010-2019, 1992.

Miller et al., "RNA polymerase β' subunit: a target of DNA binding-independent activation," *Science*, 275:1655-1657, 1997.

Zivin and Zehring, "Transcriptional map of bacteriophage N4: location and polarity of N4 RNAs," *J. Mol. Biol.*, 152:335-356, 1981.

Dai et al., "Supercoil-induced extrusion of a regulatory DNA hairpin.," *Proc. Natl. Acad. Sci. USA*, 94:2174-2179, 1997.

Kazmierczak et al., "The phage N4 virion RNA polymerase catalytic domain is related to single-subunit RNA polymerases," *EMBO Journal*, 21:5815-5823, 2002.

Database Accession No. ABG11811.

\* cited by examiner

Bacteriophage N4 vRNAP promoters

Effect of Eco SSB on transcription of vRNAP and mini-RNAP

Binding affinities of stem-length promoter mutants

US 7,452,705 B2

N4 VIRION SINGLE-STRANDED DNA DEPENDENT RNA POLYMERASE

This application claims the priority of U.S. Provisional Patent Application Serial No. 60/292,845, filed May 22, 2001, the entire disclosure of which is specifically incorporated herein by reference.

The government may own rights in the present invention pursuant to grant number R01 A1 12575 from the National Institute of Health.

BACKGROUND OF THE INVENTION

I. Field of the Invention

The present invention relates generally to an RNA polymerase. More particularly, it provides a bacteriophage N4 virion RNA polymerase for synthesis of RNAs of desired sequences using single-stranded DNA templates.

II. Description of Related Art

The expression of a protein-encoding gene in a host cell involves transcription of messenger RNA (mRNA) from DNA by an RNA polymerase enzyme. Subsequently the mRNA is processed, involving recognition of a region of the 3' UTR and addition of a tail of polyadenylate nucleotides to the 3' end of the mRNA by polyadenylation enzymes. After transcription, the mRNA encounters ribosomes which associate with a region of the 5' UTR of the mRNA and translocate in a 3'-ward direction along the mRNA. During translocation, amino acids are added to one another in sequence to form the polypeptide product of the protein-encoding gene. For prokaryotic transcription-translation, the Shine-Dalgarno sequence of the bacterial mRNA located about six to nine nucleotides before the initiation site for translation may be used for ribosome loading. This sequence is complementary to a sequence on the 3' end of the 16S rRNA and stimulates ribosome binding to the mRNA. The base pairing between the Shine-Dalgarno sequence and the mRNA sequences serves to align the initiating AUG for decoding.

Transcription of DNA into mRNA is regulated by the promoter region of the DNA. The promoter region contains a sequence of bases that signals RNA polymerase to associate with the DNA, and to initiate the transcription of mRNA using one of the DNA strands as a template to make a corresponding complementary strand of RNA. RNA polymerases from different species typically recognize promoter regions comprised of different sequences. In order to express a protein-encoding gene in a host cell, either the promoter driving transcription of the protein-encoding gene must be recognized by a host RNA polymerase, or an RNA polymerase which recognizes the promoter driving transcription of the protein-encoding gene must be provided to the host cell (U.S. Pat. No. 6,218,145).

Most DNA-dependent RNA polymerases read double-stranded DNA, limiting RNA synthesis to systems in which a double-stranded DNA template is available. The synthesis of RNA using single-stranded DNA is not as common. Synthesizing RNA using a single-stranded DNA template immobilized on a solid support is described in U.S. Pat. No. 5,700,667.

Therefore, this invention provides an RNA polymerase that reads single-stranded DNA. Also provided is an RNA polymerase for which the promoter sequence is present upstream of the transcription initiation site and therefore is not transcribed by the polymerase.

SUMMARY OF THE INVENTION

The invention provides a novel N4 virion RNA polymerase (vRNAP) and a mini-vRNA polymerase and method of use thereof. The novel polymerases are described by an isolated nucleic acid comprising a region encoding a polypeptide having the amino sequence set forth in SEQ ID NO:2, SEQ ID NO:4, SEQ ID NO:6, SEQ ID NO:8 or SEQ ID NO:15. The nucleic acid may comprise the nucleic acid sequence of SEQ ID NO:1, SEQ ID NO:3, SEQ ID NO:5, SEQ ID NO:7 or SEQ ID NO:14. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID NO:16 or SEQ ID NO:28 is preferred.

An aspect of the current invention comprises a recombinant host cell comprising a DNA segment encoding a N4 virion RNA polymerase. The DNA segment is either single- or double-stranded and the polypeptide encoded by the DNA segment is preferably SEQ ID NO:4 or SEQ ID NO:6. The recombinant host cell may be an *E. coli* cell. Another aspect of the current invention comprises a recombinant vector comprising a DNA segment encoding a N4 virion RNA polymerase polypeptide under the control of a promoter.

Yet another aspect of the current invention comprises an isolated polynucleotide comprising a sequence identical or complementary to at least 14 contiguous nucleotides of SEQ ID NO:1. The polynucleotide may comprise at least 20, 25, 30, 35, 40, 45, 50, 60, 75, 100, 150, 200, 250, 300, 400, 600, 800, 1000, 2000, 3000, 3300 or more contiguous nucleotides of SEQ ID NO:1. The polynucleotide may comprise all contiguous nucleotides of SEQ ID NO:3 or all contiguous nucleotides of SEQ ID NO:1. Similarly, the polynucleotide may comprise at least 20, 25, 30, 35, 40, 45, 50, 60, 75, 100, 150, 200, 250, 300, 400, 600, 800, 1000, 2000, 3000, 3300 or more nucleotides complementary to at least 20, 25, 30, 35, 40, 45, 50, 60, 75, 100, 150, 200, 250, 300, 400, 600, 800, 1000, 2000, 3000, 3300 or more contiguous nucleotides of SEQ ID NO:1.

Another aspect of the current invention comprises a purified N4 virion RNA polymerase comprising at least 20 contiguous amino acids of SEQ ID NO:2. It is preferred that the polymerase contain at least 25, 30, 35, 40, 45, 50, 60, 75, 100, 150, 200, 250, 300, 400, 600, 800, 1000 or more contiguous amino acids of SEQ ID NO:2.

Yet another aspect of the current invention comprises an isolated nucleic acid comprising a region encoding a polypeptide comprising at least 6 contiguous amino acids of SEQ ID NO:2, wherein the polypeptide has RNA polymerase activity under appropriate reaction conditions. It is preferred that this polypeptide comprises at least 10, 15, 20, 25, 30, 35, 40, 45, 50, 60, 75, 100, 150, 200, 250, 300, 400, 600, 800, 1000 or more contiguous amino acids of SEQ ID NO:2, SEQ ID NO:4, SEQ ID NO:6, SEQ ID NO:8, or SEQ ID NO:15. The encoded polypeptide may have at least one hexahistidine tag or other tag. The polypeptide may be a mutant of the peptide found in SEQ ID NO:2 or SEQ ID NO:4, such as an enzyme possessing an amino acid substitution at position Y678.

An embodiment of the current invention comprises a method of making RNA. This method comprises: (a) obtaining a N4 virion RNA polymerase (i.e. the polypeptide); (b) obtaining DNA wherein the DNA preferably contains a N4 virion RNA polymerase promoter sequence; (c) admixing the RNA polymerase and the DNA; and (d) culturing the RNA polymerase and the DNA under conditions effective to allow RNA synthesis. Optionally, the method may comprise synthesizing polynucleotides containing modified ribonucleotides or deoxyribonucleotides. The DNA is preferably single-stranded DNA or denatured double-stranded DNA Step (c) may occur in a host cell such as an *E. coli* host cell.

The amino acid sequence of the RNA polymerase is preferably the sequence essentially as set forth in SEQ ID NO:2, SEQ ID NO:4, SEQ ID NO:6, SEQ ID NO:8, SEQ ID NO:15, or a mutant form of the polymerase of SEQ ID NO:4 or SEQ ID NO:6. The mutation may be, for example, at position number Y678. The RNA transcript may contain derivatized nucleotides.

An aspect of the current invention comprises using an N4 vRNAP promoter to direct transcription. The promoter is preferentially an N4 promoter set forth in SEQ ID NO:16, SEQ ID NO:19, SEQ ID NO:20, SEQ ID NO:27, SEQ ID NO:28 or SEQ ID NO:29. The P2 promoter of SEQ ID NO:16 or SEQ ID NO:28 is preferred. The promoter sequence may be upstream of the transcription initiation site. The promoter may comprise a set of inverted repeats forming a hairpin with a 2-7 base pair long stem and 3-5 base loop having purines in the central and/or next to the central position of the loop.

The preferred conditions of the transcription method claimed herein includes a pH in step (c) of between 6 and 9, with a pH of between 7.5 and 8.5 more preferred. $Mg^{+2}$ or $Mn^{+2}$, preferably $Mg^{+2}$ may be admixed. Preferred temperatures for the reaction are 25° C. to 50° C. with the range of 30° C. to 45° C. being more preferred and the range of 32° C. to 42° C. being most preferred. The admixing may occur in vivo or in vitro.

An aspect of the current invention also includes translation of the RNA after transcription. A reporter gene such as an α-peptide of β-galactosidase may be used. It is preferred the transcription comprises admixing an *E. coli* single-stranded binding protein (EcoSSB), a SSB protein homologous to EcoSSB or another naturally occurring or chimeric SSB protein homologous to EcoSSB with the polymerase and DNA.

The DNA admixed with the RNA polymerase of the current invention may be single-stranded linear DNA or single-stranded circular DNA such as bacteriophage M13 DNA. The DNA may be denatured DNA, such as single-stranded, double-stranded linear or double-stranded circular denatured DNA. The DNA may also be double-stranded DNA under certain conditions. The RNA may be pure RNA or may contain modified nucleotides. Mixed RNA-DNA oligonucleotides may also be synthesized with the Y678F mutant mini-vRNAP (SEQ ID NO:8) of the current invention.

Yet another aspect of the current invention is the transcription method in which no EcoSSB is admixed with the RNA polymerase and DNA; the product of this method is a DNA/RNA hybrid.

The synthesized RNA may comprise a detectable label such as a fluorescent tag, biotin, digoxigenin, 2'-fluoro nucleoside triphosphate, or a radiolabel such as a $^{35}S$- or $^{32}P$-label. The synthesized RNA may be adapted for use as a probe for blotting experiments or in-situ hybridization. Nucleoside triphosphates (NTPs) or derivatized NTPs may be incorporated into the RNA, and may optionally have a detectable label. Deoxynucleoside triphosphates may be incorporated into the RNA.

The RNA may be adapted for use for NMR structural determination. Short RNAs such as those between 10 and 1000 bases or between 10 and 300 bases may be used. The RNA may be adapted for use in spliceosome assembly, splicing reactions or antisense experiments. Also, the RNA may be adapted for use in probing for a complementary nucleotide sequence or for use as a probe in RNase protection studies.

Yet another aspect of the current invention comprises delivering RNA into a cell after transcription of the RNA. The delivery may be by microinjection. Another aspect of the invention comprises amplifying the RNA after transcription.

Another embodiment of the current invention comprises a method of making RNA comprising: (a) obtaining a N4 virion RNA polymerase; (b) obtaining a single-stranded DNA oligonucleotide wherein the oligonucleotide contains a N4 virion RNA polymerase promoter sequence; (c) admixing the RNA polymerase and the oligonucleotide; and (d) culturing the RNA polymerase and the oligonucleotide under conditions effective to allow RNA synthesis. The polymerase preferentially has the amino sequence set forth in SEQ ID NO:4, SEQ ID NO:6 or SEQ ID NO:8. In this embodiment, it is preferred that the DNA has between 20 and 200 bases.

Yet another embodiment of the invention comprises a method of making RNA comprising: (a) obtaining a N4 virion RNA polymerase; (b) obtaining a single-stranded DNA wherein the DNA contains a N4 virion RNA polymerase promoter sequence; (c) obtaining a ribonucleoside triphosphate (XTP) or a derivatized ribonucleoside triphosphate; (d) admixing the RNA polymerase, the DNA and the XTP; and (e) culturing the RNA polymerase and the oligonucleotide under conditions effective to allow RNA synthesis wherein the RNA is a derivatized RNA. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8.

Another embodiment of the invention comprises a method for in vivo or in vitro protein synthesis comprising: (a) obtaining an RNA polymerase having the amino sequence set forth in SEQ ID NO:4, SEQ ID NO:6 or a mutant thereof; (b) obtaining DNA wherein the DNA contains a N4 virion RNA polymerase promoter sequence; (c) admixing the RNA polymerase and the DNA; (d) culturing the RNA polymerase and the DNA under conditions effective to allow RNA synthesis; and (e) culturing the RNA in vivo or in vitro under conditions effective to allow protein synthesis. Step (e) may comprise using a two plasmid system or a one plasmid system in which a reporter gene and the RNA polymerase gene are located on the same plasmid.

Yet another embodiment of the invention comprises a method of making a N4 mini-vRNAP comprising: (a) expressing vRNAP, wherein the vRNAP has the amino sequence set forth in SEQ ID NO:2, SEQ ID NO:4, SEQ ID NO:6, SEQ ID NO:8, SEQ ID NO:15 or a mutant thereof; and (b) purifying the vRNAP. The expression of vRNAP may occur in a bacteria, yeast, CHO, Cos, HeLa, NIH3T3, Jurkat, 293, Saos, or a PC12 host cell. A promoter such as pBAD may be used for making the vRNAP in bacterial cells. Any other promoter appropriate to the host cell line used can be employed when expressing vRNAP in other host cells. The polymerase may have a specific recombinant sequence that can be used in purification of the polymerase. The vRNAP may have at least one hexahistidine, FLAG, hemaglutinin or c-myc tag, or may not have a tag.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Bacteriophage N4 vRNAP promoters on single-stranded templates. These promoters are characterized by conserved sequences and a 5 bp stem, 3 base loop hairpin structure.

FIG. 2A shows a schematic of the N4 vRNAP protein with three motifs: the T/DxxGR motif found in DNA-dependent polymerases, the P-loop, an ATP/GTP-binding motif present in some nucleotide-binding proteins, and motif B ($Rx_3Kx_{6-7}YG$), one of three motifs common to the Pol I and Pol α DNA polymerases and the T7-like RNA polymerases (SEQ ID NOS: 39 and 40). FIG. 2B shows the mini-vRNAP.

FIG. 3A, SDS-PAGE analysis of the products of vRNAP digestion with trypsin. FIG. 3B N-terminal sequencing of the three initial proteolytic fragments indicated that the stable active polypeptide (mini-vRNAP) corresponds to the middle ⅓ of vRNAP, the region containing the three motifs described in FIG. 2A.

DESCRIPTION OF ILLUSTRATIVE EMBODIMENTS

Figure 2:
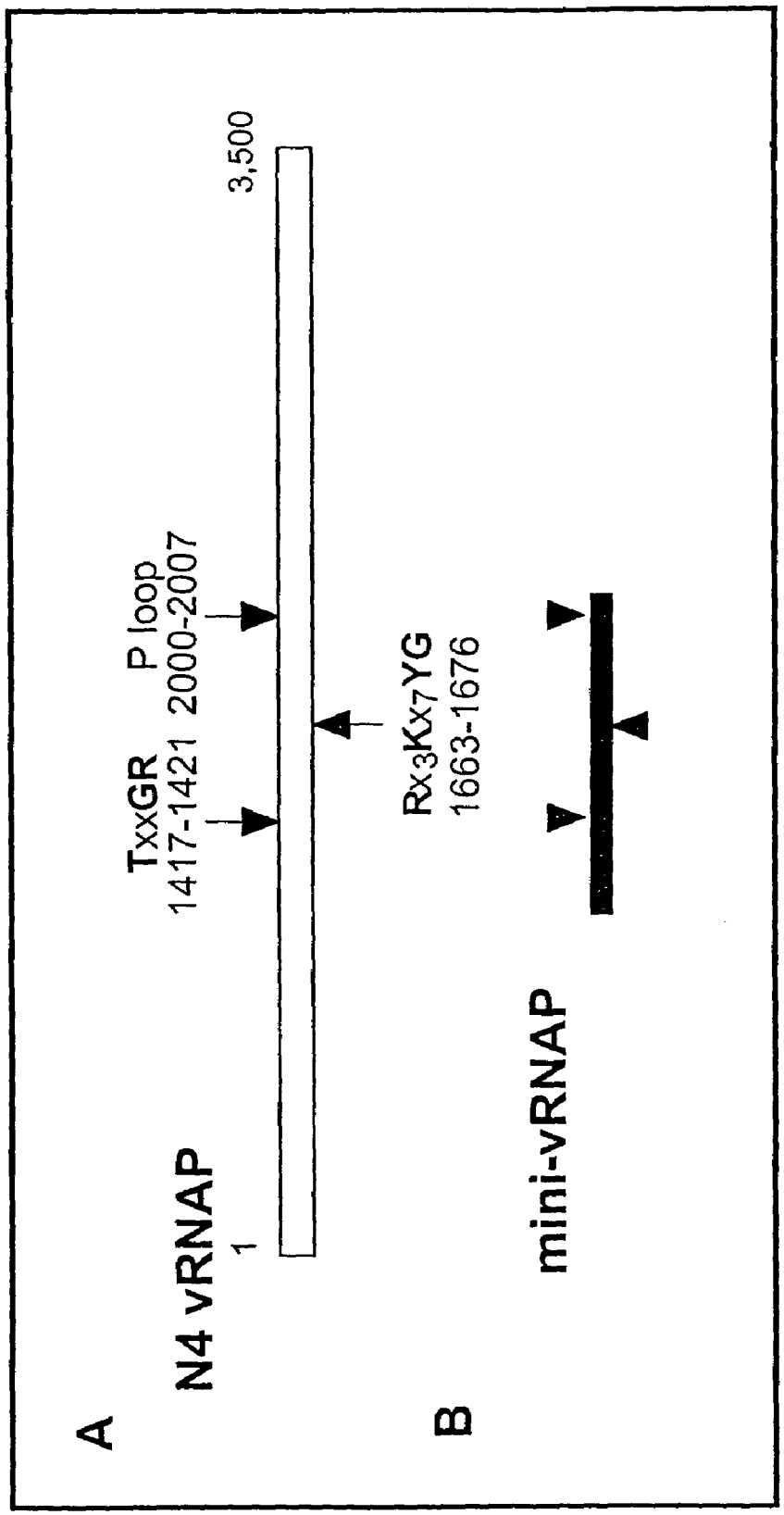
FIG. 2A and FIG. 2B—N4 vRNAP and generation of mini-vRNAP.

The present invention overcomes deficiencies in the art by providing a stable RNA polymerase that uses single-stranded DNA and provides a unique system to synthesize RNAs of a desired sequence. The RNA polymerase and mini-vRNA polymerase can be used to synthesize RNA for use as probes in RNase protection studies of DNAs or RNAs, in situ hybridization studies, and in Southern and Northern blot analysis, for the synthesis of defined RNA:DNA hybrids, for NMR structure determination of RNAs, for in vitro studies of spliceosome assembly, splicing reactions and antisense experiments, for in vitro translation or microinjection, and for nucleic acid amplification. The present invention allows for the synthesis of derivatized RNA and can use ssDNA in the form of single-stranded oligonucleotides, denatured DNA or DNA cloned into M13 templates.

I. RNA Polymerases a. Structure and Promoter Recognition of DNA-Dependent RNA Polymerases Inspection of the sequences of phage, archaebacterial, eubacterial, eukaryotic and viral DNA-dependent RNA polymerases has revealed the existence of two enzyme families. The eubacterial, eukaryotic, archaebacterial, chloroplast and the vaccinia virus RNA polymerases are complex multisubunit enzymes (5-14 subunits) composed of two large subunits, one to several subunits of intermediate molecular weight (30-50-kDa) and none to several subunits of small molecular weight (<30-kDa) (Archambault, et al., 1993; Record, et al., 1995). Eubacterial RNA polymerases are the simplest with an $\alpha_2\beta\beta'$ core structure. Sequence comparison of the genes coding for the different subunits of these enzymes has revealed: 1-sequence homology in eight segments (A to H) between $\beta'$ and the largest subunit of other RNA polymerases, 2-sequence homology in nine segments (A to I) between $\beta$ and the next largest subunit of other RNA polymerases, 3-sequence homology in 3 segments (1.1, 1.2 and 2) between $\alpha$ and a subunit in RNA polymerases I, II and III (Puhler, et al., 1989; Sweetser, et al., 1987). Not surprisingly, the crystal structures of yeast RNAP II and E. coli RNAP core revealed remarkable similarities (Zhang, et al., 1999; Cramer, et al., 2001).

In contrast, members of the phage T7-like (T3, SP6) family of RNA polymerases consist of a single (~100 kDa) polypeptide which catalyzes all functions required for accurate transcription (Cheetham, et al., 2000). The heterodimeric bacteriophage N4 RNAP II, nuclear-coded mitochondrial, and Arabidopsis chloroplast RNA polymerases show sequence similarity to the phage RNA polymerases (Cermakian, et al., 1996; Hedtke, et al., 1997; Zehring, et al., 1983). Three sequence motifs -A and C, which contain the two aspartic acids required for catalysis, and motif B- are conserved in polymerases that use DNA as a template (Delarue, et al., 1990). The crystal structure of T7 RNAP resembles a "cupped right hand" with "palm," "fingers" and "thumb" subdomains (Sousa, et al., 1993). The two catalytic aspartates are present in the "palm" of the structure. This structure is shared by the polymerase domains of E. coli DNA polymerase I and HIV reverse transcriptase (Sousa, 1996). Genetic, biochemical and structural information indicates that T7 RNA polymerase contains additional structures dedicated to nascent RNA binding, promoter recognition, dsDNA unwinding and RNA:DNA hybrid unwinding (Cheetham, et al., 2000; Sousa, 1996)

Both Class I and Class II RNA polymerases recognize specific sequences, called promoters, on B form double-stranded DNA. Eubacterial promoters (except those recognized by $\sigma^{54}$) are characterized by two regions of sequence homology: the -10 and the -35 hexamers (Gross, et al., 1998). Specificity of promoter recognition is conferred to the core enzyme by the $\sigma$ subunit, which makes specific interactions with the -10 and -35 sequences through two distinct DNA binding domains (Gross, et al., 1998). This modular promoter structure is also present at the promoters for eukaryotic RNA polymerases I, II and III. Transcription factors TFIIIA and TFIIIC direct recognition of RNAP III to two separate sequences (boxes A and C, separated by defined spacing) at the 5S gene promoter, while transcription factors TFIIIB and TFIIIC direct recognition of this enzyme to blocks A and B, separated by variable distance (31-74 bp) at the tRNA promoters (Paule, et al., 2000). Sequences important for RNAP I transcription initiation at the human rRNA promoters are also restricted to two regions: the "core" region located at -40 to +1 and the "upstream" region present at -160 to -107 (Paule, et al., 2000). Assembly of the initiation complex at RNAP II promoters requires several general transcription factors (TFIIA, TFIIB, TFIID, TFIIE, TFIIF and TFIIH). Recognition involves three core elements: the TATA box located at position -30 and recognized by TBP, the initiator element located near -1, and the downstream promoter element near +30 (Roeder, 1996).

Promoters for the T7-like and mitochondrial RNAPases are simpler. The T7-type RNAP promoters span a continuous highly conserved 23 bp region extending from position -17 to +6 relative to the start site of transcription (+1) (Rong, et al., 1998). The yeast mitochondrial RNAP promoters are even smaller, extending from -8 to +1 (Shadel, et al., 1993). One exception are the promoters for N4 RNAP II, which are restricted to two blocks of conserved sequence: a/tTTTA at +1 and AAGACCTG present 18-26 bp upstream of +1 (Abravaya, et al., 1990).

The activity of the multisubunit class of RNA polymerases is enhanced by activators at weak promoters. Transcription activators generally bind at specific sites on double-stranded DNA upstream of the -35 region (with the exception of the T4 sliding clamp activator), or at large distances in the cases of enhancers (Sanders, et al., 1997). Activators modulate transcription by increasing the binding (formation of closed complex) or isomerization (formation of open complex) steps of transcription through interactions with the $\alpha$ or $\sigma$ subunits of RNAP (Hochschild, et al., 1998). An exception is N4SSB, the activator of E. coli RNAP$\sigma^{70}$ at the bacteriophage N4 late promoters, which activates transcription through direct interactions with the $\beta'$ subunit of RNAP in the absence of DNA binding (Miller, et al., 1997).

Proteins that bind to ssDNAs with high affinity but without sequence specificity have been purified and characterized from several prokaryotes, eukaryotes, and their viruses (Chase, et al., 1986). These proteins (SSBs), which are required for replication, recombination and repair, bind stoichiometrically and, in many cases, cooperatively to ssDNA to cover the transient single-stranded regions of DNA that normally arise in vivo as a result of replication, repair and recombination. Binding to DNA results in the removal of hairpin structures found on ssDNA, providing an extended conformation for proteins involved in DNA metabolism. Several lines of evidence suggest that single-stranded DNA binding proteins play a more dynamic role in cellular processes. Genetic and biochemical evidence indicates that these proteins are involved in a multitude of protein-protein interactions including transcription activation (Rothman-Denes, et al., 1999).

b. The Bacteriophage N4 Virion RNA Polymerase

Bacteriophage N4 virion RNA polymerase (N4 vRNAP) is present in N4 virions and is injected into the *E. coli* cell at the beginning of infection, where it is responsible for transcription of the N4 early genes (Falco, et al., 1977; Falco, et al., 1979; Malone, et al, 1988). The N4 vRNAP gene maps to the late region of the N4 genome (Zivin, et al., 1981). N4 vRNAP purified from virions is composed of a single polypeptide with an apparent molecular mass of approximately 320,000 kDa (Falco, et al., 1980). In contrast to other DNA-dependent RNAPases, N4 vRNAP recognizes promoters on single-stranded templates (Falco, et al., 1978). These promoters are characterized by conserved sequences and a 5 bp stem, 3 base loop hairpin structure (FIG. 1) (Haynes, et al., 1985; Glucksmann, et al., 1992). In vivo, *E. coli* gyrase and single-stranded binding protein are required for transcription by N4 vRNAP (Falco, et al., 1980; Markiewicz, et al., 1992).

Sequencing of the N4 vRNAP gene revealed an ORF coding for a protein 3,500 amino acids in length (SEQ ID NO:1-2). Inspection of the sequence revealed no extensive homology to either the multisubunit or the T7-like families of RNA polymerases. However, three motifs are present (FIG. 2A): the T/DxxGR motif found in DNA-dependent polymerases, and Motif B ($Rx_3Kx_{6-7}YG$), one of three motifs common to the Pol I and Pol α DNA polymerases and the T7-like RNA polymerases.

c. Transcription Using N4 vRNAP

RNA synthesis requires RNA polymerase, a DNA template, an activated precursor (the ribonucleoside triphosphates ATP, GTP, UTP and CTP (XTP)), and divalent metal ions such as $Mg^{2+}$ or $Mn^{2+}$. The metal ion $Mg^{2+}$ is strongly preferred. Synthesis of RNA begins at the promoter site on the DNA. This site contains a sequence which the RNA polymerase recognizes and binds. The RNA synthesis proceeds until a termination site is reached. N4 vRNAP termination signals comprise a hairpin loop that forms in the newly synthesized RNA which is followed by a string of uracils (poly U). The sequence of the terminator signals for vRNAP present in the N4 genome include SEQ ID NOS:21-26. These N4 vRNAP termination signals possess all of the characteristics of eubacterial sequence-dependent terminators.

The ribonucleoside triphosphate may be derivatized with, for example, biotin. Derivatized XTPs can be used for the preparation of derivatized RNA. Exemplary methods for making derivatized XTPs are disclosed in detail in Rashtchian et al. (1992), herein incorporated by reference.

Single-stranded DNA of varying lengths can be used as a template for RNA synthesis using the N4 vRNAP or mini-vRNAP. Oligonucleotides and polynucleotides of intermediate length may be used. One particular single-stranded DNA that may be used is M13 DNA. M13 genomic DNA exists temporarily inside infected *E. coli* cells as a double-stranded DNA plasmid and is packaged as a small, single-stranded circular DNA into phage particles. M13 phage particles are secreted by an infected cell and single-stranded DNA can be purified from these particles for use as a transcription template. Initially M13 phage vectors required a working knowledge of phage biology and were primarily used for creating single-strand DNA molecules for DNA sequencing. M13-derived cloning vectors called "phagemids" take advantage of M13 replication to produce single-strand molecules, but can be propagated as conventional ColE1-based replicating double-strand plasmids.

EcoSSB is essential for N4 vRNAP transcription in vivo (Falco et al., 1978; Glucksmann, et al., 1992, herein incorporated by reference). EcoSSB is a specific activator of N4 vRNAP on single-stranded and supercoiled double-stranded DNA templates. EcoSSB, unlike other SSBs, does not melt the N4 vRNAP promoter hairpin structure (Glucksmann-Kuis, et al., 1996). EcoSSB has a high specificity for N4 vRNAP and mini-vRNAP resulting from EcoSSB's ability to stabilize the template-strand hairpin, whereas the nontemplate strand hairpin is destabilized. Other single-stranded DNA binding proteins destabilize the template-strand hairpin (Glucksmann-Kuis et al., 1996; Dai et al., 1998). When EcoSSB is not used in N4 vRNAP transcription in vitro, a DNA:RNA hybrid is formed, preventing template reutilization.

II. Genes and DNA Segments

Important aspects of the present invention concern isolated DNA segments and recombinant vectors encoding N4 vRNAP or more particularly mini-vRNAP or a mutant of mini-vRNAP and the creation and use of recombinant host cells through the application of DNA technology, that express a wild type, polymorphic or mutant vRNAP. Other aspects of the present invention concern isolated nucleic acid segments and recombinant vectors encoding vRNAP. Sequences of SEQ ID NO:1, 3, 5, 7, 14 and biologically functional equivalents thereof are used in the current invention. Single-stranded DNA oligonucleotides and polynucleotides can be used as DNA templates.

The present invention concerns isolated nucleic acid segments that are capable of expressing a protein, polypeptide or peptide that has RNA polymerase activity. As used herein, the term "nucleic acid segment" refers to a nucleic acid molecule that has been isolated free of total genomic DNA of a particular species. Therefore, a nucleic acid segment encoding vRNAP refers to a nucleic acid segment that contains wild-type, polymorphic or mutant vRNAP coding sequences yet is isolated away from, or purified free from, total bacterial or N4 phage genomic DNA. Included within the term "nucleic acid segment," are nucleic acid segments and smaller fragments of such segments, and also recombinant vectors, including, for example, plasmids, cosmids, phage, viruses, and the like.

Similarly, a nucleic acid segment comprising an isolated or purified vRNAP gene refers to a nucleic acid segment including vRNAP protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those of skill in the art, this functional term includes both genomic sequences, cDNA sequences and engineered segments that express, or may be adapted to express, proteins, polypeptides, domains, peptides, vRNAPs and mutants of vRNAP encoding sequences.

"Isolated substantially away from other coding sequences" means that the gene of interest, in this case the vRNAP, or more particularly mini-vRNAP genes, forms the significant part of the coding region of the nucleic acid segment, and that the nucleic acid segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

The term "a sequence essentially as set forth in SEQ ID NO:2 means, for example, that the sequence substantially corresponds to a portion of SEQ ID NO:2 and has relatively few amino acids that are not identical to, or a biologically functional equivalent of, the amino acids of SEQ ID NO:2.

This applies with respect to all peptide and protein sequences herein, such as those of SEQ ID NO:4, 6, 8 and 15.

The term "biologically functional equivalent" is well understood in the art and is further defined in detail herein. Accordingly, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:2 will be sequences that are "essentially as set forth in SEQ ID NO:2, provided the biological activity of the protein is maintained. In particular embodiments, the biological activity of a vRNAP protein, polypeptide or peptide, or a biologically functional equivalent, comprises transcription. A preferred transcriptional activity that may be possessed by a vRNAP protein, polypeptide or peptide, or a biologically functional equivalent, is RNA synthesis using single-stranded N4 vRNAP promoter-containing DNA as a template.

In certain other embodiments, the invention concerns isolated nucleic acid segments and recombinant vectors that include within their sequence a nucleic acid sequence essentially as set forth in SEQ ID NO:1. The term "essentially as set forth in SEQ ID NO:1 is used in the same sense as described above and means that the nucleic acid sequence substantially corresponds to a portion of SEQ ID NO:1 and has relatively few codons that are not identical, or functionally equivalent, to the codons of SEQ ID NO:1. Again, nucleic acid segments that encode proteins, polypeptide or peptides exhibiting RNAP activity will be most preferred.

The term "functionally equivalent codon" is used herein to refer to codons that encode the same amino acid, such as the six codons for arginine and serine, and also refers to codons that encode biologically equivalent amino acids. For optimization of expression of vRNAP in human cells, the codons are shown in Table 1 in preference of use from left to right. Thus, the most preferred codon for alanine is thus "GCC," and the least is "GCG" (see Table 1 below). Codon usage for various organisms and organelles can be found at the website http://www.kazusa.or.jp/codon/, incorporated herein by reference, allowing one of skill in the art to optimize codon usage for expression in various organisms using the disclosures herein. Thus, it is contemplated that codon usage may be optimized for other animals, as well as other organisms such as a prokaryote (e.g., an eubacteria), an archaea, an eukaryote (e.g., a protist, a plant, a fungus, an animal), a virus and the like, as well as organelles that contain nucleic acids, such as mitochondria or chloroplasts, based on the preferred codon usage as would be known to those of ordinary skill in the art.

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%, and any range derivable therein, such as, for example, about 50% to about 80%, and more preferably about 81% and about 90%; or even more preferably, between about 91% and about 99%; of nucleotides that are identical to the nucleotides of SEQ ID NO:1 will be sequences that are "essentially as set forth in SEQ ID NO:1".

a. Nucleic Acid Hybridization

The nucleic acid sequences disclosed herein also have a variety of uses. Contiguous sequences from vRNAP nucleic acid sequences can be used, for example, as templates to synthesize vRNAP.

Naturally, the present invention also encompasses DNA segments that are complementary, or essentially complementary, to the sequence set forth in SEQ ID NO:1, 3, 5, 7 and 14. Nucleic acid sequences that are "complementary" are those that are capable of base-pairing according to the standard Watson-Crick complementary rules. As used herein, the term "complementary sequences" means nucleic acid sequences that are complementary, as may be assessed by the same nucleotide comparison set forth above, or as defined as being capable of hybridizing to the nucleic acid segment of SEQ ID NO:1 under stringent conditions such as those described herein.

As used herein, a "DNA/RNA hybrid" is understood to mean that a single strand of RNA is hybridized to a single strand of DNA.

The term "appropriate reaction conditions" as described herein mean that temperature, pH, buffer, and other parameters are adjusted to optimize the reaction rate and yield.

As used herein, "hybridization," "hybridizes" or "capable of hybridizing" is understood to mean the forming of a double or triple stranded molecule or a molecule with partial double or triple stranded nature. The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suit a particular application. For example, in other embodiments, hybridization may be achieved under conditions of 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 MM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1, 3, 5, 7 or 14. Nucleic acid fragments for use as a DNA transcription template may also be prepared. These fragments may be short or of intermediate lengths, such as, for example, about 8, about 10 to about 14, or about 15 to about 20 nucleotides, and that are chromosome-sized pieces, up to about 35,000, about 30,000, about 25,000, about 20,000, about 15,000, about 10,000, or about 5,000 base pairs in length, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

For example, it will be readily understood that "intermediate lengths," in these contexts, means any length between the quoted ranges, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

One will generally prefer to design nucleic acid molecules having complementary sequences over stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

b. Nucleic Acid Amplifcation

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label, or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products, and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence, which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case, the single-stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single-stranded DNA, which is then converted to double-stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

c. Nucleic Acid Detection

In certain embodiments, it will be advantageous to employ nucleic acid sequences of the present invention such as all or part of SEQ ID NO:1, 3, 5, 7, 14 or a mutant thereof in combination with an appropriate means, such as a label, for hybridization assays, RNase protection and Northern hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (see Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an E. coli enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase Protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

Nuclease S1 analysis of reaction products can be used to measure RNA. An exemplary procedure for S1 analysis involves hybridization reaction with the RNA of interest (0.005-0.1 mg) and an excess of S1 probe which comprises a labeled oligonucleotide complementary to 20-80 or more sequential nucleotides of a specific RNA in S1 hybridization buffer (80% formamide, 0.4 M NaCl, 1 mM EDTA, 40 mM Pipes, pH 6.4). After denaturation for 4 min at 94° C., overnight hybridization at 30° C. and precipitation with ethanol, the S1 probe/RNA mixture is resuspended in S1 buffer (0.26 M NaCl, 0.05 M sodium acetate, pH 4.6, and 4.5 mM zinc sulfate). The sample is divided into two volumes and 100 units of S1 nuclease (Sigma Chemical Company) is added to one tube. The samples are incubated for 60 minutes at 37° C.; then EDTA (10 mM final concentration) and 15 g polyI-polyC RNA are added and the sample is extracted with phenol/chloroform and precipitated in ethanol. The samples are then subjected to polyacrylamide gel electrophoresis.

One method to produce a radiolabeled RNA probe with high specific activity includes admixing a radiolabeled NTP during transcription. Suitable isotopes for radiolabeling include $^{35}$S- and $^{32}$P-labeled UTP, GTP, CTP or ATP. For optimal results, a gel-purified radiolabeled RNA probe which is preferentially 300-500 bases in length, with a specific activity of 1-3 X10^8 cpm/μg should be generated using the RNA polymerase of the current invention. In order to produce this in vitro transcript, it is often advisable to use a high specific activity (e.g., [α-$^{32}$P]CTP at 3,000Ci/mmol) NTP. To prevent background hybridization, it is important to remove plasmid template DNA by digestion which can be done with, for example, RQ1 RNase-Free DNase followed by phenol:chloroform:isoamyl alcohol extraction and ethanol precipitation.

Another method for producing radiolabeled probes includes using a riboprobe system which can produce high specific activity, radiolabeled RNA probes or microgram quantities of in vitro transcript. Riboprobes are useful with radiolabeled RNA probes in many applications including RNase protection, Northern hybridization, S1 analysis and in situ hybridization assays. The principle components of an in vitro transcription are the riboprobe, an RNA polymerase, a DNA template which includes a phage RNA polymerase promoter and ribonucleotide triphosphates.

d. Cloning vRNAP Genes

The present invention contemplates cloning vRNAP, or more particularly mini-vRNAP genes. A technique often employed by those skilled in the art of protein production today is to obtain a so-called "recombinant" version of the protein, to express it in a recombinant cell and to obtain the protein, polypeptide or peptide from such cells. These techniques are based upon the "cloning" of a nucleic acid molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, for example, from a phage, bacteria, yeast, fungus, mouse, rat, monkey or human. The screening protocol may utilize nucleotide segments or probes that are designed to hybridize to cDNA or genomic sequences of vRNAPs from protists. Additionally, antibodies designed to bind to the expressed vRNAP proteins, polypeptides, or peptides may be used as probes to screen an appropriate viral, eubacterial, archaebacterial or eukaryotic DNA expression library. Alternatively, activity assays may be employed. The operation of such screening protocols are well known to those of skill in the art and are described in detail in the scientific literature, for example, in Sambrook et al. (1989), incorporated herein by reference. Moreover, as the present invention encompasses the cloning of genomic segments as well as cDNA molecules, it is contemplated that suitable genomic cloning methods, as known to those in the art, may also be used.

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2, 4, 6, 8 or 15 and also larger polypeptides up to and including proteins corresponding to the full-length sequences set forth in SEQ ID NO:2 and SEQ ID NO:15, and any range derivable therein and any integer derivable in such a range. In addition to the "standard" DNA and RNA nucleotide bases, modified bases are also contemplated for use in particular applications of the present invention. A table of exemplary, but not limiting, modified bases is provided herein below.

TABLE 2

Modified Bases

| Abbr. | Modified base description | Abbr. | Modified base description |
|---|---|---|---|
| ac4c | 4-acetylcytidine | Mam5s2u | 5-methoxyaminomethyl-2-thiouridine |
| chm5u | 5-(carboxyhydroxylmethyl)uridine | Man q | Beta,D-mannosylqueosine |
| Cm | 2'-O-methylcytidine | Mcm5s2u | 5-methoxycarbonylmethyl-2-thiouridine |
| Cmnm5s2u | 5-carboxymethylaminomethyl-2-thio-ridine | Mcm5u | 5-methoxycarbonylmethyluridine |
| Cmnm5u | 5-carboxymethylaminomethyluridine | Mo5u | 5-methoxyuridine |
| D | Dihydrouridine | Ms2i6a | 2-methylthio-N6-isopentenyladenosine |
| Fm | 2'-O-methylpseudouridine | Ms2t6a | N-((9-beta-D-ribofuranosyl-2-methylthiopurine-6-yl)carbamoyl)threonine |

TABLE 2-continued

Modified Bases

| Abbr. | Modified base description | Abbr. | Modified base description |
|---|---|---|---|
| gal q | Beta,D-galactosylqueosine | Mt6a | N-((9-beta-D-ribofuranosylpurine-6-yl)N-methyl-carbamoyl)threonine |
| Gm | 2'-O-methylguanosine | Mv | Uridine-5-oxyacetic acid methylester |
| I | Inosine | o5u | Uridine-5-oxyacetic acid (v) |
| I6a | N6-isopentenyladenosine | Osyw | Wybutoxosine |
| m1a | 1-methyladenosine | P | Pseudouridine |
| m1f | 1-methylpseudouridine | Q | Queosine |
| m1g | 1-methylguanosine | s2c | 2-thiocytidine |
| m1I | 1-methylinosine | s2t | 5-methyl-2-thiouridine |
| m22g | 2,2-dimethylguanosine | s2u | 2-thiouridine |
| m2a | 2-methyladenosine | s4u | 4-thiouridine |
| m2g | 2-methylguanosine | T | 5-methyluridine |
| m3c | 3-methylcytidine | t6a | N-((9-beta-D-ribofuranosylpurine-6-yl)carbamoyl)threonine |
| m5c | 5-methylcytidine | Tm | 2'-O-methyl-5-methyluridine |
| m6a | N6-methyladenosine | Um | 2'-O-methyluridine |
| m7g | 7-methylguanosine | Yw | Wybutosine |
| Mam5u | 5-methylaminomethyluridine | X | 3-(3-amino-3-carboxypropyl)uridine, (acp3)u |

III. Recombinant Vectors, Promoters, Host Cells and Expression

Recombinant vectors form an important further aspect of the present invention. The term "expression vector or construct" means any type of genetic construct containing a nucleic acid coding for a gene product in which part or all of the nucleic acid encoding sequence is capable of being transcribed. The transcript may be translated into a proteinaceous molecule, but it need not be, such as in the case of minivRNAP transcribing an RNA using a single-stranded DNA template. Thus, in certain embodiments, expression includes both transcription of a single-stranded DNA and translation of an RNA into the protein product. In other embodiments, expression only includes transcription of the nucleic acid. A recombinant vector can also be used for delivery of the RNA of the current invention.

Particularly useful vectors are contemplated to be those vectors in which the coding portion of the DNA segment, whether encoding a full length protein or smaller polypeptide or peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

One particularly useful vector is pBAD. The pBAD expression vectors allow for greater control of bacterial expression of recombinant proteins and allow tight regulation for turning expression on or off. pBAD vectors allow for dose dependent induction for modulation of expression levels. The pBAD expression system helps overcome two of the most common problems of heterologous protein expression in bacteria: toxicity of the recombinant protein to the host and insolubility of the recombinant protein when it is expressed at high, uncontrolled levels. In both cases, a tightly-regulated expression system is critical for maximizing recombinant protein yields. The pBAD expression system is based on the araBAD operon which controls the arabinose metabolic pathway in *E. coli* and allows for precise modulation of heterologous expression to levels that are optimal for recovering high yields of the protein of interest (Guzman et al., 1995).

a. Promoters

Any promoters normally found in a host cell in the native state can be used in the present invention to drive expression of N4 vRNA or mini-vRNA polymerase. Also, promoters not normally found in the host cell in the native state that are recognized by a native, normally native host cell RNA polymerase, or non-native RNA polymerase expressed in the cell can be used in the present invention to drive expression of the RNA polymerase. Other promoters may be selected from a nucleic acid sequence database accessible to those of skill in the art, e.g., GenBank, or the promoter can be isolated by a screening method. A promoter recognized by the host cell can be operably linked to the gene or genes encoding the N4 RNA polymerase. The operable linkage can be constructed using any known techniques for DNA manipulation, as referred to herein.

Promoters are described as either constitutive or inducible. Constitutive promoters actively drive expression of genes under their control. Inducible promoters, in contrast, are activated in response to specific environmental stimuli. Both constitutive and inducible promoters can be used in the present invention for expressing non-host genes in a host cell.

Inducible promoters include, but are not limited to, trp, tac, lac, ara, reca, λPr, and λP1. These promoters and others that can be used in the present invention for expression of the N4 vRNA or mini-vRNA polymerase, in embodiments in which the host cell is *E. coli*, are described by Makrides, Microbiological Reviews, (1996), 60, 512-538, herein incorporated by reference. Further, in embodiments of the present invention wherein the host cell is a microbe other than *E. coli*, such as Saccharomyces, Bacillus, and Pseudomonas, any inducible promoter known to those skilled in the art to be active in the host cell can be used to drive expression of the heterologous RNA polymerase. (U.S. Pat. No. 6,218,145).

The promoter may be in the form of the promoter that is naturally associated with N4 vRNA or mini-vRNA polymerase, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with N4 vRNA or mini-vRNA polymerase in its natural environment. Such promoters may include promoters normally associated with other genes, and/or promoters isolated from any other bacterial, viral, eukaryotic, protist, or mammalian cell, and/or promoters made by the hand of man that are not "naturally occurring," i e., containing different elements from different promoters, or mutations that increase, decrease, or alter expression.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins, polypeptides or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase promoter, the spacing between promoter elements can be increased to 50 base pairs apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of the instant nucleic acids. The use of other viral or mammalian cellular or bacterial phage promoters which are well-known in the art to achieve expression are contemplated as well, provided that the levels of expression are sufficient for a given purpose. Tables 3 and 4 below list several elements/promoters which may be employed, in the context of the present invention, to regulate the expression of a vRNAP gene. This list is not intended to be exhaustive of all the possible elements involved in the promotion of expression but, merely, to be exemplary thereof.

In certain embodiments of the invention, promoter sequences may be used that that are recognized specifically by a DNA-dependent RNA polymerase, such as, but not limited to, those described by Chamberlin and Ryan (1982) and by Jorgensen et al., (1991). These promoters can be used to express a wild-type or mutant form of a miniV RNA polymerase of the invention. Several RNA polymerase promoter sequences are especially useful, including, but not limited to, promoters derived from SP6 (e.g., Zhou and Doetsch, 1993), T7 (e.g., Martin, and Coleman, 1987) and T3 (e.g., McGraw et al., 1985). An RNA polymerase promoter sequence derived from *Thermus thermophilus* can also be used (see, e.g., Wendt et al., 1990; Faraldo et al., 1992; Hartmann et al., 1987; Hartmann et al., 1991). The length of the promoter sequence will vary depending upon the promoter chosen. For example, the T7 RNA polymerase promoter can be only about 25 bases in length and act as a functional promoter, while other promoter sequences require 50 or more bases to provide a functional promoter.

In other embodiments of the invention, a promoter is used that is recognized by an RNA polymerase from a T7-like bacteriophage. The genetic organization of all T7-like phages that have been examined has been found to be essentially the same as that of T7. Examples of T7-like phages according to the invention include, but are not limited to *Escherichia coli* phages T3, .phi.I, .phi.II, W31, H, Y, A1, 122, cro, C21, C22, and C23; *Pseudomonas putida* phage gh-1; *Salmonella typhimurium* phage SP6; *Serratia marcescens* phages IV; Citrobacter phage ViIII; and Klebsiella phage No. 11 (Hausmann, 1976; Korsten et al., 1975; Dunn, et al. 1971; Towle, et al., 1975; Butler and Chamberlin, 1982).

When a T7 RNA polymerase promoter, or another T7-like RNA polymerase promoter is used to express a wild-type or mutant form of a gene for a miniV RNA polymerase of the invention, the gene can be expressed in a host cell which expresses the T7 RNA polymerase, or the corresponding T7-like RNA polymerase for the promoter used, wherein the RNA polymerase for the promoter is expressed either constitutively, or more preferably, from an inducible promoter. By way of example, a T7 RNA polymerase expression system, such as, but not limited to, the expression systems disclosed in, for example, U.S. Pat. Nos. 5,693,489 and 5,869,320, the disclosures of which are incorporated herein by reference in their entirety.

b. Enhancers

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB, http://www.epd.isb-sib.ch/) could also be used to drive expression. Eukaryotic cells can support cytoplasmic transcription from certain bacterial promoters if the appropriate bacterial polymerase is provided, either as part of the delivery complex or as an additional genetic expression construct.

TABLE 3

Promoter and Enhancer Elements

| Promoter/Enhancer | References |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al.; 1990 |
| Immunoglobulin Light Chain | Queen and Baltimore, 1983; Picard and Schaffner, 1984 |

TABLE 3-continued

Promoter and Enhancer Elements

| Promoter/Enhancer | References |
|---|---|
| T-Cell Receptor | Luria et al., 1987; Winoto and Baltimore, 1989; Redondo et al.; 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | |
| c-HA-ras | Deschamps et al., 1985 |
| Insulin | Edlund et al., 1985 |
| Neural Cell Adhesion Molecule (NCAM) | Hirsh et al., 1990 |
| α$_{1\text{-Antitrypsin}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |
| Polyoma | Swartzendruber and Lehman, 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |

TABLE 3-continued

Promoter and Enhancer Elements

| Promoter/Enhancer | References |
|---|---|
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 4

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | Poly(rI)x and Poly(rc) | Tavernier et al., 1983 |
| Adenovirus 5 E2 | E1a | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1a, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Turning to the expression of the proteinaceous molecules after transcription using the vRNAP, mini-vRNAP, or mutants thereof of the present invention, once a suitable clone or clones have been obtained, whether they be cDNA based or genomic, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteinaceous molecules of the present invention.

Both cDNA and genomic sequences are suitable for eukaryotic expression, as the host cell will generally process the genomic transcripts to yield functional mRNA for translation into proteinaceous molecules. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

c. Antisense and Ribozymes

In some embodiments of the invention the vRNA polymerase can be used to synthesize antisense RNA or ribozymes.

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport, translation, and/or stability. Targeting double-stranded (ds) DNA with oligonucleotides leads to triple-helix formation; targeting RNA will lead to double-helix formation. An antisense nucleic acid may be complementary to SEQ ID NO:1, 3, 5, 7 or 14, complementary to a mini-vRNAP encoding sequence or to mini-vRNAP non-coding sequences. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries (splice junctions) of a gene. It is contemplated that the most effective antisense constructs may include regions complementary to intron/exon splice junctions. Thus, antisense constructs with complementary regions within 50-200 bases of an intron-exon splice junction may be used. It has been observed that some exon sequences can be included in the construct without seriously affecting the target selectivity thereof The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vivo to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Sequences for ribozymes may be included in the DNA template to eliminate undesired 5' end sequences in RNAs generated through T7 RNA polymerase transcription.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples of ribozymes include sequences from the Group I self-splicing introns including tobacco ringspot virus (Prody, et al., 1986), avocado sunblotch viroid (Palukaitis, et al., 1979; Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan, et al., 1992; Yuan and Altman, 1994), hairpin ribozyme structures (Berzal-Herranz, et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complementary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in ribozymes is simply a matter of preparing and testing a given sequence, and is a routinely practiced "screening" method known to those of skill in the art.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

d. Host Cells

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryotic host cell for replication of many vector copies. Bacterial cells used as host cells for vector replication and/or expression include DH5α, BL 21, JM109, and KC8, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells. Appropriate yeast cells include *Saccharomyces cerevisiae, Saccharomyces pombe,* and *Pichia pastoris.*

Examples of eukaryotic host cells for replication and/or expression of a vector include HeLa, NIH3T3, Jurrat, 293, Cos, CHO, Saos, BHK, C127 and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and/or their cognate polypeptides, proteins, or peptides.

It is proposed that vRNAP, or more particularly mini-vRNAP may be co-expressed with other selected proteinaceous molecules such as EcoSSB and other proteins of interest, wherein the proteinaceous molecules may be co-expressed in the same cell or vRNAP gene may be provided to a cell that already has another selected proteinaceous molecule. Co-expression may be achieved by co-transfecting the cell with two distinct recombinant vectors, each bearing a copy of either of the respective DNAs. Alternatively, a single recombinant vector may be constructed to include the coding regions for both of the proteinaceous molecules, which could then be expressed in cells transfected with the single vector. In either event, the term "co-expression" herein refers to the expression of both the vRNAP gene and the other selected proteinaceous molecules in the same recombinant cell.

As used herein, the terms "engineered" and "recombinant" cells or host cells are intended to refer to a cell into which an exogenous DNA segment or gene, such as a cDNA or gene encoding vRNAP, mini-vRNAP or a mutant thereof, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant vRNAP, whether mutant or wild-type, in accordance with the present invention one would prepare an expression vector that comprises a wild-type, or mutant vRNAP proteinaceous molecule-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter directs transcription of the DNA and promotes expression of the encoded recombinant protein, polypeptide or peptide. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host expression systems. Cell types available for expression include, but are not limited to, bacteria, such as *E. Coli* and *B. subtilis,* transformed with recombinant bacteriophage DNA, plasmid DNA or cosmid DNA expression vectors.

Certain examples of prokaryotic hosts are *E. coil* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis;* and other enterobacteriaceae such as *Salmonella typhimurium, Serratia marcescens,* and various *Pseudomonas* species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble proteins for later purification and separation or cleavage.

The following details concerning recombinant protein production in bacterial cells, such as *E. coli,* are provided by way of exemplary information on recombinant protein production in general, the adaptation of which to a particular recombinant expression system will be known to those of skill in the art.

Bacterial cells, for example, *E. coli,* containing the expression vector are grown in any of a number of suitable media, for example, LB. The expression of the recombinant proteinaceous molecule may be induced, e.g., by adding IPTG or any appropriate inducer to the media or by switching incubation to a higher temperature, depending on the regulated promoter used. After culturing the bacteria for a further period, generally of between 2 and 24 hours, the cells are collected by centrifugation and washed to remove residual media.

The bacterial cells are then lysed, for example, by disruption in a cell homogenizer, by sonication or cell press and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant proteinaceous molecule is expressed in the inclusion bodies, as is the case in many instances, these can be washed in any of several solutions to remove some of the contaminating host proteins, then solubilized in solutions containing high concentrations of urea (e.g., 8M) or chaotropic agents such as guanidine hydrochloride in the presence of reducing agents, such as β-mercaptoethanol or DTT (dithiothreitol).

Under some circumstances, it may be advantageous to incubate the proteinaceous molecule for several hours under conditions suitable for the proteinaceous molecule to undergo a refolding process into a conformation which more closely resembles that of the native proteinaceous molecule. Such conditions generally include low proteinaceous molecule concentrations, less than 500 mg/ml, low levels of reducing agent, concentrations of urea less than 2 M and often the presence of reagents such as a mixture of reduced and oxidized glutathione which facilitate the interchange of disulfide bonds within the proteinaceous molecule.

The refolding process can be monitored, for example, by SDS-PAGE, or with antibodies specific for the native molecule (which can be obtained from animals vaccinated with the native molecule or smaller quantities of recombinant proteinaceous molecule). Following refolding, the proteinaceous molecule can then be purified further and separated from the refolding mixture by chromatography on any of several supports including ion exchange resins, gel permeation resins or on a variety of affinity columns.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase or other glycolytic enzymes, such as enolase, glyceraldehyde-3-phosphate protein, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more RNAP coding sequences.

Different host cells have characteristic and specific mechanisms for the post-translational processing and modification of proteinaceous molecules. Appropriate cells lines or host systems can be chosen to ensure the correct modification and processing of the foreign proteinaceous molecule expressed.

A number of viral-based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing an RNA in infected hosts.

Specific initiation signals may also be used for more efficient translation using the vRNAP of the current invention. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the proteinaceous molecule at a position prior to transcription termination.

For long-term, high-yield production of a recombinant vRNAP protein, polypeptide or peptide, stable expression is preferred. For example, cell lines that stably express constructs encoding a vRNAP protein, polypeptide or peptide may be engineered. Rather than using expression vectors that contain viral origins of replication, host cells can be transformed with vectors controlled by appropriate expression control elements (e.g., promoter, enhancer sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk⁻, hgprt⁻ or aprt⁻ cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Large scale suspension culture of bacterial cells in stirred tanks is a common method for production of recombinant proteinaceous molecules. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor for microbial fermentation relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the vRNAP proteins, polypeptides or peptides of the invention may be "overexpressed," i.e., expressed in increased levels relative to its natural expression in cells. Such overexpression may be assessed by a variety of methods, including radio-labeling and/or proteinaceous molecule purification. However, simple and direct methods are preferred, for example, those involving SDS/PAGE and proteinaceous composition staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific proteinaceous molecule in relation to the other proteins produced by the host cell and, e.g., visible on a gel.

IV. Methods of Gene Transfer

In order to mediate the effect of transgene expression in a cell, it will be necessary to transfer the expression constructs (e.g., a therapeutic construct) of the present invention into a cell. Such transfer may employ viral or non-viral methods of gene transfer. This section provides a discussion of methods and compositions of gene or nucleic acid transfer, including transfer of antisense sequences.

The vRNAP genes are incorporated into a viral vector to mediate gene transfer to a cell. Additional expression constructs encoding EcoSSB and other therapeutic agents as described herein may also be transferred via viral transduction using infectious viral particles, for example, by transformation with an adenovirus vector of the present invention. Alternatively, a retrovirus, bovine papilloma virus, an adeno-associated virus (AAV), a lentiviral vector, a vaccinia virus, a polyoma virus, or an infective virus that has been engineered to express a specific binding ligand may be used. Similarly, nonviral methods which include, but are not limited to, direct delivery of DNA such as by injection, electroporation, calcium phosphate precipitation, liposome mediated transfection, and microprojectile bombardment may be employed. Thus, in one example, viral infection of cells is used in order to deliver therapeutically significant genes to a cell. Typically, the virus simply will be exposed to the appropriate host cell under physiologic conditions, permitting uptake of the virus.

Microinjection can be used for delivery into a cell. Microinjection involves the insertion of a substance such as RNA into a cell through a microelectrode. Typical applications include the injection of drugs, histochemical markers (such as horseradish peroxidase or lucifer yellow) and RNA or DNA in molecular biological studies. To extrude the substances through the very fine electrode tips, either hydrostatic pressure (pressure injection) or electric currents (ionophoresis) is employed.

V. Proteinaceous Compositions

In certain embodiments, the present invention concerns novel compositions or methods comprising at least one proteinaceous molecule. The proteinaceous molecule may have a sequence essentially as set forth in SEQ ID NO:2, 4, 6, 8 or 15. The proteinaceous molecule may be a vRNAP or more preferably a mini-vRNAP, or a delivery agent. The proteinaceous molecule may also be a mutated mini-vRNAP.

As used herein, a "proteinaceous molecule," "proteinaceous composition," "proteinaceous compound," "proteinaceous chain" or "proteinaceous material" generally refers to, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 5 below.

TABLE 5

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide, such as vRNAP or mini-vRNAP. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art.

Alternatively, various commercial preparations of proteins, polypeptides and peptides are known to those of skill in the art.

In certain embodiments, a proteinaceous compound may be purified. Generally, "purified" will refer to a specific or desired protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. A mini-vRNAP antibody may comprise all or part of an antibody that specifically recognizes mini-vRNAP. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that the high viscosity will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about −80° C. for at least about 12 hours and then centrifuged at about 12,000 times g for about 15 minutes to obtain the precipitate. The precipitate, such as fibrinogen may be stored for up to about one year (Oz, 1990).

VI. Protein Purification

To prepare a composition comprising a vRNAP or mini-vRNAP, it is desirable to purify the components or variants thereof. Purification of the mini-vRNAP (SEQ ID NO:4) can be done in two step using affinity columns. The mini-vRNAP of SEQ ID NO:6 has been modified to comprise a His tag such that purification can be done in a single step when using metal affinity columns such as those which employ nickel, cobalt or zinc. The full length vRNAP of SEQ ID NO:15 is also His tagged for purification.

According to one embodiment of the present invention, purification of a peptide comprising vRNAP can be utilized ultimately to operatively link this domain with a selective agent. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is affinity chromatography.

A tag may be used for protein or peptide purification and detection such as hexahistidine (6-His, HHHHHH), FLAG (DYKDDDDK), hemaglutinin (HA, YPYDVPDYA) and c-myc (EQKLISEEDL). Other tags also have been generated, most of which are very small, comprising only a few amino acids, and are therefore likely to have little to no effect on the conformation of the mature protein or peptide. These small tags do not require any special conformation to be recognized by antibodies. Systems for protein purification using these tags include NTA resin (6-His) or the FLAG fusion system marketed by IBI (FLAG) where the fusion protein is affinity-purified on an antibody column.

Certain aspects of the present invention concern the purification, and in particular embodiments, the substantial purification, of an encoded protein or peptide, such as a vRNAP. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition, such as the vRNAP, that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification" number. The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

Ion exchange chromatography is a preferred method of separation. Using columns resins such as the metal affinity chromatography resin TALON are also preferred. TALON resin has an enhanced resolving power for polyhistidine-tagged proteins. This results in greater purity with less effort. TALON employs cobalt, an electropositive metal with a remarkably high affinity for polyhistidine-tagged proteins and a low affinity for other proteins. Often, no discernible binding of host proteins occurs and a separate wash step is not required. The binding properties of cobalt allow protein elution under mild pH conditions that protect protein integrity.

Further concentration of the proteins can be done on an anion exchange column, such as the MonoQ column, a high resolution, anion exchange column. This column works at pressures less than 5 MPa, has a high capacity and gives very high chromatographic resolution.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography, a particularly efficient method of purifying peptides, is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature). Tags, as described herein above, can be used in affinity chromatography.

The matrix should be a substance that itself does not adsorb molecules to any significant extent and that has a broad range of chemical, physical and thermal stability. The ligand should be coupled in such a way as to not affect its binding properties. The ligand also should provide relatively tight binding, and it should be possible to elute the substance without destroying the sample or the ligand. One of the most common forms of affinity chromatography is immunoaffinity chromatography. The generation of antibodies that would be suitable for use in accordance with the present invention is discussed below.

An affinity column may have an N4 promoter which the vRNAP or mini-vRNAP proteins recognize attached to a matrix. This column would be suitable for use for the purification of polymerases with no additional tags such as histidine tags.

VII. Separation, Quantitation, and Identification Methods

Following synthesis of the RNA, it may be desirable to separate the amplification products of several different lengths from each other and from the template and the excess primer.

a. Gel Electrophoresis

In one embodiment, amplification products are separated by agarose, agarose-acrylamide or polyacrylamide gel electrophoresis using standard methods (Sambrook et al., 1989).

b. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin-labeled or antigen-labeled, can be captured with beads bearing avidin or antibody, respectively.

c. Microfluidic Techniques

Microfluidic techniques include separation on a platform such as microcapillaries, designed by ACLARA BioSciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487 to Wilding et al., and 5,296,375 to Kricka et al., discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

d. Capillary Electrophoresis

In some embodiments, it may be desirable to provide an additional, or alternative means for analyzing the amplified genes. In these embodiments, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. The use of microcapillary electrophoresis in size separation of nucleic acids has been reported in, e.g., Woolley and Mathies, 1994. Microcapillary array electrophoresis generally provides a rapid method for size-based sequencing, PCR™ product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, e.g., Jacobsen et al., 1994; Effenhauser et al., 1994; Harrison et al., 1993; Effenhauser et al., 1993; Manz et al., 1992; and U.S. Pat. No. 5,904,824. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Tsuda et al., 1990, describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

e. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods known in the art can be found summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include K. H. Schram (1990); and P. F. Crain (1990). The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al. 1987).

Two ionization/desorption techniques are electrospray/ionspray (ES) and matrix-assisted laser desorption/ionization (MALDI). ES mass spectrometry was introduced by Fenn et al. 1984; WO 90/14148 and its applications are summarized in review articles (R. D. Smith et al. 1990; B. Ardrey, 1992). As a mass analyzer, a quadrupole is most frequently used. The determination of molecular weights in femtomole amounts of sample is very accurate due to the presence of multiple ion peaks, which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. (1990). Since, in most cases, no multiple molecular ion peaks are produced with this technique, the mass spectra, in principle, look simpler compared to ES mass spectrometry. DNA molecules up to a molecular weight of 410,000 Daltons could be desorbed and volatilized (Williams et al., 1989). More recently, the use of infra red lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides (Berkenkamp et al., 1998). Berkenkamp et al., 1998, also describe how DNA and RNA samples can be analyzed by limited sample purification using MALDI-TOF IR.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

f. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed (Forster, 1948). The distance between donor and acceptor dyes at which energy transfer efficiency is 50% is referred to as the Forster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Several formats for FET hybridization assays are reviewed in Nonisotopic DNA Probe Techniques (1992).

Homogeneous methods employing energy transfer or other mechanisms of fluorescence quenching for detection of nucleic acid amplification have also been described. Higuchi et al. (1992) disclose methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee, et al. (1993) disclose a real-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved. WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/Texas Red (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms, it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and may be routinely used to link the donor and acceptor dyes at their respective sites in the detector nucleic acid.

g. In Vitro Studies

The synthesized RNA of the current invention may be used for in vitro studies of spliceosome assembly, splicing reactions, or antisense experiments.

The spliceosome is a large, multisubunit complex consisting of small, nuclear ribonucleoprotein particles (snRNPs). There are a total of 5 snRNAs: U1, U2, U4, U5, and U6 which are small and uridine rich. Each snRNP has 1 or 2 of these RNAs. In addition to catalyzing the splicing reaction, the spliceosome retains intermediate products, positions splice sites for precise joining of the exons, and prevents exons from diffusing away after cleavage and before ligation. Spliceosome catalysis involves concerted cleavage/ligation reactions in which the 2'-OH of branch site A attacks the 5' splice site to form a 2'-5' phosphodiester bond with the first nucleotide of the intron. The resulting 3'-OH at the end of the 5' exon attacks the 3' splice site to release the lariat form of the intron and join the two exons together with a normal 3'-5' phosphodiester bond. At least 50 different proteins are involved in spliceosome assembly and function. In the group I and group II introns, splicing is improved (in velocity and accuracy) by protein factors (Coetze et al., 1994; Mohr et al., 1994).

VIII. Kits

Any of the compositions described herein may be comprised in a kit. In a non-limiting example, a vRNAP or more preferably a mini-vRNAP, a derivatized mini-vRNAP, a mutant vRNAP and/or additional agent, may be comprised in a kit. The kits will thus comprise, in suitable container means, a vRNAP, mini-vRNAP, a derivatized mini-vRNAP, a mutant vRNAP and/or an additional agent of the present invention. The inventors envisage other components that may be included in a kit. These include but are not limited to immunodetection agents such as peroxidase and alkaline phosphatase linked monoclonal and polyclonal antibodies, immunoprecipitation reagents such as protein A- or protein G-linked beads, immune cell purification reagents such as a TALON or monoQ column, cloning reagents for the purpose of manipulating an expression vector, and protein expression reagents including prokaryotic and eukaryotic cells lines for the purpose of protein expression.

The kits may comprise a suitably aliquoted vRNAP, mini-vRNAP, a derivatized mini-vRNAP, a mutant vRNAP and/or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the vRNAP, lipid, additional agent, and any other reagent containers in close confinement for commercial sale. Such containers may include injection or blow-molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

The kits of the present invention will also typically include a means for containing the vials in close confinement for commercial sale, such as, e.g., injection and/or blow-molded plastic containers into which the desired vials are retained.

As used herein in the specification, "a" or "an" may mean one or more. As used herein in the claim(s), when used in conjunction with the word "comprising," the words "a" or "an" may mean one or more than one. As used herein "another" may mean at least a second or more.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of a Transcriptionally Active Domain of N4 Virion RNA Polymerase To determine the minimal domain possessing RNA polymerase activity, controlled proteolysis was performed followed by catalytic (transcriptional) autolabeling (Hartmann, et al., 1988). Upon incubation of RNA polymerase with a benzaldehyde derivative of the initiating nucleotide, the benzaldehyde group forms a Schiff-base with the ε-amino group of lysines located within 12 Å of the nucleotide-binding site. The crosslinking step was performed in the presence of DNA template because it stimulates binding of the initiating nucleotide. The unstable Schiff-base is converted to a stable secondary amine by reduction under mild conditions with sodium borohydride, with concomitant reduction of any non-reacted benzaldehyde derivative. Addition of the next template-directed $\alpha$-$^{32}$P labeled NTP leads to phosphodiester bond formation and catalytic autolabeling of the transcriptionally active polypeptide. Controlled trypsin proteolysis of vRNAP was performed, followed by catalytic autolabeling and analysis on SDS-PAGE (FIG. 3A). Initially, three proteolytic fragments are generated, of which the smaller two are catalytically active. Upon further incubation with trypsin, a single stable, transcriptionally active product approximately 1,100 amino acids in length remains. N-terminal sequencing of the three initial proteolytic fragments (FIG. 3B) indicated that the stable active polypeptide (mini-vRNAP) corresponds to the middle ⅓ of vRNAP, the region containing the three motifs described above (FIG. 2A, SEQ ID NOS:3-4).

Example 2

Cloning and Purification of N4 mini-vRNAP

Figure 4:
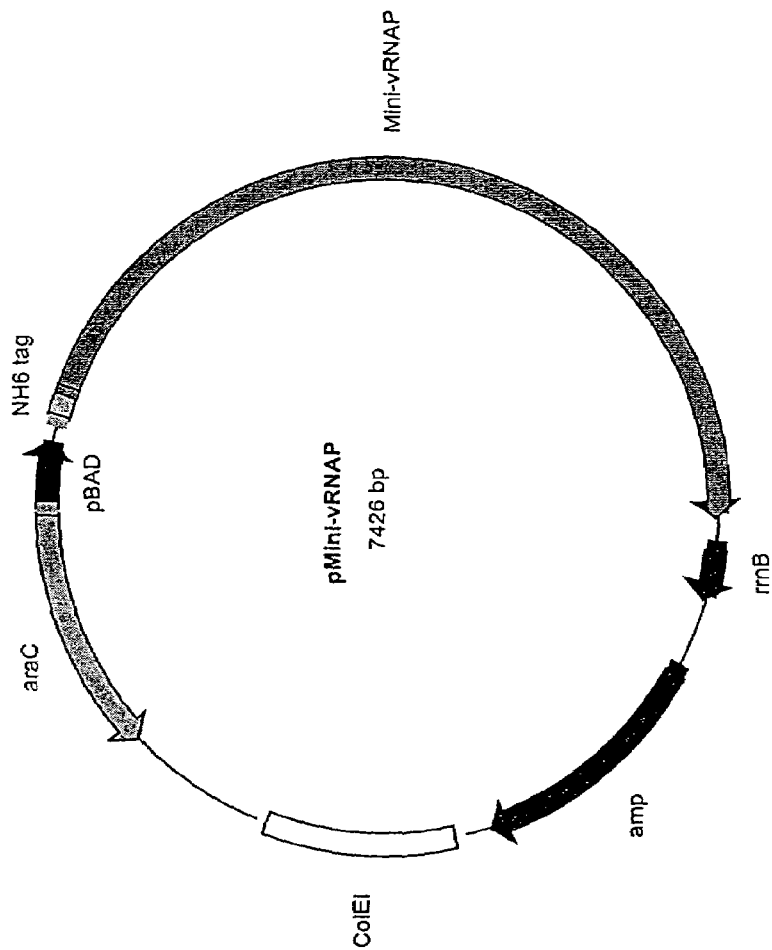
FIG. 4—ORFs for full length polymerase, mini-vRNAP and mutants thereof were cloned under pBAD control with an N-terminal hexahistidine tag.
Figure 5:
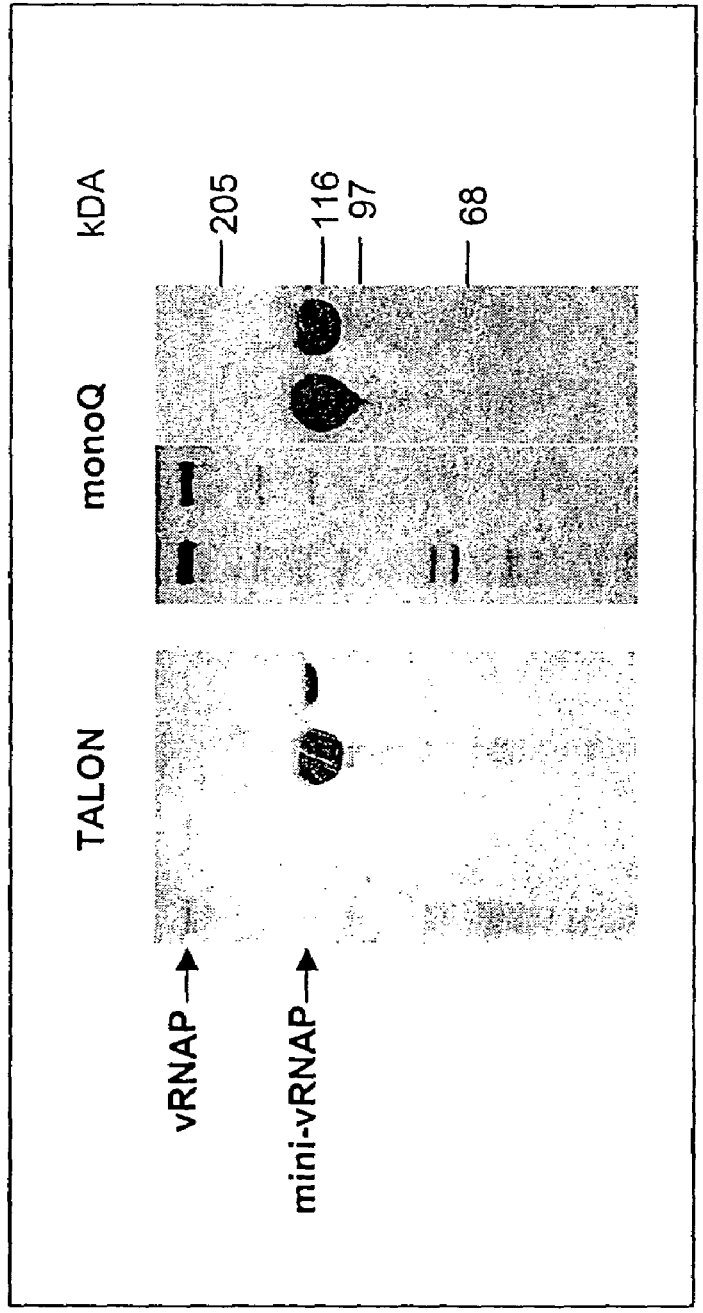
FIG. 5—Purification of cloned vRNAP and mini-vRNAP. The left hand side shows the relative amounts of full size and mini-vRNAP proteins purified on TALON columns from the same volume of induced cells. Further concentration on a monoQ column reveals that, in contrast to full size vRNAP, mini-vRNAP is stable after induction (right).

The full-size vRNAP and the mini-vRNAP (SEQ ID NOS:6 and 15) ORFs were cloned under pBAD control with an N-terminal hexahistidine tag (FIG. 4). The mini-vRNAP domain was cloned into the pBAD B expression plasmid, which was purchased from Invitrogen. Five restriction enzyme sites within pBAD B have been altered; the SnaI site was converted to a HpaI site, and the PflMI and EcoRV sites were destroyed, all by site-directed mutagenesis. The BstBI and HindIII sites were destroyed by enzyme digestion followed by Klenow treatment and re-ligation. FIG. 5 (left) shows the relative amounts of full-length and mini-vRNAP proteins purified on TALON columns from the same volume of E. coli BL21 induced cells. Cloned mini-vRNAP is expressed at 100-fold higher levels than cloned full size vRNAP. Further concentration on a MonoQ column reveals that, in contrast to full size vRNAP, mini-vRNAP is stable after induction (FIG. 5, right). At least 10 mg of mini-vRNAP at a 20 mg/ml concentration are obtained from 1 L of induced cells in just two purification steps: TALON and MonoQ mini-columns. A non-histagged version of mini-vRNAP has also been cloned (SEQ ID NO:4). In this case, the enzyme is purified from a crude extract of induced cells in two steps: a promoter DNA-affinity column and MonoQ.

Mini-vRNAP possesses a high binding affinity (Kd=1 nM) for N4 promoter-containing DNA oligonucleotides. This property was used for purification of non-his tagged mini-vRNAP (SEQ ID NO:4) on a DNA-affinity column. The column was prepared by adsorbing a 5' biotinylated N4 promoter-containing DNA oligonucleotide onto the matrix of a 1 ml HiTrap Streptavidin column (Pharmacia/Amersham Cat.#17-5112-01) according to the manufacturer's instructions. A debris-free sonicate of bacterial cells expressing mini-vRNAP was passed through the column. To bind mini vRNAP to the DNA-affinity column, the pH in the extract and binding/washing buffer should be between 5 to 9, and the NaCl concentration should be between 50 mM and 2M. Nucleases in the extract are inhibited by addition of 2 mM EDTA. After washing the column, mini-vRNAP was eluted with warm (25° C.) water; the elution temperature was raised from 4° C. to 25° C. to increase mini-vRNAP recovery. For complete elution, the temperature can be raised up to 43° C. without significant change in the quality of the preparation. Elution under these conditions occurs due to the removal of metal ions and consequent melting of the promoter hairpin and dissociation of mini-vRNAP. Different DNA oligonucleotides containing variants of the P2 promoter (SEQ ID NOS: 16-19), were used in DNA-affinity columns and tested in mini-vRNAP affinity purification. The best yield was achieved using the DNA oligonucleotide of SEQ ID NO:16. However, the DNA oligonucleotides of SEQ ID NOS:19-20 require a lower temperature than the DNA oligonucleotide of SEQ ID NO:16 for complete elution of the protein, in agreement with the lower thermal stability of the respective promoter hairpins.

Up to 1 mg of mini-vRNAP of 90% purity is obtained from a crude extract of 100 ml E coli culture expressing mini-vRNAP in a single purification step using a 1 ml DNA-affinity column. The binding capacity of the DNA-affinity column was not detectably decreased by multiple use.

Example 3

Effect of EcoSSB on Transcription of Single-Stranded Templates

Figure 6:
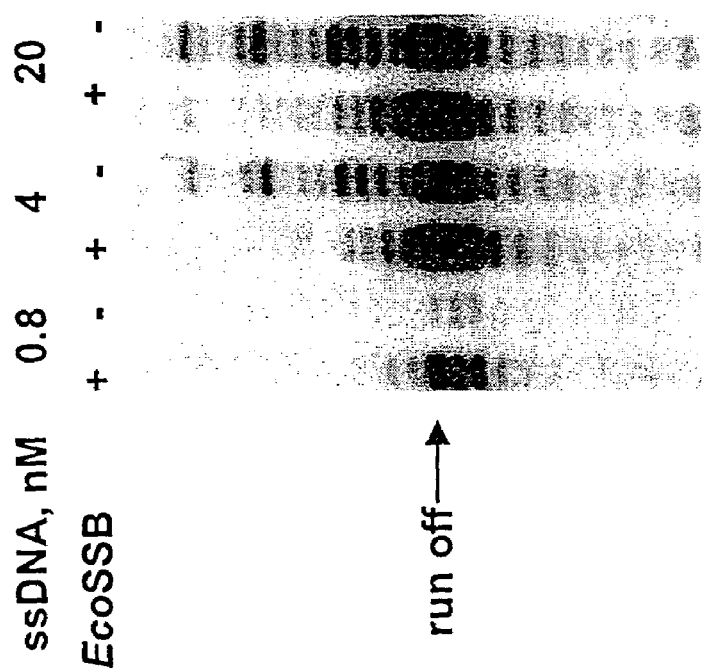
FIG. 6—Activation of N4 vRNAP transcription by EcoSSB at three different ssDNA concentrations. The extent of EcoSSB activation is template-concentration dependent, with highest activation at low DNA template concentration.

Inventors have previously shown that EcoSSB is required for N4 vRNAP transcription in vivo (Glucksmann, et al, 1992). EcoSSB is unique in that, unlike other SSBs whose effect on vRNAP transcription was tested, it does not melt the promoter hairpin structure (Glucksmann-Kuis, et al., 1996). Recently, inventors have reinvestigated the effect of EcoSSB on vRNAP transcription of single-stranded templates. FIG. 6 shows transcription in the absence and presence of Eco SSB at three different ssDNA template concentrations. The extent of EcoSSB activation is template-concentration dependent, with highest activation at low DNA template concentration. These results suggest that EcoSSB overcomes template limitation on ssDNA templates.

Figure 7:
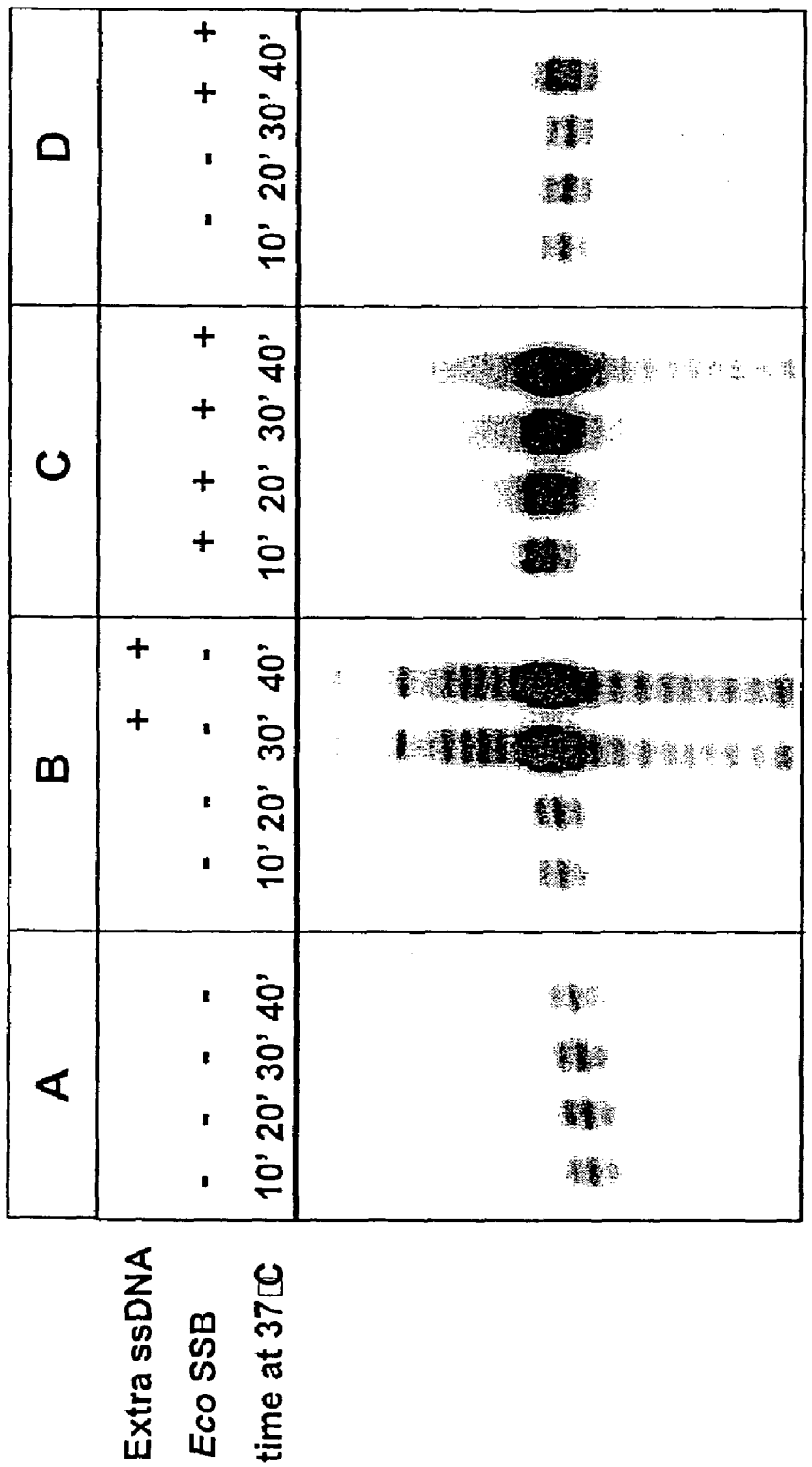
FIG. 7A, FIG. 7B, FIG. 7C, and FIG. 7D—Effect of EcoSSB on ssDNA template recycling. In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). RNA synthesis increased linearly throughout the period of incubation (FIG. 7C). Addition of EcoSSB at 20 min led to a slow rate of transcriptional recovery (FIG. 7D).

To further explore this hypothesis, the effect of addition of template or EcoSSB to transcription reactions after 20 min incubation in the absence of EcoSSB was tested. The transcription reaction mixtures (5-50 µl) contained 20 mM Tris-HCl (pH 7.9 at 25° C.), 10 mM MgCl$_2$, 50 mM NaCl, 1 mM dithiothreitol, 0.01-1 µM mini-vRNAP, 1-100 nM ssDNA template (30-100 nt long, synthesized by Integrated DNA Technologies), 1 mM each of 3 non-labeled NTPs, 0.1 mM $\alpha$-$^{32}$P NTP (1-2 Ci/mmol, NEN), and 1-10 µM E. coli SSB. Incubation was for 1 to 80 min at 37° C. at the indicated temperature. In the presence of EcoSSB, RNA synthesis increased linearly throughout the period of incubation (FIG. 7C). In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). Addition of EcoSSB at 20 min led to a slow rate of transcriptional recovery (FIG. 7D). These results suggest that EcoSSB converts the template from a transcriptionally inactive RNA:DNA hybrid to transcriptionally active single-stranded DNA.

To test this hypothesis, the physical states of the DNA template and the RNA product were analyzed by native gel electrophoresis in the absence and in the presence of EcoSSB. In order to have effective transcription in the absence of EcoSSB, transcription was performed at an intermediate (5 nM) DNA concentration, at which only a 2-fold effect of EcoSSB is observed.

Figure 8:
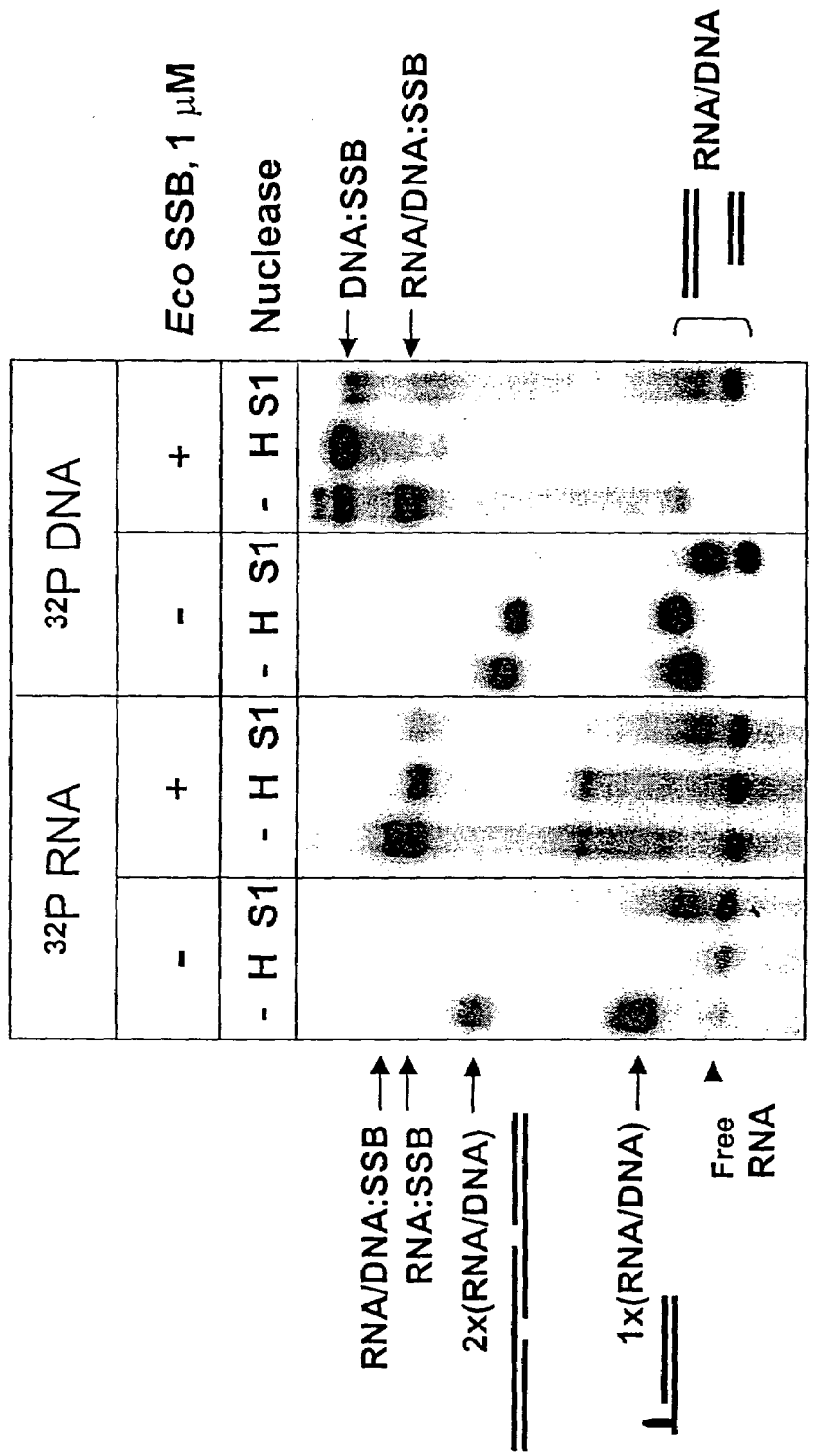
FIG. 8—Effect of EcoSSB on the state of template DNA and product RNA in vRNAP transcription. Native gel electrophoresis was carried out in the absence and in the presence of EcoSSB. Transcription was performed at an intermediate (5 nM) DNA concentration, at which only a 2-fold effect of EcoSSB is observed. Either $^{32}$P-labeled template (right panel) or labeled NTPs (left panel) were used to analyze the state of the template (right panel) or RNA product (left panel) in the absence or presence of EcoSSB.

The results of this experiment are shown in FIG. 8. Either $^{32}$P-labeled template (right panel) or labeled NTPs (left panel) were used to analyze the state of the template (right panel) or RNA product (left panel) in the absence or presence of EcoSSB. After transcription, the mixtures were split further into 3 samples: a control sample with no additions, a sample to which RNase H was added to specifically degrade RNA in RNA:DNA hybrids, and a third sample to which Nuclease S1 was added to degrade single-stranded nucleic acids. In the absence of EcoSSB, both the DNA template and the RNA product are in RNA:DNA hybrids, since the RNA product is RNase H sensitive while the DNA-containing bands show altered mobility after RNase H treatment. In the presence of EcoSSB, a significant portion of the RNA product is RNase H resistant and therefore free, although an RNase sensitive band is present that corresponds to an intermediate RNA:DNA:SSB complex. Under these conditions, the DNA is in an SSB:DNA complex. These results indicate that EcoSSB stimulates transcription through template recycling.

To define regions of EcoSSB essential for vRNAP transcription activation on single-stranded templates, the inventors have tested the effect of human mitochondrial SSB (HmtSSB), which shows extensive sequence and structural homology to EcoSSB. The N-terminus of EcoSSB contains DNA binding and tetramerization determinants while the C-terminus is involved in interaction with other replication proteins. Hmt SSB has no effect on vRNAP transcription although it does not melt the promoter hairpin. Interestingly, preliminary results using mutant EcoSSBs and EcoSSB-Hmt SSB chimeras suggest that the C-terminal region of EcoSSB is essential for vRNAP transcriptional activation.

Example 4

Characterization of mini-vRNAP Transcription Properties

Figure 9:
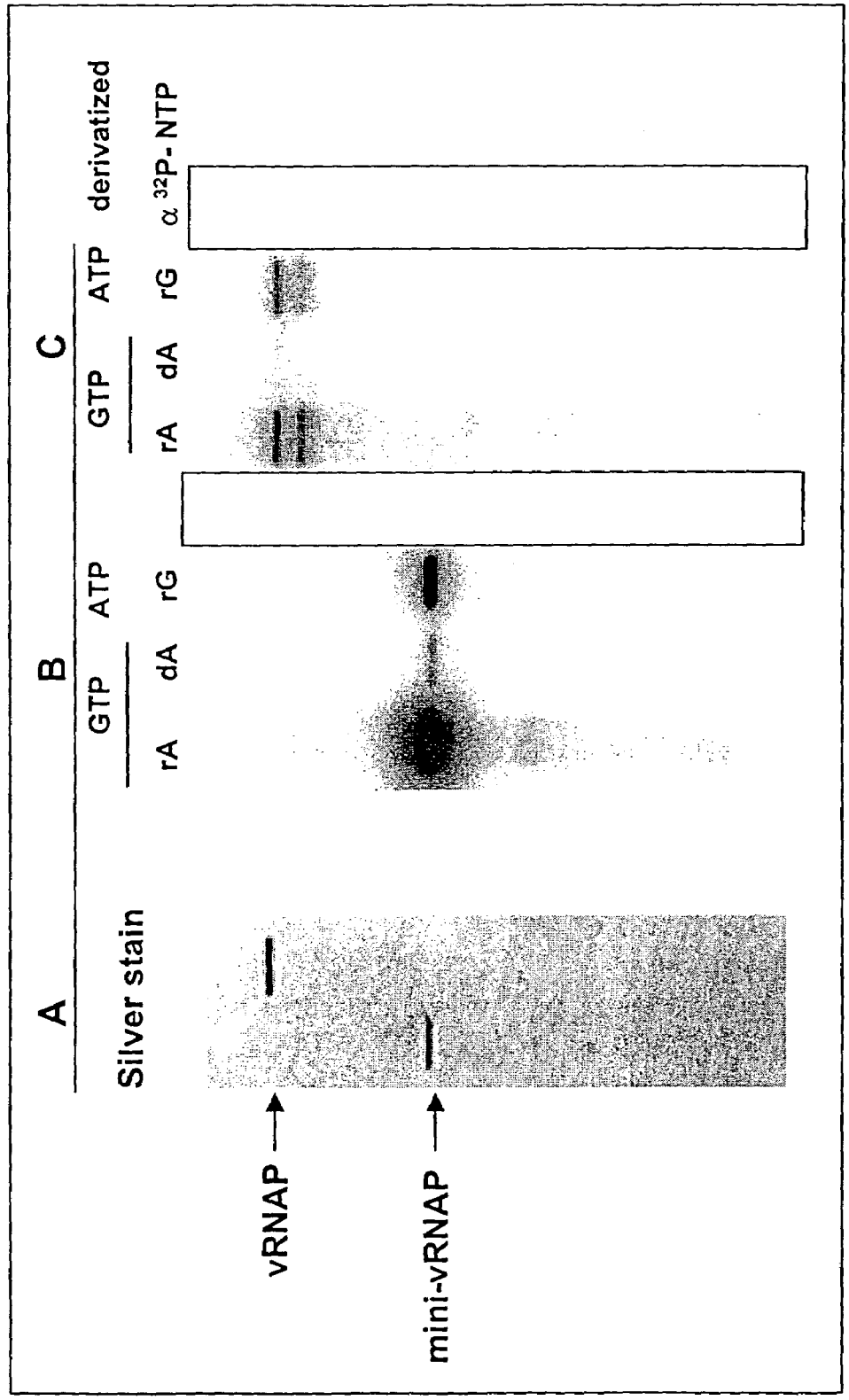
FIG. 9A, FIG. 9B, and FIG. 9C—Transcription initiation by vRNAP and mini-vRNAP. The initiation properties of the full length and mini-vRNA polymerases were compared at similar molar concentrations (FIG. 9A) using the catalytic autolabeling assay and two reaction conditions: using a template containing +1C, the benzaldehyde derivative of GTP and α$^{32}$P-ATP, or a template containing +1T, the benzaldehyde derivative of ATP and α$^{32}$P-GTP. Comparison of the results in FIGS. 9B and 9C demonstrates that mini-vRNAP exhibits initiation properties similar to full size vRNAP.

The initiation properties of the full length RNA polymerase and mini-vRNAP were compared at similar molar concentrations (FIG. 9A) using the catalytic autolabeling assay and two reaction conditions: 1- using a template containing +1C, the benzaldehyde derivative of GTP and $\alpha^{32}$P-ATP, or 2- a template containing +1T, the benzaldehyde derivative of ATP and $\alpha^{32}$P-GTP. Comparison of the results in FIGS. 9B and 9C demonstrates that mini-vRNAP exhibits initiation properties similar to full-length vRNAP. In addition, both enzymes discriminate against dATP incorporation to the same extent. Mini-vRNAP does not synthesize abortive products when the first four nucleotides of the transcript are comprised of 50% or more G or C nucleotides.

Figure 10:
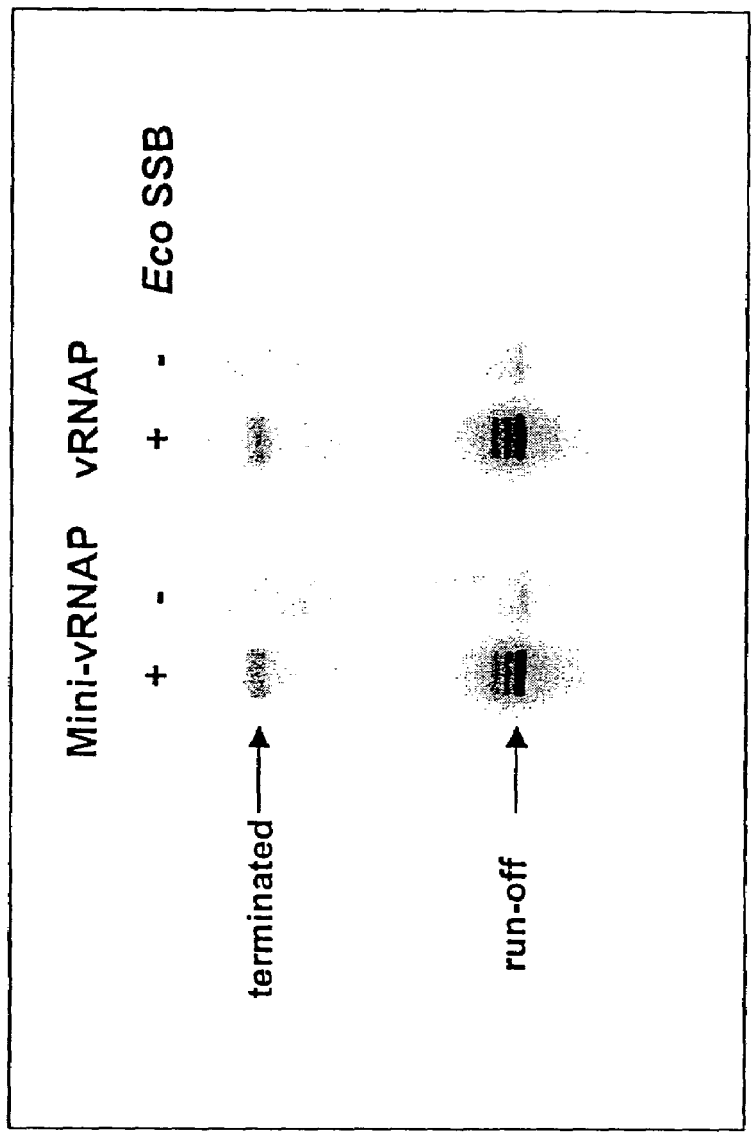
FIG. 10—Effect of EcoSSB on transcription of vRNAP and mini-vRNAP. The elongation and termination properties of vRNAP and mini-vRNAP are compared.

The elongation and termination properties of both enzymes are compared in FIG. 10. Similar run-off and terminated transcripts are synthesized. Moreover, EcoSSB activates transcription by both enzymes to the same levels. This result indicates that, if there are any sites of specific contact between vRNAP and EcoSSB, they reside in the mini-vRNAP domain.

The sequence of the terminator signals for vRNAP present in the N4 genome include SEQ ID NOS:21-26. The signals of SEQ ID NO:21 and 22 have been tested in vitro on single-stranded templates.

The rate of mini-vRNAP transcription has been compared to the rate of T7 RNA polymerase under the same conditions using the same DNA template. The template used was linearized pET11 containing the original T7 promoter and the N4 vRNAP P2 promoter that was introduced through cloning. The DNA template was denatured before performing transcription using N4 mini-vRNAP. The concentrations of T7 RNAP (Promega, Cat.#P2075) and mini-vRNAP were compared using SDS-PAGE. Transcription reactions contained 50 nM of polymerase, 100 nM of DNA template, 5× transcription buffer provided with the T7 RNAP, and 1 mM of each ATP, GTP and CTP and 0.1 mM of [$^{32}$P]- UTP (1 Ci/mmol). Each reaction mixture was split in two, and E. coli SSB was added to one half. The mixtures were incubated at 37° C. and aliquots were taken at different time points. Transcription products were electrophoresed on a 6% sequencing gel and the amount of radioactively-labeled RNA was quantitated by phosphoimaging. The results showed that: (a) transcription of T7 RNAP was not affected by the presence of E. coli SSB and (b) N4 mini-vRNAP synthesized 1.5 to 5 fold more RNA in the presence of EcoSSB than T7 RNAP at different time points of incubation.

The optimal temperature for mini-vRNAP transcription is 37° C. It exhibits 70% activity at 30° C., 65% at 45° C., and only 20% at 50° C.

The average error frequency was estimated by determining the misincorporation frequency of each of four [$^{32}$P]-α NTPs into RNA products using template ssDNAs missing the corresponding template nucleotide in the transcribed region. The following values were obtained: $\frac{1}{5} \times 10^4$ for misincorporation of G and U using "no C" (SEQ ID NO:10) and "no A" (SEQ ID NO:11) ssDNA templates, respectively; $\frac{1}{4} \times 10^4$ for misincorporation of C using the "no G" (SEQ ID NO:12) template, and $\frac{1}{2} \times 10^4$ for misincorporation of A using the "no T" (SEQ ID NO:13) template. For comparison, the average error frequency for T7 RNAP is $\frac{1}{2} \times 10^4$ (Huang, et al., 2000). Using the method for detection of mispair formation described by Huang, et al. (2000), no misincorporation by mini-vRNAP was detected.

The ability of mini-vRNAP to incorporate derivatized nucleotides was measured. Transcription by mini-vRNAP in the presence of 0.1-1 mM Digoxigenin-11-UTP (cat# 1209256, Roche), Biotin-16-UTP (cat# 1388908, Roche) or underivatized UTP, yielded comparable amounts of product RNA using "control" ssDNA (SEQ ID NO:9) as a transcription template. The product RNAs synthesized in the presence of derivatized UTP have higher molecular mass than those synthesized in the presence of underivatized UTP, and the difference corresponds to the mass difference of the UTPs used. Several derivatives (i.e. 2'Fluoro-ribonucleoside triphosphates, dideoxynucleoside triphosphates) are being tested. The fluorescent analog Fluorescein-12-UTP (Roche catalog #1427857) has been tested using a template which encodes a 51 nucleotide transcript containing a run of 4 Us, and a nucleotide mix containing ATP, CTP, GTP and Fluorescein-12-UTP only. Transcription was only 3% of that achieved with UTP, biotin-6-UTP or digoxigenin-11-UTP under the same reaction conditions. However, incorporation of the fluorescent analog at higher yields is expected to occur in the presence of underivatized UTP or on templates with other sequence compositions.

Example 5

Sequence Determinants of mini-vRNAP Promoter Binding

The three N4 early promoters present in the N4 genome contain a pair of Cs separated by 4 nucleotides from the base of the 5 bp promoter stem. In the preferred promoter P2, these 4 bases are As and the Cs are followed by a T. Preferably, mini-vRNAP uses a 17 nucleotide promoter sequence located immediately upstream of the transcription initiation site. Promoters for N4 vRNA polymerase are described by Haynes et al, (1985) and Dai et al., (1998), herein incorporated by reference. vRNAP-promoter recognition and activity require specific sequences and a hairpin structure on the template strand. The vRNAP promoters of SEQ ID NOS:27-29 assume a hairpin structure comprised of a 5-7 bp stem (the inverted repeats are underlined in Table 6) and 3 b purine-containing loop (shown in bold in Table 6). The −11 position corresponds to the center of the loop; +1 indicates the transcription start site.

TABLE 6

Promoter Sequences

| | −11        +1 | |
|---|---|---|
| P1 | 3'-CAACGAAGCGTTGAATACCT-5' | SEQ ID NO:27 |
| P2 | 3'-TTCTTCGAGGCGAAGAAAACCT-5' | SEQ ID NO:28 |
| P3 | 3'-CGACGAGGCGTCGAAAACCA-5' | SEQ ID NO:29 |

Other possible vRNAP promoters of the current invention include a set of any inverted repeats forming a hairpin with a 2-7 bp long stem and 3-5 b loop having purines in the central and/or next to the central position of the loop.

Figure 11:
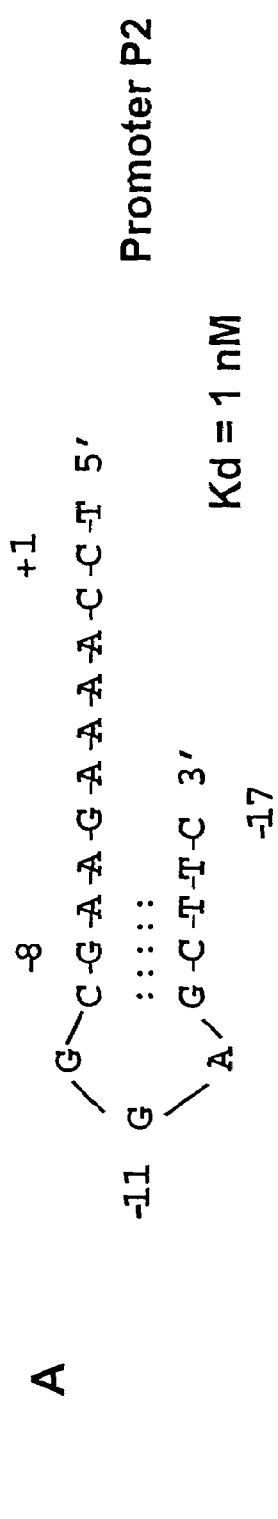
FIG. 11A and FIG. 11B—Determination of mini-vRNAP promoter contacts. A 20-base oligonucleotide containing wild type promoter P2 sequence binds with a 1 nM Kd (FIG. 11A) (nucleotides 13-32 of SEQ ID NO:16). Most oligonucleotides substituted with 5-Iodo-dU at specific positions showed close to wild type affinity except for the oligonucleotides substituted at positions −11 (at the center of the loop) and −8, indicating that these positions are essential for promoter recognition (FIG. 11B). UV crosslinking indicates that mini-vRNAP primarily contacts the −11 position.
Figure 11:
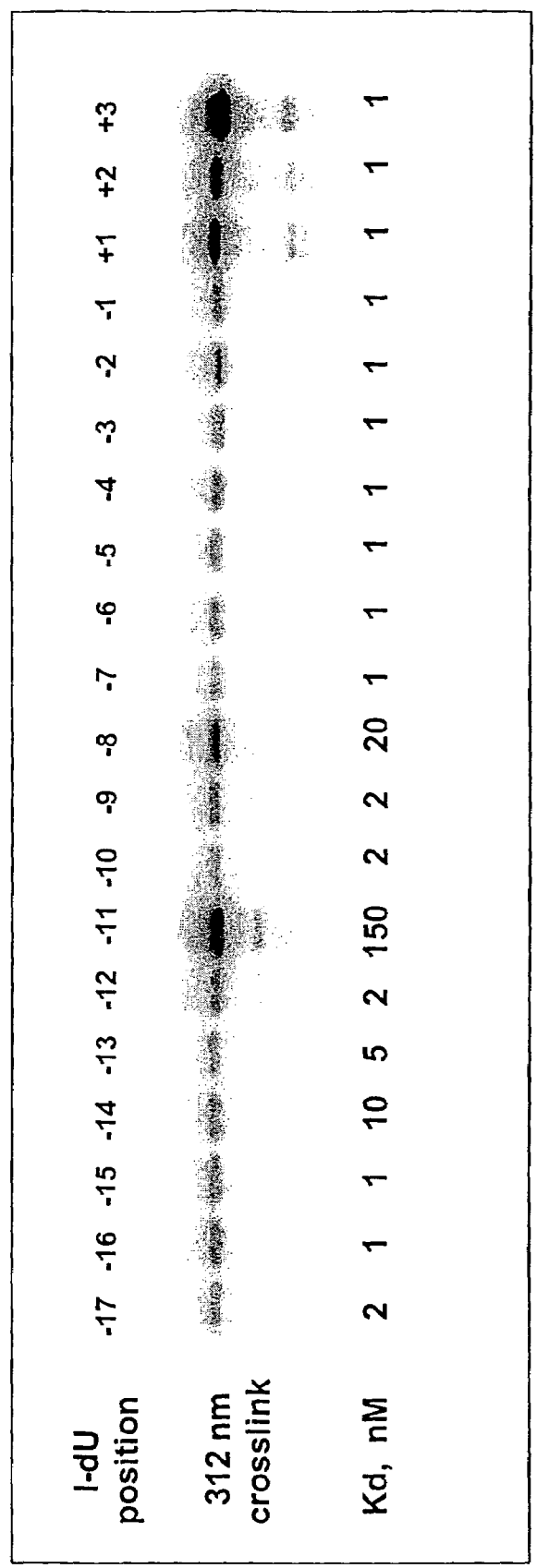

To study the sequence determinants of promoter binding, 20 base-long promoter oligonucleotides, containing the wild type vRNAP promoter P2 sequence and substituted at every position with a single 5-Iodo-dU, were used. Whenever substitutions were made in the stem, the corresponding pairing base was changed to A. These oligonucleotides were $^{32}$P end-labeled and used to determine the enzyme's affinity for promoter DNAs by a filter binding assay and the ability to crosslink to mini-vRNAP upon UV irradiation at 320 nm. A 20-base oligonucleotide with wild type promoter P2 sequence binds with a 1 nM Kd. Most oligonucleotides showed close to wild type affinity except for the oligonucleotides substituted at positions −11 (at the center of the loop) and −8, indicating that these positions are essential for promoter recognition (FIG. 11). Surprisingly, UV crosslinking was most effective at position −11, in spite of the low binding affinity, indicating a specific contact at this position to mini-vRNAP. Crosslinking was also observed to positions +1, +2 and +3, indicating non-specific contacts with this region of the template, since 5-Iodo-dU substituted oligonucleotides at these positions showed wild type binding affinity.

Figure 12:
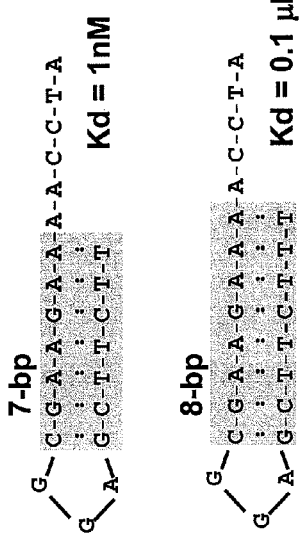
FIG. 12—Binding affinities of stem-length promoter mutants. Wild type promoter P2 with a 5 bp stem has a Kd of 1 nM (top). (nucleotides 18-37 of SEQ ID NO:17). The stem was shortened by removal of 3' bases (left). (SEQ ID NOS: 35-38). The stem can be shortened by two base pairs without change in the binding affinity. The effect of lengthening the stem by addition of 3' bases is shown (right). The stem can be lengthened by two base pairs without change in the binding affinity FIG. 13A and FIG. 13B—Identification of the transcription start site by catalytic autolabeling. A series of templates were constructed with a single C placed at different distances from the center of the hairpin (position −11) by addition or deletion of the tract of As present at promoter P2 (FIG. 13A) (nucleotides 18-37 of SEQ ID NO:17). The affinity of mini-vRNAP for these promoters was measured by filter binding, and transcription initiation was measured by catalytic autolabeling of mini-vRNAP. All templates showed similar binding affinities. However, only the template with a C positioned 12 bases downstream from the center of the hairpin was able to support transcription initiation (FIG. 13B).
Figure 12:
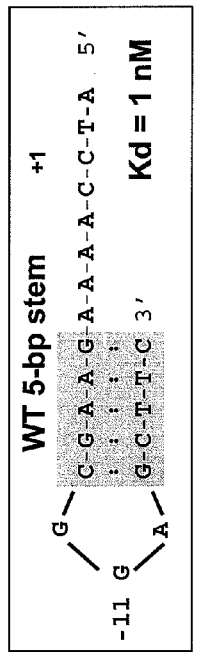
Figure 12:

The effect of changes in the stem length of the hairpin on the ability of mini-vRNAP to bind P2 promoter DNA was analyzed. As shown above, wild type promoter P2 with a 5 bp stem has a Kd of 1 nM (FIG. 12, top). The stem was shortened by removal of 3' bases as shown in FIG. 12 (left). The stem can be shortened by two base pairs without change in the binding affinity. If two or one loop-closing base pairs remain, the binding affinity of templates is still substantial (2-10 nM). This result, although surprising, is not unexpected since it has been shown that the oligonucleotide 3'd(CGAGGCG)5' forms an unusually stable minihairpin (Yoshizawa, et al., 1997). No binding is observed if one more nucleotide is removed and the loop cannot form. These results indicate that formation of a loop is essential for vRNAP-promoter recognition.

The effect of lengthening the stem by addition of 3' bases is shown in FIG. 12 (right). The stem can be lengthened by two base pairs without change in the binding affinity. On the other hand, base pairing at −2 reduces binding affinity by two orders of magnitude, with a further one order of magnitude reduction caused by base pairing at −1 and +1. These results indicate that single-strandedness of the template at positions −2, −1 and +1 is required for efficient template binding.

Figure 13:
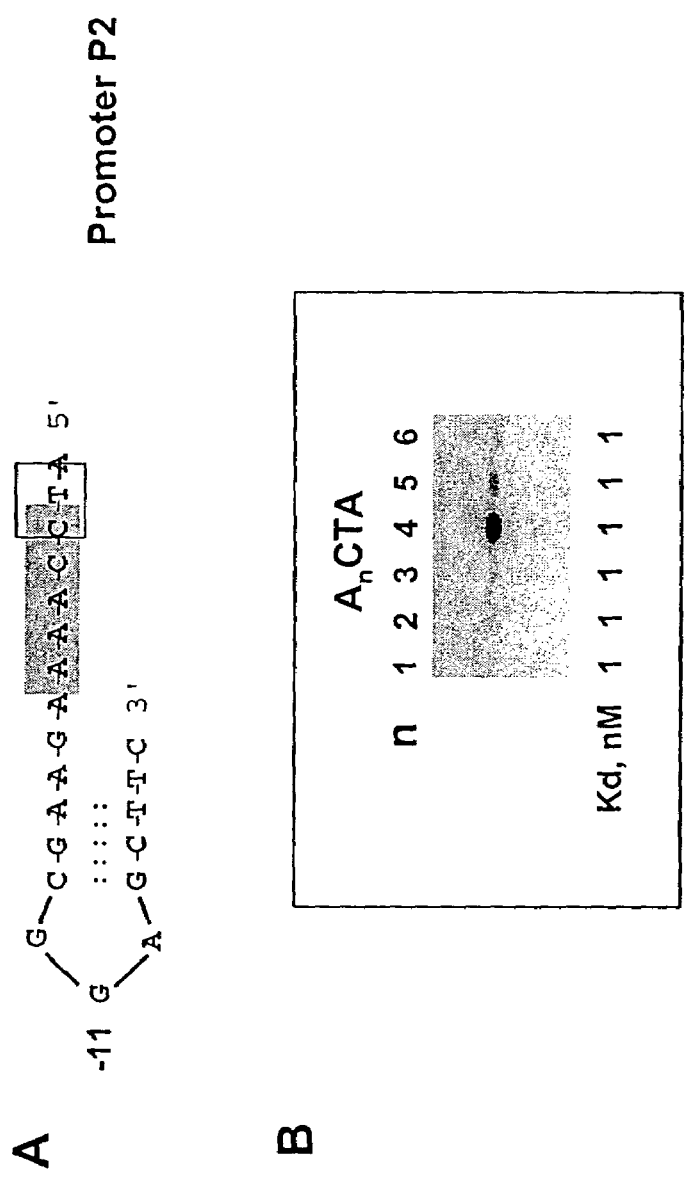

All three N4 early promoters present in the N4 genome contain a pair of Cs separated by 4 nucleotides from the base of the 5 bp promoter stem. In promoter P2, these 4 bases are As and the Cs are followed by a T. To identify the determinants of the site of transcription initiation, a series of templates were constructed with a single C placed at different distances from position −11 of the hairpin by addition or deletion of the tract of As present at promoter P2 (FIG. 13). The affinity of mini-vRNAP for these promoters was measured by filter binding and transcription initiation was measured by catalytic autolabeling of mini-vRNAP. All templates showed similar binding affinities. However, only the template with a C positioned 12 bases downstream from the center of the hairpin was able to support transcription initiation. This result indicates that mini-vRNAP utilizes this position as the transcription start site (+1).

Example 6

Identification of Sequence Motifs Essential for mini-vRNAP Activity

Figure 3:
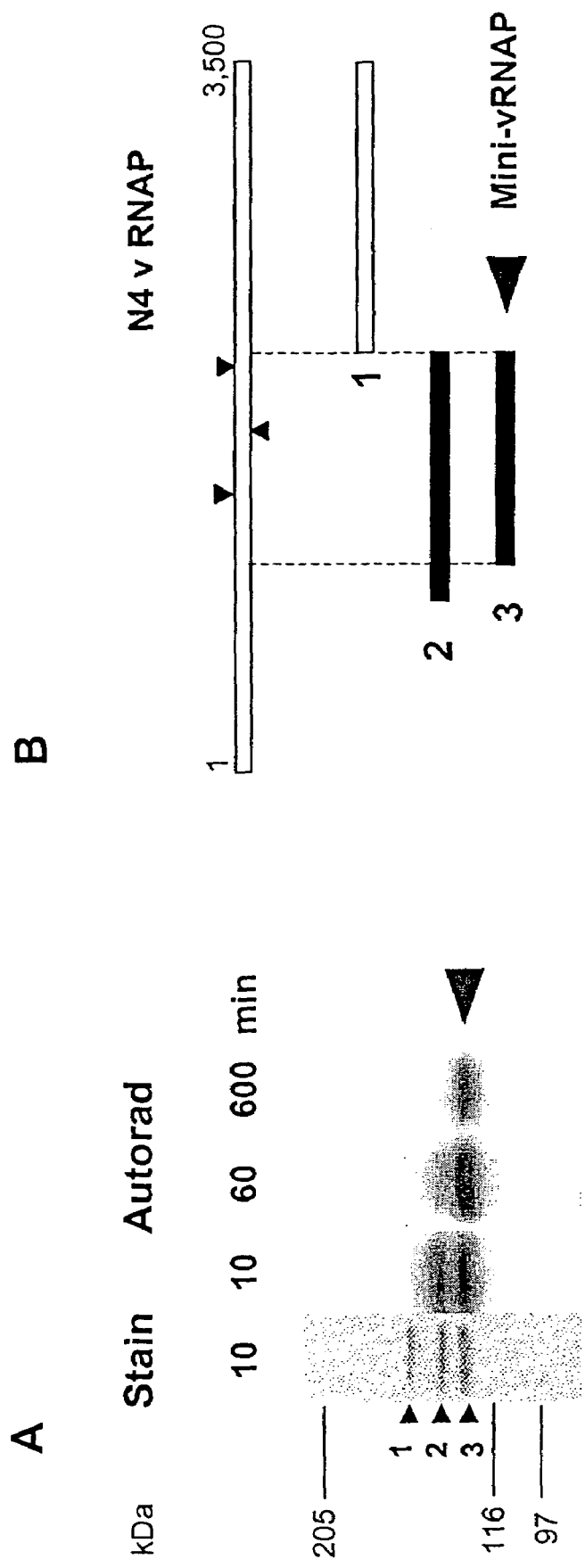
FIG. 3A and FIG. 3B—Identification of the minimal transcriptionally active domain of N4 vRNAP by proteolytic cleavage.

As shown in FIG. 2A, vRNAP contains the sequence $Rx_3Kx_6YG$, designated Motif B in the Pol I and Pol α DNA polymerases and the T7-like RNA polymerases. To determine the relevance of this motif to vRNAP activity, two mutants K670A and Y678F (SEQ ID NO:8) (position numbers in mini-vRNAP) were constructed by site-specific mutagenesis of mini-vRNAP. These two positions were chosen because, in T7-like RNA polymerases, the lysine is involved in nucleotide binding and the tyrosine in discrimination against deoxynucleoside triphosphates (Maksimova, et al., 1991 Bonner, et al., 1992; Osumi-Davis, et al., 1992). The His-tagged Y678F mini-vRNAP gene (SEQ ID NO:7) differs from that of the mini-vRNAP domain sequence (SEQ ID NO:3) at two positions: nucleotide 2033 (A) was changed to a T, and nucleotide 2034 (T) was changed to a C.

Figure 14:
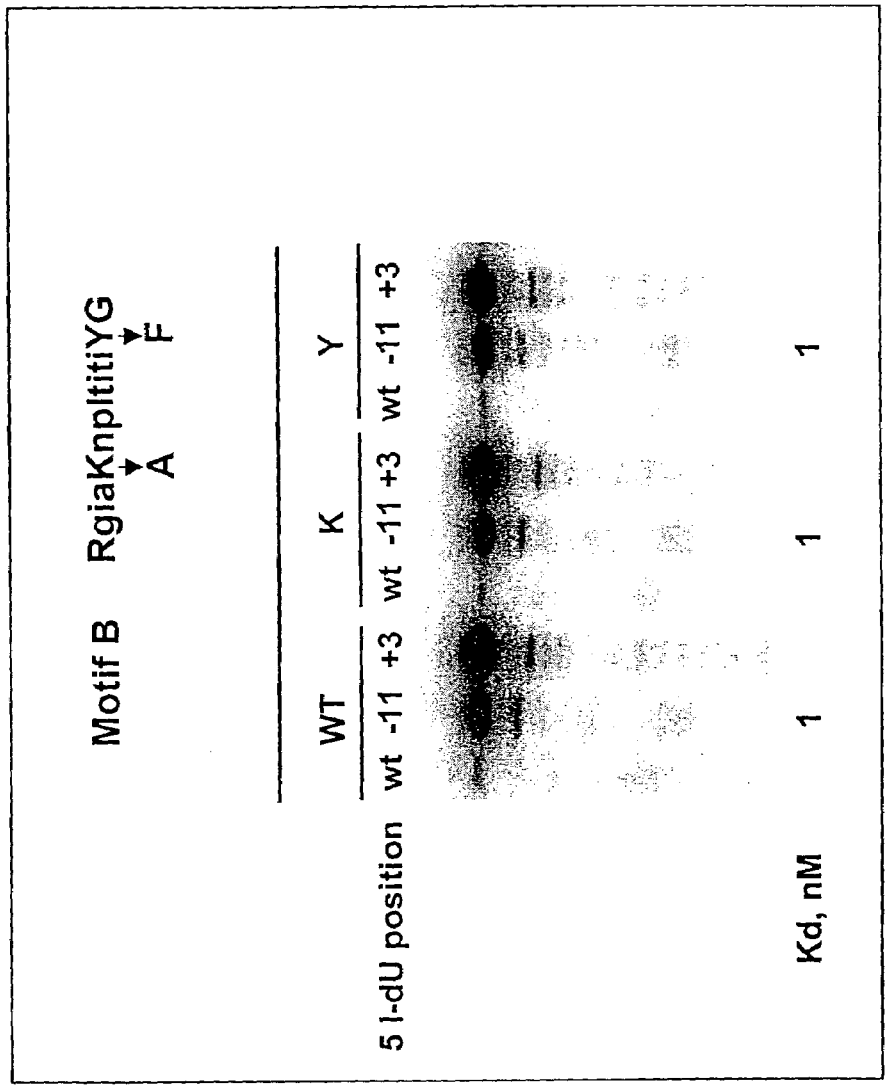
FIG. 14—UV crosslinking of mutant mini-vRNAPases to promoter oligonucleotides. Two mutants (K670A and Y678F) were tested for their ability to bind to wild type promoters. Both mutant RNA polymerases bound to promoter DNA with wild type affinities and crosslinked to 5-Iodo-dU substituted P2 DNA templates at positions −11 and +3 as well as the wild type enzyme, indicating that these polymerase mutations do not affect promoter binding.

These RNA polymerase mutants were cloned under pBAD control, purified and tested for their ability to bind to wild type promoters. Both mutant polymerases bound to promoter DNA with wild type affinities and crosslinked to 5-Iodo-dU substituted P2 DNA templates at positions −11 and +3 with wild type affinities (FIG. 14), indicating that these mutations do not affect promoter binding.

Figure 15:
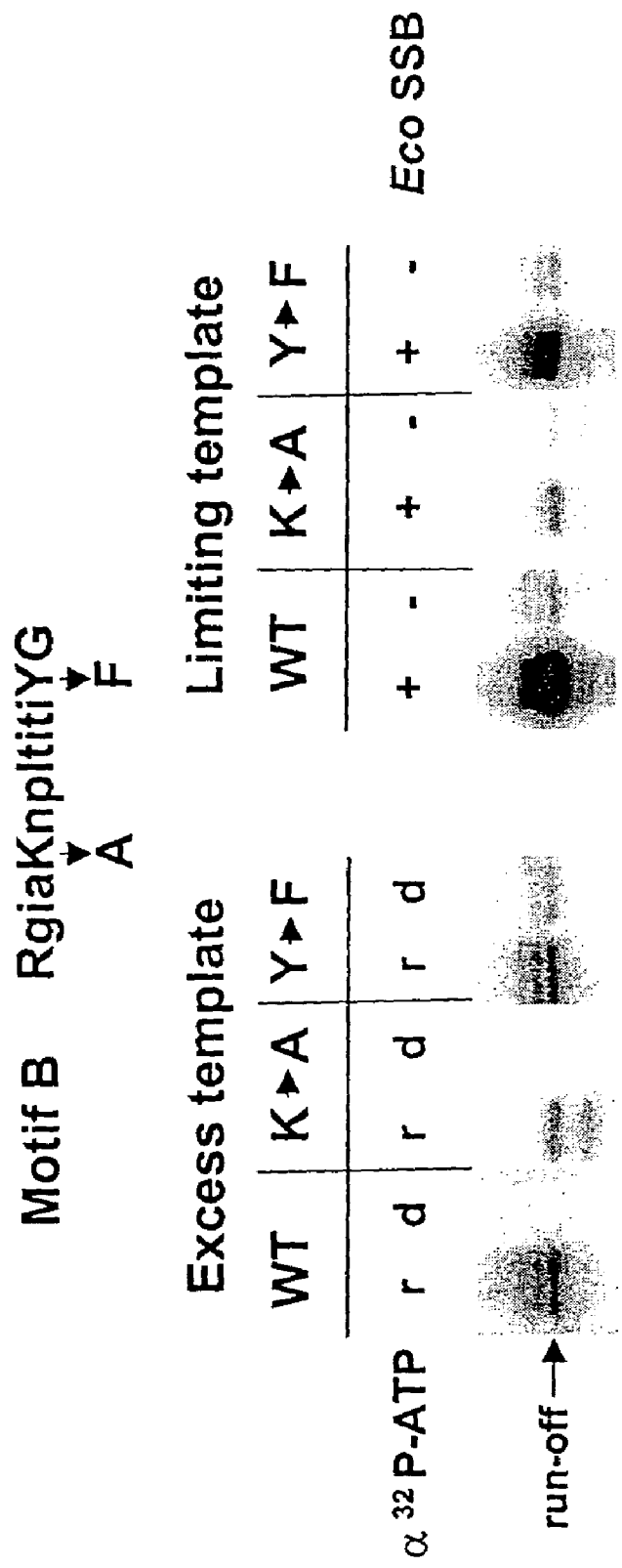
FIG. 15—Run-off transcription by mutant mini-vRNAPases. The wild type and Y678F (SEQ ID NO:8) enzymes displayed similar activities at both template excess and template-limiting conditions, while the K670A enzyme exhibited decreased activity under both conditions. Under limiting template conditions, all three enzymes were activated by EcoSSB (right panel). However, the Y678F enzyme showed reduced discrimination between incorporation of ribo- and deoxyribonucleoside triphosphates.

The mutant enzymes were tested for their ability to support run-off transcription. The wild type enzyme and Y678F enzyme (SEQ ID NO:8) displayed similar activities at both template excess and template-limiting conditions, while the K670A enzyme exhibited decreased activity under both conditions (FIG. 15). Under limiting template conditions, all three enzymes were activated by Eco SSB (right panel). However, the Y678F enzyme showed reduced discrimination between ribo- and deoxyribonucleoside triphosphates.

Figure 16:
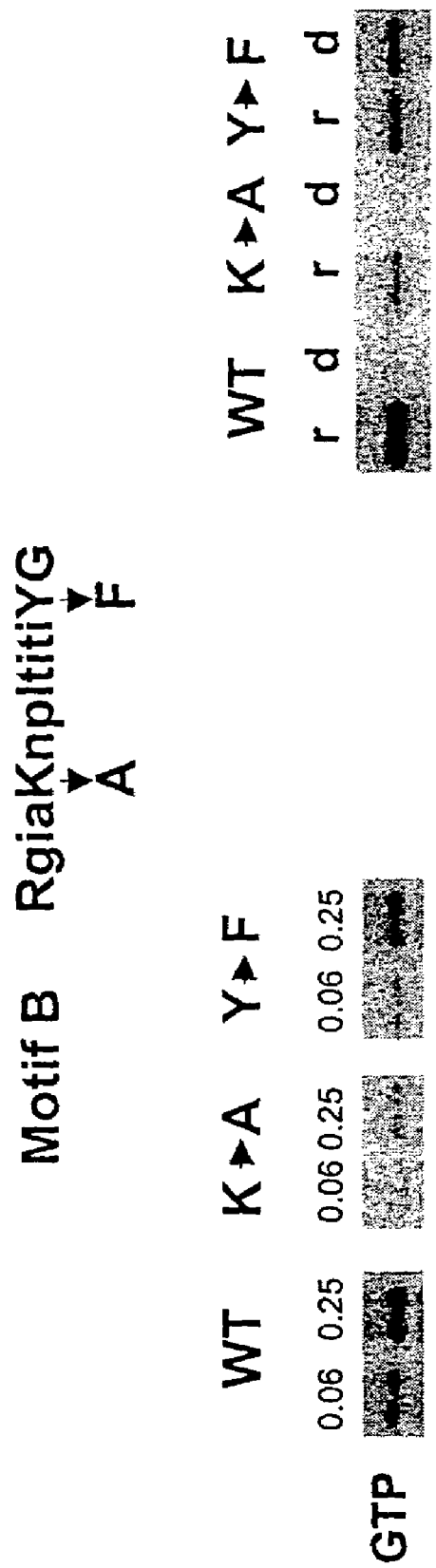
FIG. 16—Mutant mini-vRNAPases in transcription initiation. The initiation properties of the three enzymes were compared using catalytic autolabeling. The K670A enzyme displays significantly reduced activity with the GTP derivative. The Y678F enzyme, in contrast to wild type polymerase, incorporates dATP as efficiently as rATP in a single round of phosphodiester bond formation.

The initiation properties of the three enzymes were compared using catalytic autolabeling (FIG. 16). The K670A enzyme displays significantly reduced activity with the GTP derivative. The Y678F enzyme, in contrast to wild type polymerase, incorporates dATP as efficiently as rATP in a single round of phosphodiester bond formation.

Therefore, the behavior of the K670A and Y678F mutant enzymes indicates that Motif B is involved in catalysis, with the lysine probably required for NTP binding and the tyrosine responsible for dNTP discrimination. These results suggest that, despite its lack of extensive sequence similarity, vRNAP is a Class II T7-like RNA polymerase. Results of recent experiments revealed the location of the two carboxylates (aspartates) involved in catalysis.

Example 7

Figure 17:
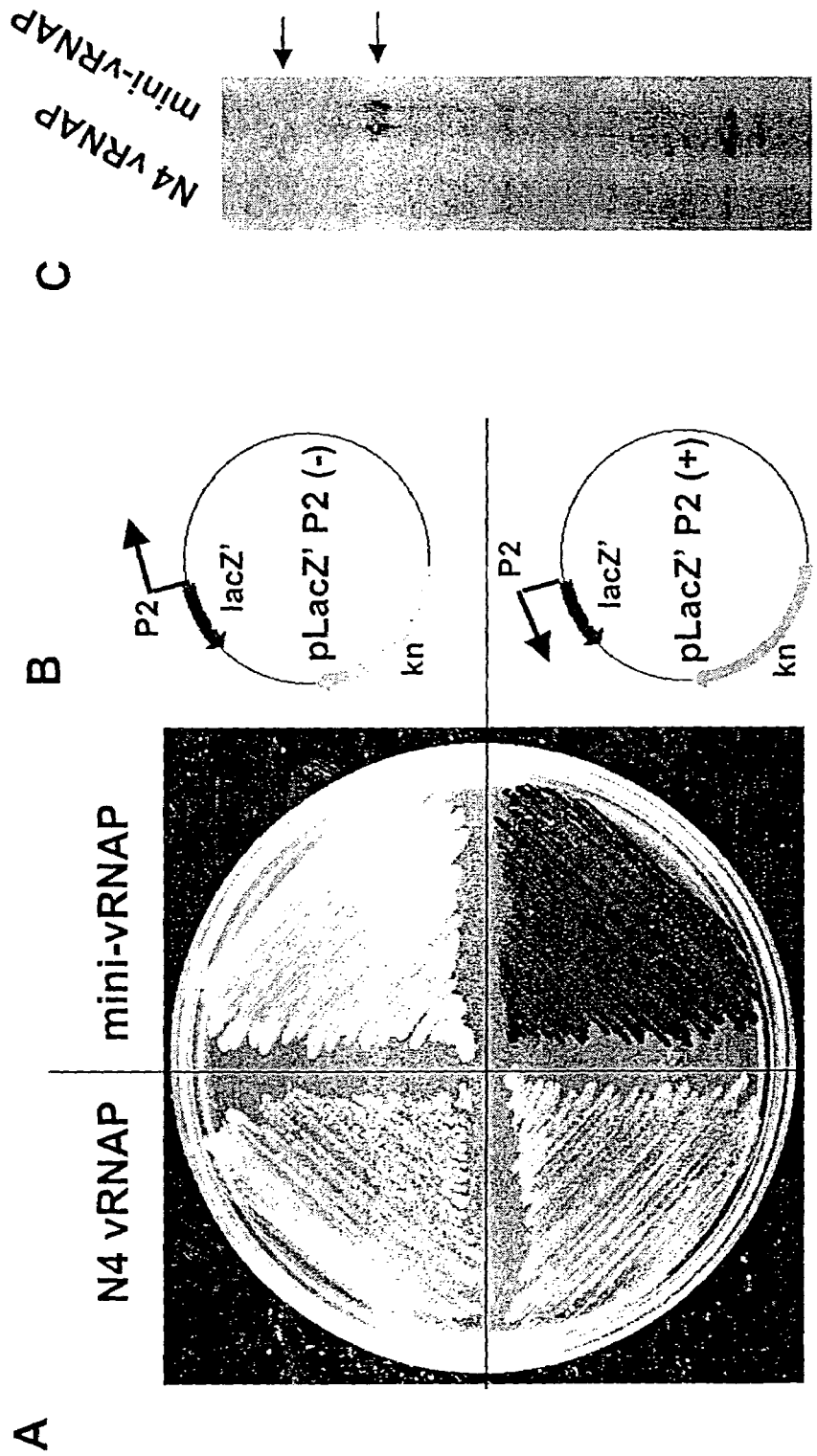
FIG. 17A, FIG. 17B, and FIG. 17C—Detection of in vivo activities of N4 vRNAP and mini-vRNAP. Transcription of β-galactosidase α-peptide by fill size and mini-vRNAP was assayed on inducing-Xgal media (FIG. 17A). Plasmid (pA-CYC) templates were constructed with a reporter gene (α-peptide of β-galactosidase) under the control of vRNAP promoter P2 cloned in either of two orientations (FIG. 17B). Induction of mini-vRNAP led to production and accumulation of detectable levels of the protein, whereas full-length vRNAP was degraded (FIG. 17C).

Development of an In Vivo System Using Mini-vRNAP and N4 vRNAP Promoters for in Vivo Expression of RNAs and Proteins Plasmid templates were constructed with a reporter gene (α-peptide of β-galactosidase) cloned under the control of vRNAP promoter P2 present in either of two orientations (FIG. 17B). The reporter construct was generated by cloning a cassette into plasmid pACYC177, which was obtained from New England Biolabs. The cassette contains an approximately 30 bp long fragment originating from pT7Ac (purchased from United States Biochemical), a N4 promoter, and sequence encoding the alpha fragment of lacZ (lacZ'). The N4 promoter and lacZ' were generated by oligonucleotide annealing and PCR™ amplification, respectively. This cassette replaces the pACY177 sequence located between the cleavage sites for restriction enzymes ApaLI and BamHI. These reporter plasmids and recombinant full-length or mini-vRNAP expressing plasmids were introduced into E. coli DH5α (ΔM15), a strain that encodes the β-galactosidase ω-peptide. Expression of the reporter gene α-peptide) in this strain results in the synthesis of active β-galactosidase and consequent production of blue colonies on X-gal plates. Transcription of α-peptide by full-length and mini-vRNAP was assayed on inducing-Xgal media and shown in FIG. 17A. Induction of full-length polymerase results in small colonies with no β-galactosidase activity. This is not surprising since full-length vRNAP is degraded in these cells (FIG. 17C). In contrast, induction of mini-vRNAP led to detectable levels of the protein (FIG. 17C) and to β-galactosidase activity only from the plasmid containing promoter P2 in the proper orientation (FIG. 17A). These results indicate that this system will be suitable for in vivo expression of RNAs and proteins under mini-N4 vRNAP promoter control.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EPA 320,308
EPA 329,822
GB 2202,328
PCT Application No. US87/00880
PCT Application No. US89/01025
U.S. Pat. No. 6,218,145
U.S. Pat. No. 4,682,195
U.S. Pat. No. 4,683,195
U.S. Pat. No. 4,683,202
U.S. Pat. No. 4,684,611
U.S. Pat. No. 4,797,368
U.S. Pat. No. 4,800,159
U.S. Pat. No. 4,883,750
U.S. Pat. No. 4,946,773
U.S. Pat. No. 4,952,500
U.S. Pat. No. 5,082,592
U.S. Pat. No. 5,139,941
U.S. Pat. No. 5,279,721
U.S. Pat. No. 5,302,523
U.S. Pat. No. 5,322,783
U.S. Pat. No. 5,354,855
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,670,488
U.S. Pat. No. 5,672,344
U.S. Pat. No. 5,693,489
U.S. Pat. No. 5,702,932
U.S. Pat. No. 5,736,524
U.S. Pat. No. 5,780,448
U.S. Pat. No. 5,789,215
U.S. Pat. No. 5,869,320
U.S. Pat. No. 5,945,100
U.S. Pat. No. 5,981,274
U.S. Pat. No. 5,994,136
U.S. Pat. No. 5,994,624
U.S. Pat. No. 5,610,287
U.S. Pat. No. 6,013,516
U.S. Pat. No. 6,046,173
WO 88/10315
WO 89/06700
WO 90/07641
WO 94/09699
WO 95/06128
Abravaya, K. and Rothman-Denes, L. B. (1990) N4 RNA polymerase II sites of transcription initiation. J. Mol. Biol. 211: 359-372.
Angel et al., Cell, 49:729, 1987b.
Angel et al., Mol. Cell. Biol., 7:2256, 1987a.

Antibodies: A Laboratory Manual, Cold Spring Harbor Laboratory, 1988

Archambault, J. and Friesen, J. D. (1993) Genetics of eukaryotic RNA polymerases I, II and III. Microbiol. Rev. 57: 703-724.

Atchison and Perry, Cell, 48:121, 1987.

Baichwal and Sugden, In: Gene Transfer, Kucherlapati R, ed., New York, Plenum Press, pp. 117-148, 1986.

Banerji et al., Cell, 27:299, 1981.

Banerji et al, Cell, 35:729, 1983.

Benvenisty and Neshif, Proc. Nat. Acad. Sci. USA, 83:9551-9555, 1986.

Berkhout et al., Cell, 59:273, 1989.

Berzal-Herranz et al., *Genes and Devel.*, 6:129-134, 1992.

Blanar et al., EMBO J., 8:1139, 1989.

Bodine and Ley, EMBO J., 6:2997, 1987.

Bonner, G., Patra, D., Lafer, E. M., and Sousa R.(1992) Mutations in T7 RNA polymerase that support the proposal for a common polymerase active site structure. EMBO J. 11: 3767-3775.

Boshart et al., Cell, 41:521, 1985.

Bosze et al., EMBO J., 5:1615, 1986.

Braddock et al., Cell, 58:269, 1989.

Bulla and Siddiqui, J. Virol., 62:1437, 1986.

Butler and Chamberlin, *J. Biol. Chem.*, 257: 5772-5778, 1982.

Campbell and Villarreal, Mol. Cell. Biol., 8:1993, 1988.

Campere and Tilghman, Genes and Dev., 3:537, 1989.

Campo et al., Nature, 303:77, 1983.

Capaldi et al., *Biochem. Biophys. Res. Comm.*, 76:425, 1977.

Carter and Flotte, Ann. N.Y. Acad. Sci., 770:79-90, 1995.

Cech et al., "In vitro splicing of the ribosomal RNA precursor of Tetrahymena: involvement of a guanosine nucleotide in the excision of the intervening sequence," *Cell*, 27:487-496, 1981.

Celander and Haseltine, J. Virology, 61:269, 1987.

Celander et al., J. Virology, 62:1314, 1988.

Cermakian, N., Ikeda, T. M., Cedergren, R., and Gray, M. W. (1996) Sequences homologous to the yeast mitochondrial and bacteriophage T3 and T7 RNA polymerases are widespread throughout the eukaryotic lineage. Nuc. Acids Res. 24: 648-654.

Chamberlin and Ryan, In: The Enzymes. San Diego, Calif., Academic Press, 15: 87-108, 1982

Chandler et al., Cell, 33:489, 1983.

Chang et al., "Foreign gene delivery and expression in hepatocytes using a hepatitis B virus vector," *Hepatology*, 14:134A, 1991.

Chang et al., Mol. Cell. Biol., 9:2153, 1989.

Chase, J. W. and Williams, K. R. (1986) Single-stranded DNA binding proteins required for DNA replication. Ann. Rev. Biochem. 55: 130-136.

Chatterjee et al., Proc. Natl. Acad. Sci. USA., 86:9114, 1989.

Cheetham, G. M. T. and Steitz, T. A. (2000) Insights into transcription: structure and function of single-subunit DNA-dependent RNA polymerases. Curr. Op. In Struc. Biol. 10: 117-123.

Cheetham, G. M., Jeruzalmi, D. and Steitz, T. A. 1999. Structural basis for initiation of transcription from an RNA polymerase-promoter complex. Nature 399: 80-83.

Chen and Okayama, Mol. Cell Biol., 7:2745-2752, 1987.

Choi et al., Cell, 53:519, 1988.

Chowrira et al., "In vitro and in vivo comparison of hammerhead, hairpin, and hepatitis delta virus self-processing ribozyme cassetyes," *J. Biol. Chem.*, 269:25856-25864, 1994.

Chowrira et al., *Biochemistry*, 32:1088-1095, 1993.

Clark, Voulgaropoulou, Fraley, and Johnson, "Cell lines for the production of recombinant adeno-associated virus," *Human Gene Therapy*, 6:1329-1341, 1995.

Coetze et al., 1994 Genes & Develop. 8, 1575.

Coffin, "Retroviridae and their replication," *In: Virology*, Fields et al. (eds.), New York: Raven Press, pp. 1437-1500, 1990.

Costa et al., Mol. Cell. Biol., 8:81, 1988.

Couch et al., "Immunization with types 4 and 7 adenovirus by selective infection of the intestinal tract," *Am. Rev. Resp. Dis.*, 88:394-403, 1963.

Cramer, P., Bushnell, D. A., and Kornberg, R. D. (2001) Structural basis of transcription: RNA polymerase II at 2.8 Å resolution Sciencexpress, www.sciencexpress.org. 19 April Cramer, P., Bushnell, D. A., Fu, J., Gnatt, A. L., Maier-Davis, B., Thompson, N. E., Burgess, R. R., Edwards, A. M., David, P. R., and Kornberg, R. D. 2000. Science 288: 640-649.

Cripe et al., EMBO J., 6:3745, 1987.

Culotta and Hamer, Mol. Cell. Biol., 9:1376, 1989.

Dai, X and Rothman-Denes, L. B. 1998. Sequence and DNA structural determinants of N4 virion RNA polymerases-promoter recognition. Genes Devepmnt. 12:2782-2790.

Dandolo et al., J. Virology, 47:55, 1983.

De Villiers et al, Nature, 312:242, 1984.

Delarue, M., Poch, O., Tordo, N., Moras, D., and Argos, P. (1990) An attempt to unify the structure of polymerases. Protein Engineering. 3: 461-467.

Deschamps et al., Science, 230:1174, 1985.

Di Chiara et al., *Trends Pharmacol Sci.*, 13:185, 1992.

Dubensky et al., Proc. Nat. Acad. Sci. USA, 81:7529-7533, 1984.

Dunn et al., *Nature New Biology*, 230: 94-96, 1971

Edbrooke et al., Mol. Cell. Biol., 9:1908, 1989.

Edlund et al., Science, 230:912, 1985.

Elliott, Hynansky, Inturrisi, "Dextromethorphan attenuates and reverses analgesic tolerance to morphine," *Pain*, 59:361-368, 1994.

Falco, S. C. and Rothman-Denes, L. B. 1979. Bacteriophage N4-induced transcribing activities in *E. coli:* I. Detection and characterization in cell extracts. Virology 95: 454-465.

Falco, S. C., Vander Laan, K., and Rothman-Denes, L. B. 1977. Virion-associated RNA polymerase required for bacteriophage N4 development. Proc. Natl. Acad.Sci. (USA) 74: 520-523.

Falco, S.C., Zehring, W. A., and Rothman-Denes, L. B. 1980. DNA-dependent RNA polymerase from bacteriophage N4 virions: purification and characterization. J. Biol. Chem. 255: 4339-4347.

Falco, S. C., Zivin, R., and Rothman-Denes, L. B. 1978. Novel template requirements of N4 virion RNA polymerase. Proc. Natl. Acad. Sci. (USA) 75: 3220-3224.

Faraldo et al., J. Bact., 174: 7458-7462, 1992

Fechheimer et al., Proc. Natl. Acad. Sci. USA, 84:8463-8467, 1987.

Feng and Holland, Nature, 334:6178, 1988.

Ferkol et al., FASEB J., 7:1081-1091, 1993.

Firak and Subramanian, Mol. Cell. Biol., 6:3667, 1986.

Foecking M K, Hofstetter H. *Gene.* 45(1):101-105, 1986.

Foley, "Opioid analgesics in clinical pain management. In: *Handbook of Experimental Pharmacology*, Herz, (Ed.), Vol. Vol. 104/II: Opioids II., Springer-Verlag, Berlin, pp. 693-743, 1993.

Forster and Symons, "Self-cleavage of plus and minus RNAs of a virusoid and a structural model for the active sites," *Cell*, 49:211-220, 1987.

Fraley et al., Proc. Natl. Acad. Sci. USA, 76:3348-3352, 1979.

Frohman, In: *PCR Protocols: A Guide To Methods And Applications,* Academic Press, N.Y., 1990.

Fujita et al., Cell, 49:357, 1987.

Gerlach et al., "Construction of a plant disease resistance gene from the satellite RNA of tobacco rinspot virus," *Nature (London),* 328:802-805, 1987.

Ghosh and Bachhawat, In: Liver diseases, targeted diagnosis and therapy using specific receptors and ligands, (Wu G, Wu C ed.), New York: Marcel Dekker, pp. 87-104, 1991.

Gilles et al., Cell, 33:717, 1983.

Gloss et al., EMBO J., 6:3735, 1987.

Glucksmann, M. A., Markiewicz, P., Malone, C., and Rothman-Denes, L. B. 1992. Specific sequences and a hairpin structure in the template strand are required for N4 virion RNA polymerase-promoter recognition. Cell 70, 491-500.

Glucksmann-Kuis, A. M., Dai, X., Markiewicz, P. M. and Rothman-Denes, L. B. 1996. E. coli SSB activation of N4 virion RNA polymerase: specific stabilization of an essential DNA hairpin required for promoter recognition. Cell 84, 147-154.

Godbout et al., Mol. Cell. Biol., 8:1169, 1988.

Gomez-Flores and Weber, "Differential effects of buprenorphine and morphine on immune and neuroendocrine functions following acute administration in the rat mesencephalon periaqueductal gray," *Immunopharm,m,* 48:145-156, 2000.

Goodbourn and Maniatis, Proc. Natl. Acad. Sci. USA, 85:1447, 1988.

Goodbourn et al., Cell, 45:601, 1986.

Gopal, Mol. Cell Biol., 5:1188-1190, 1985.

Graham and Prevec, "Adenovirus-based expression vectors and recombinant vaccines," *Biotechnology,* 20:363-390, 1992.

Graham and Prevec, "Manipulation of adenovirus vectors," In. Gene Transfer and Expression Protocols, Murray, E. J., ed., Humana, N.J., vol. 7, 109-128, 1991.

Graham and Van Der Eb, Virology, 52:456-467, 1973.

Greene et al., Immunology Today, 10:272, 1989.

Gross, C. A., Chan, C., Dombroski, A., Gruber, T., Sharp, M., Tupy, J., and Young, B. (1998) The functional and regulatory roles of sigma factors in transcription. In: Mechanisms of Transcription. Cold Spring Harbor Symp. Quant. Biol. 63: 141-156.

Grosschedl and Baltimore, Cell, 41:885, 1985.

Guzman, L. M. et al. (1995) J. Bact. 177: 4121-4130.

Hartmann et al., Nucl. Acids Res., 19: 5957-5964, 1991

Hartmann et al., Biochem, 69: 1097-1104, 1987

Hartmann, G. R., Biebricker, C., Glaser, S. J., Grosse, F., Katzameyer, M., Lindner, A. J., Mosig, H., Nasheuer, H. P., Rothman-Denes, L. B., Schaffner, A. R., Schneider, G., Stetter, K -D., and Thomm, M . 1988. Initiation of transcription—a general tool for affinity labelling of RNA polymerases by autocatalysis. Biol. Chem. Hoppe-Seyler 369: 775-788.

Haseloff and Gerlach, "Simple RNA enzymes with new and highly specific endoribonuclease activities," Nature, 334: 585-591, 1988.

Haslinger and Karin, Proc. Natl. Acad. Sci. USA., 82:8572, 1985.

Hauber and Cullen, J. Virology, 62:673, 1988.

Hausmann *Current Topics in Microbiology and Immunology,* 75: 77-109, 1976

Haynes, L. L. and Rothman-Denes, L. B. 1985. N4 virion RNA polymerase sites of transcription initiation. Cell 41: 597-605.

Hedtke, B., Borner, T., and Weihe, A. (1997) Mitochondrial and chloroplast phage-type RNA polymerases in Arabidopsis. Science. 277: 809-811.

Hen et al., Nature, 321:249, 1986.

Hensel et al., Lymphokine Res., 8:347, 1989.

Herr and Clarke, Cell, 45:461, 1986.

Higuchi, et al., *Biotechnology* 10:413-417 1992.

Hirochikaetal., J. Virol., 61:2599, 1987.

Hirsch et al., Mol. Cell. Biol., 10:1959, 1990.

Hochschild, A. and Dove, S. L. (1998) Protein-protein contacts that activate and repress prokaryotic transcription. Cell 92:597-600.

Holbrook et al., Virology, 157:211, 1987.

Horlick and Benfield, Mol. Cell. Biol., 9:2396, 1989.

Huang et al., Cell, 27:245, 1981.

Huang, J., Brieba, L. G., and Sousa, R. (2000) Misincorporation by Wild-Type and Mutant T7 RNA Polymerases: Identification of Interactions That Reduce Misincorporation Rates by Stabilizing the Catalytically Incompetent Open Conformation Biochemistry, 38: 11571-11580.

Hughes, J.; Smith, T. W; Kosterlitz, H.; Fothrgill, L.; Morgan, B. and Morris, H. Identification of two related pentapeptides from the brain with potent opiate agonist activity. *Nature* 1975, 258: 577-579.

Hwang et al., Mol. Cell. Biol., 10:585, 1990.

Imagawa et al., Cell, 51:251, 1987.

Imbra and Karin, Nature, 323:555, 1986.

Imler et al., Mol. Cell. Biol., 7:2558, 1987.

Imperiale and Nevins, Mol. Cell. Biol., 4:875, 1984.

Jakobovits et al., Mol. Cell. Biol., 8:2555, 1988.

Jameel and Siddiqui, Mol. Cell. Biol., 6:710, 1986.

Jaynes et al., Mol. Cell. Biol., 8:62, 1988.

Johnson et al., Mol. Cell. Biol., 9:3393, 1989.

Jones and Shenk, "Isolation of deletion and substitution mutants of adenovirus type 5," *Cell,* 13:181-188, 1978.

Jorgensen et al., J. Biol. Chem., 266: 645-655, 1991.

Joyce, "RNA evolution and the origins of life," *Nature,* 338: 217-244, 1989.

Kadesch and Berg, Mol. Cell. Biol., 6:2593, 1986.

Kaneda et al., Science, 243:375-378, 1989.

Karin et al., Mol. Cell. Biol., 7:606, 1987.

Kase et al., A potent inhibitor of protein kinase C from microbial origin," *J. Antibiot., (*8):1059-1065, 1986

Katinka et al., Cell, 20:393, 1980.

Katinka et al., Nature, 290:720, 1981.

Kato et al, J. Biol. Chem., 266:3361-3364, 1991.

Kawamoto et al., Mol. Cell. Biol., 8:267, 1988.

Kazmierczak, K. M.2001. PhD thesis. The University of Chicago.

Kiledjian et al., Mol. Cell. Biol., 8:145, 1988.

Kim and Cech, "Three dimensional model of the active site of the self-splicing rRNA precursor of Tetrahymena," *Proc. Natl. Acad. Sci. USA,* 84:8788-8792, 1987.

Klamut et al., Mol. Cell. Biol., 10:193, 1990.

Klein et al., Nature, 327:70-73, 1987.

Koch et al., Mol. Cell. Biol., 9:303, 1989.

Korsten et al., *J. Gen. Virol.,* 43: 57-73, 1975

Kriegler and Botchan, In: Eukaryotic Viral Vectors, Y. Gluzman, ed., Cold Spring Harbor: Cold Spring Harbor Laboratory, NY, 1982.

Kriegler and Botchan, Mol. Cell. Biol., 3:325, 1983.

Kriegler et al., Cell, 38:483, 1984a.

Kriegler et al., Cell, 53:45, 1988.

Kriegler et al., In: Cancer Cells 2/Oncogenes and Viral Genes, Van de Woude et al., eds, Cold Spring Harbor, Cold Spring Harbor Laboratory, 1984b.

Kriegler et al., In: Gene Expression, D. Hamer and M. Rosenberg, eds., New York: Alan R. Liss, 1983.

Kuhl et al., Cell, 50:1057, 1987.

Kunz et al., Nucl. Acids Res., 17:1121, 1989.

Larsen et al., Proc. Natl. Acad. Sci. USA., 83:8283, 1986.

Laspia et al., Cell, 59:283, 1989.

Latimer et al., Mol. Cell. Biol., 10:760, 1990.

Le Gal La Salle et al., "An adenovirus vector for gene transfer into neurons and glia in the brain," Science, 259:988-990, 1993.

Lee et al., Nature, 294:228, 1981.

Lee, Tomasetto, Sager, Proc. Natl. Acad. Sci. USA, 88:2825, 1991.

Levinson et al., Nature, 295:79, 1982.

Lieber and Strauss, "Selection of efficient cleavage sites in target RNAs by using a ribozyme expression library." Mol. Cell. Biol., 15: 540-551, 1995.

Lin et al., Mol. Cell. Biol., 10:850, 1990.

Luria et al., EMBO J., 6:3307, 1987.

Lusky and Botchan, Proc. Natl. Acad. Sci. USA., 83:3609, 1986.

Lusky et al., Mol. Cell. Biol., 3:1108, 1983.

Lutz et al., J. Receptor Res., 12:267, 1992.

Majors and Varmus, Proc. Natl. Acad. Sci. USA., 80:5866, 1983.

Maksimova, T. G., Mustayev, A. A., Zaychikov, E. F., Lyakhov, D. L., Tunitskaya, V. L., Akbarov, A. K., Luchin, S. V., Rechinsky, V. O., Chernov, B. K., and Kochetkov, S. N. (1991) Lys631 residue in the active site of the bacteriophage T7 RNA polymerase. Affinity labeling and site-directed mutagenesis. Eur J Biochem. 195: 841-847.

Malone, C., Spellman, S., Hyman, D., and Rothman-Denes, L. B. 1988. Cloning and generation of a genetic map of bacteriophage N4. Virology 162: 328-336.

Mann et al., "Mammalian protein serine/threonine phosphatase 2C: cDNA cloning and comparative analysis of amino acid sequences," Biochim. Biophys. Acta, 1130:100-104, 1992.

Markiewicz, P., Malone, C., Chase, J. W. and Rothman-Denes, L. B. 1992, E. coli single-stranded DNA binding (SSB) protein is a supercoiled-template dependent transcriptional activator of N4 virion RNA polymerase. Genes and Dev., 6: 2010-2019.

Martin and Coleman, Biochemistry, 26: 2690-2696, 1987

McGraw et al., Nucl. Acid. Res., 13: 6753-6766, 1985

McLaughlin, Collis, Hermonat, and Muzyczka, "Adeno-Associated Virus General Transduction Vectors: Analysis of Proviral Structures," J. Virol., 62:1963-1973, 1988.

McNeall et al., Gene, 76:81, 1989.

Michel and Westhof, "Modeling of the three-dimensional architecture of group I catalytic introns based on comparative sequence analysis," J. Mol. Biol., 216:585-610, 1990.

Miksicek et al., Cell, 46:203, 1986.

Miller, A. A., Wood, D., Ebright, R. E., and Rothman-Denes, L. B. (1997) RNA polymerase β' subunit: a target of DNA binding-independent activation. Science. 275: 1655-1657.

Miller, Curr. Top. Microbiol. Immunol., 158:1, 1992.

Miyomoto and Takemore, "Inhibition of naloxone-precipitated withdrawal jumping by i.c.v. and i.t. administration of saline in morphine-dependent mice," Life Sci., 52(13): 1129-1134, 1993b.

Miyomoto and Takemore, "Relative involvement of supraspinal and spinal mu opioid receptors in morphine dependence in mice," Life Sci., 52(12):1039-1044, 1993a.

Mohr et al., 1994 Nature 370, 147.

Mordacq and Linzer, Genes and Dev., 3:760, 1989.

Moreau et al., Nucl. Acids Res., 9:6047, 1981.

Muesing et al., Cell, 48:691, 1987.

Narita, Nartia, Mizoguchi, Tseng, "Inhibition of Protein Kinase C, but not of Protein Kinase A, blocks the development of acute antinociceptive tolerance to an intrathecally administered μ-opioid receptor agonist in the mouse," European Pharmacology, 280:R1-R3, 1995.

Ng et al., Nuc. Acids Res., 17:601, 1989.

Nicolas and Rubinstein, "Retroviral vectors," In: Vectors: A survey of molecular cloning vectors and their uses, Rodriguez and Denhardt (eds.), Stoneham: Butterworth, 494-513, 1988.

Nicolau and Sene, Biochim. Biophys. Acta, 721:185-190, 1982.

Nicolau et al., Methods Enzymol., 149:157-176, 1987.

Olson et al., Peptides, 10:1253, 1988.

Ondek et al., EMBO J., 6:1017, 1987.

Ornitz et al., Mol. Cell. Biol., 7:3466, 1987.

Osumi-Davis, P. A., de Aguilera, M. C., Woody, R. W., and Woody, A. Y. (1992) Asp537, Asp812 are essential and Lys631, His811 are catalytically significant in bacteriophage T7 RNA polymerase activity. J Mol Biol.226:37-45.

Palmiter et al., Nature, 300:611, 1982.

Palukaitis et al., "Characterization of a viroid associated with avacado sunblotch disease," Virology, 99:145-151, 1979.

Paule, M. and White, R. J. (2000) Transcription by RNA polymerases I and III. Nuc. Acids Res. 28:1283-1298.

Pech et al., Mol. Cell. Biol., 9:396, 1989.

Perales et al., Proc. Natl. Acad. Sci. 91:4086-4090, 1994.

Perez-Stable and Constantini, Mol. Cell. Biol., 10:1116, 1990.

Perriman et al., "Extended target-site specificity for a hammerhead ribozyme," Gene, 113: 157-163, 1992.

Pert and Snyder, "Opiate receptor; demonstration in nervous tissue," Science, 179:1011-1014, 1973.

Picard and Schaffner, Nature, 307:83, 1984.

Pick, Roques, Gacel, Pasternak, "Supraspinal $mu_2$ receptors mediate spinal/supraspinal morphine synergy," Eur. J Pharmacol., 220:275-277, 1992a.

Pinkert et al., Genes and Dev., 1:268, 1987.

Ponta et al., Proc. Natl. Acad. Sci. USA., 82: 1020, 1985.

Porton et al., Mol. Cell. Biol., 10:1076, 1990.

Potter et al., Proc. Nat. Acad. Sci. USA, 81:7161-7165, 1984.

Prody et al., "Autolytic processing of dimeric plant virus satellite RNA." Science, 231:1577-1580, 1986.

Puhler, G., Leffers, H., Gropp, F., Palm, P., Klenk, H. -P., Lottspeich, F., Garrett, R. A., and Zillig, W. (1989) Archaebacterial DNA-dependent RNA polymerases testify to the evolution of the eukaryotic nuclear genome. Proc. Natl. Acad. Sci. USA. 86: 4569-4573

Queen and Baltimore, Cell, 35:741, 1983.

Quinn et al., Mol. Cell. Biol., 9:4713, 1989.

Radler et al., Science, 275:810-814, 1997.

Rashtchian and Mackey, "Labeling and Detection of Nucleic Acids," in "Nonradioactive Labeling and Detection of Biomolecules," C. Kessler, Ed., Springer-Verlag, New York, 1992, pp. 70-84

Record, M. T., Reznikoff, W. S., and Schlax, P. J. (1995) E. coli RNA polymerase (E-sigma70), promoters and the kinetics of the steps of transcription initiation, In E. coli and Salmonella typhimurium: Cell and Molecular Biology 1:792-821. F. Neidhardt ed. ASM Redondo et al., Science, 247:1225, 1990.

Reinhold-Hurek and Shub, "Self-splicing introns in tRNA genes of widely divergent bacteria," *Nature*, 357:173-176, 1992.

Reisman and Rotter, Mol. Cell. Biol., 9:3571, 1989.

Remington's Pharmaceutical Sciences, 18th Ed. Mack Printing Company, 1990.

Resendez Jr. et al., Mol. Cell. Biol., 8:4579, 1988.

Ripe et al., Mol. Cell. Biol., 9:2224, 1989.

Rippe et al., Mol. Cell Biol., 10:689-695, 1990.

Rittling et al., Nucl. Acids Res., 17:1619, 1989.

Roeder, R. (1996) The role of general transcription factors in transcription by RNA polymerase II. Trends Biochem. Sci. 21: 327-335.

Rong, M., He, B., McAllister, W. T. and Durbin, R. K. (1998) Promoter specificity determinants of T7 RNA polymerase Proc. Natl. Acad. Sci. USA 95: 515-519.

Rosen et al., Cell, 41:813, 1988.

Rossi, Pasternak, Bodnar, "Synergistic brainstem interactons for morphine analgesia," *Brain Res.*, 624:171-180, 1993.

Rothman-Denes, L. B., Dai, X., Davydova, E., Carter, R., and Kazmierczak, K. 1999. Transcriptional Regulation by DNA Structural Transitions and Single-Stranded DNA Binding Proteins. 63rd Cold Spring Harbor Symp. Quant. Biol. 63: 63-73.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA,* 86:9079-9083, 1989.

Running. J. A. et al., BioTechniques 8:276-277, 1990.

Sakai et al., Genes and Dev., 2:1144, 1988.

Saldanha et al., 1993 FASEB. J. 7, 15.

Sambrook, Fritsch, Maniatis, In: Molecular Cloning: A Laboratory Manual 2 rev.ed., Cold Spring Harbor: Cold Spring Harbor Laboratory Press, 1989.

Sanders, G. M., Kassavetis, G. A., and Geiduschek, E. P. (1997) Dual targets of a transcriptional activator that tracks on DNA. EMBO Journal. 16: 3124-3132.

Sarver et al., "Ribozymes as potential anti-HIV-1 therapeutic agents," *Science,* 247:1222-1225, 1990.

Satake et al, J. Virology, 62:970, 1988.

Scanlon et al., "Ribozyme-mediated cleavages of c-fos mRNA reduce gene expression of DNA synthesis enzymes and metallothionein," *Proc Natl Acad Sci USA,* 88:10591-10595, 1991.

Schaffner et al., J. Mol. Biol., 201:81, 1988.

Searle et al., Mol. Cell. Biol., 5:1480, 1985.

Shadel, G. S. and Clayton, D. A. (1993) Mitochondrial transcription initiation, variation and conservation. J. Biol. Chem. 268: 16083-16086.

Sharma, Klee, Nirenberg, "Opiate-dependent modution of adenylate cyclase,". *Proc. Natl. Acad Sci. U.S.A.,* 74:3365-3369, 1977.

Sharp and Marciniak, Cell, 59:229, 1989.

Sharp and Yaksh, "Pain killers of the immune system," *Nature Medicine,* 3:831-832, 1997.

Shaul and Ben-Levy, EMBO J., 6:1913, 1987.

Shelling and Smith, "Targeted integration of transfected and infected adeno-associated virus vectors containing the neomycin resistance gene," *Gene Therapy,* 1:165-169, 1994.

Sherman et al., Mol. Cell. Biol., 9:50, 1989.

Simon, *Medicinal Res. Rev.,* 11:357, 1991.

Sioud et al., "Preformed ribozyme destroys tumour necrosis factor mRNA in human cells," *J Mol. Biol.,* 223:831-835, 1992.

Sleigh and Lockett, J. EMBO, 4:3831, 1985.

Sousa, R. (1996) Structural and mechanistic relationships between nucleic acid polymerases. Trends in Biochem. Sci. 21: 186-190.

Sousa, R., Chung, Y., Rose, J. P., and Wang, B. -C. (1993) Crystal strcuture of bacteriophage T7 RNA polymerase. Nature. 364: 593-599.

Spalholz et al., Cell, 42:183, 1985.

Spandau and Lee, J. Virology, 62:427, 1988.

Spandidos and Wilkie, EMBO J., 2:1193, 1983.

Stephens and Hentschel, Biochem. J., 248:1, 1987.

Stuart et al., Nature, 317:828, 1985.

Sullivan and Peterlin, Mol. Cell. Biol., 7:3315, 1987.

Swartzendruber and Lehman, J. Cell. Physiology, 85:179, 1975.

Sweetser, D., Nonet, M., and Young, R. A. (1987) Prokaryotic and eukaryotic RNA polymerases have homologous core subunits. Proc. Natl. Acad. Sci. USA. 84: 1192-1196.

Symons, "Avacado sunblotch viroid: primary sequence and proposed secondary structure." *Nucl. Acids Res.,* 9:6527-6537, 1981.

Symons, "Small catalytic RNAs." *Annu. Rev. Biochem.,* 61:641-671, 1992.

Takebe et al., Mol. Cell. Biol., 8:466, 1988.

Tavernier et al., Nature, 301:634, 1983.

Taylor and Kingston, Mol. Cell. Biol., 10: 165, 1990a.

Taylor and Kingston, Mol. Cell. Biol., 10: 176, 1990b.

Taylor et al., J. Biol. Chem., 264:15160, 1989.

Thiesen et al., J. Virology, 62:614, 1988.

Thompson et al., "Ribozymes in gene therapy." *Nature Medicine,* 1:277-278, 1995.

Top et al., "Immunization with live types 7 and 4 adenovirus vaccines. II. Antibody response and protective effect against acute respiratory disease due to adenovirus type 7," *J. Infect. Dis.,* 124:155-160, 1971.

Towle et al., *J. Biol. Chem.,* 250:1723-1733, 1975

Tronche et al., Mol. Biol. Med., 7:173, 1990.

Tronche et al., Mol. Cell. Biol., 9:4759, 1989.

Trudel and Constantini, Genes and Dev., 6:954, 1987.

Tur-Kaspaet al., Mol. Cell Biol., 6:716-718, 1986.

Tyndall et al., Nuc. Acids. Res., 9:6231, 1981.

Ueda, Miyamae, Hayashi, Watanabe, Fukushima, Sasaki, Iwamura, Misu, "Protein kinase C involvement in homologous desensitization of α-opioid receptor coupled to Gil-phosoholipase C activation in xenopus oocytes," *Journal of Neuroscience,* 15:7485-7499, 1995.

Vannice and Levinson, J. Virology, 62:1305, 1988.

Vasseur et al., Proc. Natl. Acad. Sci. USA., 77:1068, 1980.

Wagner et al., Proc. Natl. Acad. Sci. 87(9):3410-3414, 1990.

Wagner et a., Science, 260:1510-1513, 1993.

Walsh, Nienhuis, Samulski, Brown, Miller, Young, and Liu, "Phenotypic correction of Fanconi anemia in human hematopoietic cells with a recombinant adeno-associated virus vector," *J. Clin. Invest,* 94:1440-1448, 1994.

Wang and Calame, Cell, 47:241, 1986.

Wang, Johnson, Persico, Hawkins, Griffin, Uhl, "Human α opiate receptor: cDNA and genomic clones, pharmacologic characterization and chromosomal assignment," *FEBS Letters,* 338: 217-222, 1994.

Watt et al., Proc. Natl Acad. Sci., 83(2): 3166-3170, 1986.

Weber et al., Cell, 36:983, 1984.

Weinberger et al., Mol. Cell. Biol., 8:988, 1984.

Wendt et al., Eur. J. Biochem., 191: 467-472, 1990

Whistler, J. and vonZastrow, M. (1998) Proc. Natl. Acad. Sci. 95, 9914-9.

Winoto and Baltimore, Cell, 59:649, 1989.

Wong et al., Gene, 10:87-94, 1980.

Wu and Wu, Adv. Drug Delivery Rev., 12:159-167, 1993.
Wu and Wu, Biochem., 27:887-892, 1988.
Wu and Wu, J. Biol. Chem., 262:4429-4432, 1987.
Yang et al., Proc. Natl. Acad. Sci USA, 87:9568-9572, 1990.
Yang, Chen, Trempe, "Characterization of cell lines that inducibly express the adeno-associated virus Rep proteins," *J. Virol*, 68:4847-4856, 1994.
Yoshizawa, S., Kawai, G., Watanabe, K., Miura, K., and Hirao, I. (1997) GNA trinucleotide loop sequences producing extraordinarily stable DNA mini hairpins. Biochemistry 36, 4761-4767.
Yuan and Altman, "Selection of guide sequences that direct efficient cleavage of mRNA by human ribonuclease P," *Science*, 263:1269-1273, 1994.
Yuan et al., "Targeted cleavage of mRNA by human RNase P," *Proc. Natl. Acad. Sci. USA*, 89:8006-8010, 1992.
Yutzey et al., Mol. Cell. Biol., 9:1397, 1989.
Zehring, W. A. and Rothman-Denes, L. B. (1983) Purification and characterization of coliphage N4 RNA polymerase II activity from infected cell extracts. J. Biol. Chem. 258: 8074-8080.
Zhang, G., Campbell, E. A., Minakhin, L., Richter, C., Severinov, K. and Darst, S. A. (1999) Crystal structure of Thermus aquaticus core RNA polymerase at 3.3 Å resolution. Cell 98: 811-824.
Zhou and Doetsch, Proc. Nat. Acad. Sci. USA, 90: 6601-6605, 1993
Zivin, R., Zehring, W. A., and Rothman-Denes, L. B. 1981. Transcriptional map of bacteriophage N4: location and polarity of N4 RNAs. J. Mol. Biol. 152: 335-356.

What is claimed is:

1. An isolated nucleic acid comprising a region encoding a polypeptide having an amino acid sequence set forth in SEQ ID NO:2, SEQ ID NO:4, SEQ ID NO:6, SEQ ID NO:8 or SEQ ID NO:15.

2. The nucleic acid of claim 1, wherein said nucleic acid comprises the nucleic acid sequence of SEQ ID NO:1, SEQ ID NO:3, SEQ ID NO:5, SEQ ID NO:7 or SEQ ID NO:14.

3. The nucleic acid of claim 1, wherein said nucleic acid is operatively linked to a promoter.

4. The nucleic acid of claim 3, wherein said promoter is an N4 vRNAP promoter set forth in SEQ ID NO:16, SEQ ID NO:19, SEQ ID NO:27, SEQ ID NO:28 or SEQ ID NO:29.

5. The nucleic acid of claim 3, wherein said promoter is a P2 sequence set forth in SEQ ID NO:16 or SEQ ID NO:28.

6. An isolated recombinant host cell comprising a DNA segment comprising a DNA segment comprising the nucleic acid sequence of claim 1.

7. The recombinant host cell of claim 6, wherein said DNA segment is a single-stranded DNA segment.

8. The recombinant host cell of claim 6, wherein said DNA segment is a double-stranded DNA segment.

9. The recombinant host cell of claim 6, wherein said DNA segment encodes a polypeptide having an amino acid sequence set forth in SEQ ID NO:4.

10. The recombinant host cell of claim 6, wherein said DNA segment encodes a polypeptide having an amino acid sequence set forth in SEQ ID NO:6.

11. The recombinant host cell of claim 6, wherein said cell is an *E. coli* cell.

12. A recombinant vector comprising a DNA segment encoding a N4 virion RNA polymerase polypeptide under the control of a promoter, wherein the DNA segment comprises the nucleic acid sequence of claim 1.

13. An isolated polynucleotide comprising a sequence identical or completely complementary to the full length of SEQ ID NO:1.

14. An isolated polynucleotide comprising a sequence identical or completely complementary to the full length of SEQ ID NO:3.

15. The nucleic acid of claim 1, wherein said polypeptide comprises the amino acid sequence of SEQ ID NO:4.

16. An isolated nucleic acid encoding the polypeptide of SEQ ID NO:4 wherein said polypeptide has a mutation at position Y678.

17. A method of making a full-length N4 vRNAP or mini-vRNAP comprising:
  (a) expressing an isolated nucleic acid sequence encoding vRNAP, wherein said vRNAP has the amino sequence set forth in SEQ ID NO:2, SEQ ID NO:4, SEQ ID NO:6, SEQ ID NO:8 or, SEQ ID NO:15; and
  (b) purifying said vRNAP.

18. The method of claim 17, wherein said expressing occurs in a bacteria, yeast, CHO, Cos, HeLa, NIH3T3, Jurkat, 293, Saos, or PC12 host cell.

19. The method of claim 17, further comprising using a promoter appropriate for expression in the host cell line being used.

20. The method of claim 19, wherein said promoter is pBAD.

21. The method of claim 19, wherein said promoter is a promoter recognized by T7 RNA polymerase, T3 RNA polymerase or SP6 RNA polymerase.

22. The method of claim 19, wherein said promoter is a promoter recognized by T7-like RNA polymerase.

23. The method of claim 17, wherein said vRNAP has a specific recombinant sequence for use in purification.

24. The method of claim 23, wherein said vRNAP has at least one histidine, FLAG, hemaglutinin or c-myc tag.

25. The method of claim 23, wherein said vRNAP has at least one histidine tag.

26. The method of claim 24, wherein said purifying occurs in one step.

27. The method of claim 17, wherein said vRNAP does not have a tag.

* * * * *

UNITED STATES PATENT AND TRADEMARK OFFICE
CERTIFICATE OF CORRECTION

| | | |
|---|---|---|
| PATENT NO. | : 7,452,705 B2 | |
| APPLICATION NO. | : 10/153219 | |
| DATED | : November 18, 2008 | |
| INVENTOR(S) | : Krystyna M. Kazmierczak et al. | |

It is certified that error appears in the above-identified patent and that said Letters Patent is hereby corrected as shown below:

On the title page, item (56) References Cited - Other Publications, please insert:

--Paule and White, "Transcription by RNA polymerases I and III," Nuc. Acids Res., 28:1283-1298, 2000.
Roeder, "The role of general transcription factors in transcription by RNA polymerase II," Trends Biochem. Sci., 21: 327-335, 1996.
Rong et al., "Promoter specificity determinants of T7 RNA polymerase," Proc. Natl. Acad. Sci. USA, 95:515-519, 1998.
Rothman-Denes et al., "Transcriptional Regulation by DNA Structural Transitions and Single-Stranded DNA Binding Proteins," 63rd Cold Spring Harbor Symp. Quant. Biol., 63: 63-73, 1998.
Sanders et al., "Dual targets of a transcriptional activator that tracks on DNA," EMBO Journal, 16: 3124-3132, 1997.
Shadel and Clayton, "Mitochondrial transcription initiation, variation and conservation," J. Biol. Chem., 268:16083-16086, 1993.
Sousa, "Structural and mechanistic relationships between nucleic acid polymerases," Trends in Biochem. Sci., 21: 186-190, 1996.
Sousa et al., "Crystal structure of bacteriophage T7 RNA polymerase at 3.3 Å resolution," Nature, 364:593-599, 1993.
Zhang et al., "Crystal structure of Thermus aquaticus core RNA polymerase at 3.3.Å resolution," Cell, 98:811-824, 1999.--.

In column 1, lines 9-11, delete "The government may own rights in the present invention pursuant to grant number R01 A1 12575 from the National Institute of Health" and insert --This invention was made with government support under grant number R01 A1 12575 awarded by the National Institutes of Health. The government has certain rights in the invention.-- therefor.

UNITED STATES PATENT AND TRADEMARK OFFICE
CERTIFICATE OF CORRECTION

PATENT NO. : 7,452,705 B2
APPLICATION NO. : 10/153219
DATED : November 18, 2008
INVENTOR(S) : Krystyna M. Kazmierczak et al.

It is certified that error appears in the above-identified patent and that said Letters Patent is hereby corrected as shown below:

In claim 1, column 149, line 15, delete "an" and insert --the-- therefor.

In claim 2, column 149, lines 18-19, insert --sequence-- between "acid" and "comprises".

In claim 6, column 149, line 29, delete "a DNA segment comprising".

In claim 9, column 149, line 37, delete "an" and insert --the-- therefor.

In claim 10, column 149, line 40, delete "an" and insert --the-- therefor.

Signed and Sealed this

Third Day of February, 2009

JOHN DOLL
*Acting Director of the United States Patent and Trademark Office*

SEQUENCE LISTING

```
<160> NUMBER OF SEQ ID NOS: 29

<210> SEQ ID NO 1
<211> LENGTH: 10506
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
atgtcagtat ttgatagact ggctgggttc gcagacagcg taaccaatgc aaagcaagtt      60
gacgtctcta ctgcaaccgc ccagaagaaa gctgaacaag gtgtcactac tcctcttgtt     120
tctcctgatg ctgcttatca aatgcaagct gcccgtactg gtaatgttgg ggctaatgca     180
tttgaaccag ggacagtgca atcagatttc atgaatctga ccccaatgca aatcatgaat     240
aagtatgggg ttgagcaagg cttacaactt atcaatgctc gtgctgatgc agggaaccag     300
gtattcaatg attcagttac tacaagaact cctggggaag aactggggga tattgctact     360
ggtgttggcc ttggtttgt taatacccct ggggcattg gtgctcttgg ggcaggctta       420
ctcaacgatg atgcaggtgc tgttgttgct caacaattga gtaagtttaa tgatgctgtt     480
catgctaccc aaagccaggc attacaagat aaacgtaagc tctttgctgc tcgtaactta     540
atgaatgaag tagagagtga acgtcagtat caaacagata agaaagaagg cactaatgac     600
atagtagctt ccttatctaa atttggacgt gattttgtag gttcaattga gaatgctgct     660
caaactgact ctattatttc tgatgggtta gcagaagggg taggttctct attaggtgct     720
ggtcctgtat taagggggtgc atctttactg ggtaaagcag ttgttccagc aaatactctt     780
cgtagtgctg cattggctgg tgctattgat gcaggtactg gtactcagtc actggctcgt     840
attgcctcta ctgtaggtag agctgcaccg ggtatggttg gtgttggtgc aatggaagct     900
ggtggtgcat accaacaaac tgctgatgaa attatgaaga tgagtcttaa agacttagag     960
aagtctcctg tttatcagca acatattaaa gatggtatgt cccctgaaca ggctcgtcgt    1020
cagactgcat ctgaaactgg tcttactgct gctgctattc aattacctat tgctgctgca    1080
accggtcctc tggtatcccg ttttgagatg gctcctttcc gtgctggctc tttaggtgct    1140
gtaggtatga accttgcccg tgaaacagtg gaagaaggtg ttcagggtgc tacaggccaa    1200
ctggctcaga atattgcaca gcaacaaaac attgataaga accaagacct gcttaaaggt    1260
gtcggtacac aggctggttt aggtgctctt tatggctttg gttctgctgg tgttgtacag    1320
```

```
gctccggctg gtgctgctcg tttagcaggt gctgcaactg ctcctgtatt gcgtaccaca    1380
atggctggtg ttaaagctgc tggtagtgta gcaggtaagg ttgtttctcc tattaagaat    1440
actttagtag ctcgtggtga acgggttatg aagcagaatg aagaagcatc tcctgttgct    1500
gatgactatg ttgcacaggc agcacaagaa gctatggctc aagcaccaga agcagaagtt    1560
actattcgtg atgctgttga agcaactgat gctactccag aacagaaagt tgcagcacac    1620
cagtatgttt ctgacttaat gaatgctact cgttttaatc ctgaaaatta tcaggaagca    1680
ccagagcata ttcgtaatgc tgtagctggt tctactgacc aagtacaggt tattcagaag    1740
ttagcagact tagttaacac attagatgaa tctaatcctc aagcactgat ggaagctgca    1800
tcttatatgt atgatgctgt ttcagagttt gagcagttca ttaaccgtga ccctgctgca    1860
ctggatagca ttcctaaaga ttctccggct attgagttac tcaaccgtta tacgaatctg    1920
acagctaata ttcagaacac accaaaagta attggtgcac tgaatgttat taatcgaatg    1980
attaatgaat ctgctcagaa tggttctttg aatgtgactg aagaatccag tccacaggaa    2040
atgcagaacg tagcattagc tgctgaagta gcccctgaaa agctcaatcc agagtctgta    2100
aatgttgttc ttaaacatgc tgctgatggt cgtattaaac tgaataatcg ccagattgct    2160
gccctccaga atgctgctgc aatcctgaag ggggcacggg aatatgatgc agaagctgcc    2220
cgtcttggat tacgtcctca agacattgtg agtaaacaga ttaaaacgga tgagagcaga    2280
actcaggaag gacaatactc tgcgttgcaa catgcgaata ggattcggtc tgcgtataac    2340
tctggtaatt tcgagttggc ctccgcttac ctgaacgact ttatgcagtt cgcccagcac    2400
atgcagaata aggttggagc gttgaatgag catcttgtta cggggaatgc ggataagaat    2460
aagtctgtcc actaccaagc tcttactgct gacagagaat gggttcgtag ccgtaccgga    2520
ttgggggtca atccctatga cactaagtcg gttaaatttg cccagcaagt tgctcttgaa    2580
gcgaaaacgg tagcggatat tgctaatgcc ctcgcttcgg cttacccgga actgaaggtc    2640
agtcatataa aagttactcc attggattca cgtcttaacg ctcctgctgc tgaggtggtc    2700
aaggcattcc gtcaaggcaa tcgagacgtt gcttcttctc aaccgaaagc tgactccgtg    2760
aatcaggtta agaaactcc tgttacaaaa caggaaccag ttacatctac tgtacagact    2820
aagactcctg ttagtgaatc tgttaaaaca gaacctacta ctaaagagtc tagcccacag    2880
gctataaaag aacctgtgaa ccagtctgaa aaacaggatg ttaaccttac taatgaggac    2940
aacatcaagc aacctactga atctgttaaa gaaactgaaa cttctacaaa agaaagtaca    3000
gttacagaag aattaaaaga aggtattgat gctgtttacc cttcattggt aggtactgct    3060
gattctaaag cagagggtat taagaactat ttcaaattgt cctttacctt accagaagaa    3120
cagaaatccc gtactgttgg ttcagaagca cctctaaaag atgtagccca agctctgtct    3180
tctcgtgctc gttatgaact cttttactgag aaagaaactg ctaaccctgc ttttaatggg    3240
gaagttatta agcgatacaa agaactcatg gaacatgggg aaggtattgc tgatattctt    3300
cgctcccgtc tggctaagtt ccttaacact aaggatgttg gtaaacgttt tgctcaaggt    3360
acagaagcca accgttgggt aggtggtaag ttacttaaca ttgttgagca ggatggggat    3420
acctttaagt acaacgaaca attgctacag actgctgtat tagcaggtct tcaatggaga    3480
cttactgcta ccagcaatac tgctatcaaa gatgcaaaag atgttgctgc tattactggt    3540
attgaccaag ctctgctgcc agaaggttta gtagagcaat ttgatactgg tatgacactc    3600
actgaagcag ttagttccct ggctcagaaa attgagtctt actggggatt atctcgtaat    3660
```

```
ccaaatgctc cattgggcta taccaaaggc atccctacag caatggctgc tgaaattctg    3720
gctgcatttg tagagtctac tgatgttgta gagaacatcg tggatatgtc agaaattgac    3780
ccagataaca agaagactat tggtctgtac accattactg aactggattc cttcgaccca    3840
attaatagct tccctactgc tattgaagaa gctgttttag tgaatcctac agagaagatg    3900
ttctttggtg atgacattcc tcctgtagct aatactcagc ttcgtaaccc tgctgttcgt    3960
aatactccag aacagaaggc tgcattgaaa gcagagcagg ctacagagtt ctatgtacac    4020
accccaatgg ttcaattcta tgagacgtta ggtaaagacc gtattctcga actgatgggt    4080
gctggtactc tgaataaaga gttacttaat gataaccatg ctaaatctct ggaaggtaag    4140
aaccgttcag tagaggactc ttacaaccaa ctgttctccg tcattgagca ggtaagagca    4200
cagagcgaag acatctctac tgtacctatt cactatgcat acaatatgac ccgtgttggt    4260
cgtatgcaga tgttaggtaa atacaatcct caatcagcca aactggttcg tgaggccatc    4320
ttacctacta aagctacttt ggatttatcg aaccagaaca atgaagactt ctctgcattc    4380
cagttaggtc tggctcaggc attggacatt aaagtccata ctatgactcg tgaggttatg    4440
tctgacgagt tgactaaatt actggaaggt aatctgaaac cagccattga tatgatggtt    4500
gagtttaata ccactggttc cttaccagaa aacgcagttg atgttctgaa tacagcatta    4560
ggagatagga agtcattcgt agcattgatg gctcttatgg agtattcccg ttacttagta    4620
gcagaggata aatctgcatt tgtaactcca ctgtatgtag aagcagatgg tgttactaat    4680
ggtccaatca atgccatgat gctaatgaca ggcggtctgt ttactcctga ctggattcgt    4740
aatattgcca aggggggctt gttcattggt tctccaaata gaccatgaa tgagcatcgc    4800 tctactgctg acaataatga tttatatcaa gcatccacta atgctttgat ggaatcgttg    4860
ggtaagttac gtagtaacta tgcctctaat atgcctattc agtctcagat agacagtctt    4920
ctttctctga tggatttgtt tttaccggat attaatcttg gtgagaatgg tgctttagaa    4980
cttaaacgtg gtattgctaa gaacccactg actattacca tctatggttc tggtgctcgt    5040
ggtattgcag gtaagctggt tagttctgtt actgatgcca tctatgagcg tatgtctgat    5100
gtactgaaag ctcgtgctaa agacccaaat atctctgctg ctatggcaat gtttggtaag    5160
caagctgctt cagaagcaca tgctgaagaa cttcttgccc gtttcctgaa agatatggaa    5220
acactgactt ctactgttcc tgttaaacgt aaaggtgtac tggaactaca atccacaggt    5280
acaggagcca aaggaaaaat caatcctaag acctatacca ttaagggcga gcaactgaag    5340
gcacttcagg aaaatatgct gcacttcttt gtagaaccac tacgtaatgg tattactcag    5400
actgtaggtg aaagtctggt gtactctact gaacaattac agaaagctac tcagattcaa    5460
tctgtagtgc tggaagatat gttcaaacag cgagtacaag agaagctggc agagaaggct    5520
aaagacccaa catggaagaa aggtgatttc cttactcaga agaactgaa tgatattcag    5580 gcttctctga ataacttagc ccctatgatt gagactggtt ctcagacttt ctacattgct    5640
ggttcagaaa atgcagaagt agcaaatcag gtattagcta ctaaccttga tgaccgtatg    5700
cgtgtaccaa tgagtatcta tgctccagca caggccggtg tagcaggtat tccatttatg    5760
actattggta ctggtgatgg catgatgatg caaactcttt ccactatgaa aggtgcacca    5820
aagaataccc tcaaaatctt tgatggtatg aacattggtt tgaatgacat cactgatgcc    5880
agtcgtaaag ctaatgaagc tgtttacact tcttggcagg gtaaccctat taagaatgtt    5940
tatgaatcat atgctaagtt catgaagaat gtagatttca gcaagctgtc ccctgaagca    6000
ttggaagcaa ttggtaaatc tgctctggaa tatgaccaac gtgagaatgc tactgtagat    6060
```

```
gatattgcta acgctgcatc tctgattgaa cgtaacttac gtaatattgc actgggtgta    6120
gatattcgtc ataaggtgct ggataaggta atctgtcca ttgaccagat ggctgctgta    6180
ggtgctcctt atcagaacaa cggtaagatt gacctcagca atatgacccc tgaacaacag    6240
gctgatgaac tgaataaact tttccgtgaa gagttagaag cccgtaaaca aaaagtcgct    6300
aaggctaggg ctgaagtcaa agaagaaact gtttctgaaa agaaccagt gaatccagac    6360 tttggtatgg taggccgtga gcataaggca tctggtgttc gtatcctgtc tgctactgct    6420
attcgtaatc tggctaagat tagtaatctg ccatctactc aggcagctac tcttgcggag    6480
attcagaaat cactggcagc taaagactat aagattatct acggtacacc tactcaggtt    6540
gcagagtatg ctcgtcagaa gaatgttact gaattgactt ctcaggaaat ggaagaagct    6600
caggcaggta atatttatgg ctggactaac ttcgatgata agaccattta tctggttagc    6660
ccatctatgg aaaccctcat tcatgaactg gttcatgcct ctaccttcga ggaagtttat    6720
tccttctatc agggtaatga agtaagccct acttctaagc aggctattga gaaccttgaa    6780
ggtctgatgg aacagttccg ttctctggat atttccaaag attctccaga atgagagaa    6840 gcatatgctg atgctattgc aactatcgaa ggtcatttga gtaatggatt tgttgaccca    6900
gctatctcta aagctgctgc tcttaatgag tttatggctt ggggttagc taaccgtgct    6960 cttgctgcta aacagaagag aacatcttca ctggttcaaa tggtgaaaga tgtttatcag    7020
gctattaaga aattgatttg gggacgtaaa caagctcctg cattgggaga agatatgttc    7080
tccaatctgc tgtttaactc tgcaattctg atgcgtagcc aacctacaac tcaggcagta    7140
gctaaagatg gcacactgtt ccatagcaaa gcatatggta ataatgaacg tctgtctcag    7200
ttgaaccaga ctttcgataa actggtaact gattaccttc gtactgaccc agttacagaa    7260
gtagaacgtc gtggcaatgt ggctaatgca ttaatgagtg ctactcgact ggttcgtgat    7320
gttcagtctc atggcttcaa tatgactgct caggaacagt ctgtattcca gatggttact    7380
gctgcattag caactgaagc tgcgattgac ccacatgcta tggctcgtgc tcaggaactt    7440
tatacccatg taatgaaaca ccttacggta gagcatttca tggctgaccc tgatagtact    7500
aaccctgctg accgttacta tgctcaacag aaatatgaca ccatctctgg tgctaatctg    7560
gttgaagtag atgccaaagg tagaaccagt ctgttaccta cattcctggg tctggctatg    7620
gttaatgaag aactacgttc aatcattaaa gaaatgcctg tacctaaagc agataagaaa    7680
ttagggaata tatagatac tctgcttacc aatgcaggta ctcaggtaat ggaatctctg    7740
aaccgtcgta tggctggtga ccagaaagct actaatgttc aggacagtat tgatgctttg    7800
tcagaaacaa tcatggctgc tgcttttgaaa cgagagtcct tctatgatgc tgtagcaacc    7860
cctaccggta acttcattga ccgtgctaat cagtacgtaa cggatagcat tgaacggtta    7920
tctgaaactg ttattgagaa ggcagataag gtaattgcta acccttctaa tatagctgct    7980
aaaggtgttg ctcatctggc taaactgact gctgctattg catctgaaaa acagggtgaa    8040
atagtggctc agggtgttat gactgctatg aaccagggta agtatggca acctttccat    8100 gacttagtta atgacattgt tggccgtact aagactaatg ccaatgtcta tgacttaatc    8160
aaattggtta agagccagat ttctcaagac cgtcagcaat tccgtgagca tttacctaca    8220
gtcattgctg gtaagttctc tcgtaaattg actgataccg aatggtctgc aatgcatact    8280
ggtttaggta aaacagattt agctgttcta cgtgaaacta tgagcatggc tgaaattaga    8340
gatttactct cttcatccaa gaaagtgaaa gatgaaatct ctactctgga aaagagatt    8400
```

```
cagaaccaag caggtagaaa ctggaatctg gttcagaaga aatctaagca actggctcaa    8460
tacatgatta tgggggaagt aggtaataac ctccttcgta atgcccatgc tattagtcgt    8520
ttgttaggtg aacgtattac taatggtcct gtggcagatg tagctgctat tgataagctc    8580
attactttgt actctctgga attgatgaat aagtctgacc gtgaccttt t gtcagaattg   8640
gctcaatcag aagtgaaagg tatgagttc tccattgctt atatggttgg tcaacgtact     8700
gaagagatgc gtaaagctaa aggtgataac cgtactctgc tgaatcactt taaaggctat    8760
atccctgtag agaaccagca agtgtgaat t tgattattg ctgacgataa agagtttgct   8820
aagttaaata gccaatcctt tactcgtatt ggtacttatc aggggagcac tggttt ccgt   8880
actggttcta aaggttatta cttcagccca gtagctgccc gtgccccttac tctcagggt    8940
attcttcaga acgttcgtaa tactgctggt ggtgtggata ttggtactgg ctttacgtta    9000
ggcactatgg ttgctgggcg tattactgac aaaccaaccg tagagcgtat taccaaagct    9060
ctggctaaag gtgagcgtgg gcgtgaacca ctgatgccaa tttataacag caaaggtcag    9120
gtagttgctt atgaacaatc cgttgaccct aatatgttga agcacctaaa ccaagacaat    9180
cactttgcta agatggttgg tgtatggcgt ggtcgtcagg tggaagaggc taaagcacaa    9240
cgttttaatg acattctcat tgagcaatta catgctatgt atgagaaaga cattaaagac    9300
tccagtgcta ataaatctca atatgtaaac ctgttaggta aaattgatga cccagtactg    9360
gctgatgcga ttaacctgat gaacattgag actcgtcata aggccgaaga actcttcggt    9420
aaagatgagt tatgggttcg taggggatatg ctgaatgatg cacttggcta tcgtgctgca    9480
tctattggtg atgtgtggac cggtaactct cgttggtcac ctagcaccct tgatactgtt    9540
aagaagatgt tcctcggtgc attcggtaat aaggcatatc atgtagtaat gaatgctgaa    9600
ataccattc agaacttagt gaaggacgct aagacagtaa ttgttgttaa atctgttgta    9660
gtaccggcag ttaacttcct tgctaacatc taccagatga ttggacgtgg tgttcctgtt    9720
aaagatattg ctgtgaacat tcctcgtaag acgtcagaga ttaatcagta tattaaatct    9780
cgtttacgtc agattgatgc ggaagcagag ctacgtgctg ctgaaggtaa ccctaatctg    9840
gttcgtaaac ttaaaactga gattcaatct attactgata gtcatcgtcg tatgagtatc    9900
tggcctttga ttgaagcagg tgagttctct tctattgctg atgctggtat tagtcgtgat    9960
gacctgttag tagctgaagg taagattcat gagtacatgg aaaaacttgc taataaactt    10020
ccagaaaaag tacgtaatgc tggccgttac gctcttattg ctaaggacac tgctctgttc    10080
cagggtatcc agaaaacagt agagtattca gactttattg ctaaagccat catctatgat    10140
gatttagtga acgtaagaa aaaatcttct tctgaagcat taggtcaggt aactgaagag    10200
tttattaact atgacagatt gcctggtcgt ttccgtggct atatggaaag tatggtctg    10260
atgtggttct acaactttaa aattcgttcc attaaagttg ctatgagcat gattagaaac    10320
aacccagtac attctctgat tgctacagta gtacctgctc ctaccatgtt tggtaacgta    10380
ggtctaccaa ttcaggacaa catgctaacc atgctggctg aaggaagact ggattactca    10440
ttaggcttcg gacaaggatt aagagcacct acccctcaatc cttggttcaa ccttactcac    10500
taataa                                                                10506
```

<210> SEQ ID NO 2
<211> LENGTH: 3500
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

```
Met Ser Val Phe Asp Arg Leu Ala Gly Phe Ala Asp Ser Val Thr Asn
  1               5                  10                  15

Ala Lys Gln Val Asp Val Ser Thr Ala Thr Ala Gln Lys Lys Ala Glu
             20                  25                  30

Gln Gly Val Thr Thr Pro Leu Val Ser Pro Asp Ala Ala Tyr Gln Met
         35                  40                  45

Gln Ala Ala Arg Thr Gly Asn Val Gly Ala Asn Ala Phe Glu Pro Gly
     50                  55                  60

Thr Val Gln Ser Asp Phe Met Asn Leu Thr Pro Met Gln Ile Met Asn
 65                  70                  75                  80

Lys Tyr Gly Val Glu Gln Gly Leu Gln Leu Ile Asn Ala Arg Ala Asp
                 85                  90                  95

Ala Gly Asn Gln Val Phe Asn Asp Ser Val Thr Thr Arg Thr Pro Gly
            100                 105                 110

Glu Glu Leu Gly Asp Ile Ala Thr Gly Val Gly Leu Gly Phe Val Asn
        115                 120                 125

Thr Leu Gly Gly Ile Gly Ala Leu Gly Ala Gly Leu Leu Asn Asp Asp
    130                 135                 140

Ala Gly Ala Val Val Ala Gln Gln Leu Ser Lys Phe Asn Asp Ala Val
145                 150                 155                 160

His Ala Thr Gln Ser Gln Ala Leu Gln Asp Lys Arg Lys Leu Phe Ala
                165                 170                 175

Ala Arg Asn Leu Met Asn Glu Val Glu Ser Glu Arg Gln Tyr Gln Thr
            180                 185                 190

Asp Lys Lys Glu Gly Thr Asn Asp Ile Val Ala Ser Leu Ser Lys Phe
        195                 200                 205

Gly Arg Asp Phe Val Gly Ser Ile Glu Asn Ala Ala Gln Thr Asp Ser
    210                 215                 220

Ile Ile Ser Asp Gly Leu Ala Glu Gly Val Gly Ser Leu Leu Gly Ala
225                 230                 235                 240

Gly Pro Val Leu Arg Gly Ala Ser Leu Leu Gly Lys Ala Val Val Pro
                245                 250                 255

Ala Asn Thr Leu Arg Ser Ala Ala Leu Ala Gly Ala Ile Asp Ala Gly
            260                 265                 270

Thr Gly Thr Gln Ser Leu Ala Arg Ile Ala Ser Thr Val Gly Arg Ala
        275                 280                 285

Ala Pro Gly Met Val Gly Val Gly Ala Met Glu Ala Gly Gly Ala Tyr
    290                 295                 300

Gln Gln Thr Ala Asp Glu Ile Met Lys Met Ser Leu Lys Asp Leu Glu
305                 310                 315                 320

Lys Ser Pro Val Tyr Gln Gln His Ile Lys Asp Gly Met Ser Pro Glu
                325                 330                 335

Gln Ala Arg Arg Gln Thr Ala Ser Glu Thr Gly Leu Thr Ala Ala Ala
            340                 345                 350

Ile Gln Leu Pro Ile Ala Ala Ala Thr Gly Pro Leu Val Ser Arg Phe
        355                 360                 365

Glu Met Ala Pro Phe Arg Ala Gly Ser Leu Gly Ala Val Gly Met Asn
    370                 375                 380

Leu Ala Arg Glu Thr Val Glu Glu Gly Val Gln Gly Ala Thr Gly Gln
385                 390                 395                 400
```

-continued

```
Leu Ala Gln Asn Ile Ala Gln Gln Asn Ile Asp Lys Asn Gln Asp
                405                 410                 415
Leu Leu Lys Gly Val Gly Thr Gln Ala Gly Leu Gly Ala Leu Tyr Gly
                420                 425                 430
Phe Gly Ser Ala Gly Val Val Gln Ala Pro Ala Gly Ala Ala Arg Leu
                435                 440                 445
Ala Gly Ala Ala Thr Ala Pro Val Leu Arg Thr Thr Met Ala Gly Val
            450                 455                 460
Lys Ala Ala Gly Ser Val Ala Gly Lys Val Val Ser Pro Ile Lys Asn
465                 470                 475                 480
Thr Leu Val Ala Arg Gly Glu Arg Val Met Lys Gln Asn Glu Glu Ala
                485                 490                 495
Ser Pro Val Ala Asp Asp Tyr Val Ala Gln Ala Ala Gln Glu Ala Met
                500                 505                 510
Ala Gln Ala Pro Glu Ala Glu Val Thr Ile Arg Asp Ala Val Glu Ala
            515                 520                 525
Thr Asp Ala Thr Pro Glu Gln Lys Val Ala Ala His Gln Tyr Val Ser
            530                 535                 540
Asp Leu Met Asn Ala Thr Arg Phe Asn Pro Glu Asn Tyr Gln Glu Ala
545                 550                 555                 560
Pro Glu His Ile Arg Asn Ala Val Ala Gly Ser Thr Asp Gln Val Gln
                565                 570                 575
Val Ile Gln Lys Leu Ala Asp Leu Val Asn Thr Leu Asp Glu Ser Asn
                580                 585                 590
Pro Gln Ala Leu Met Glu Ala Ala Ser Tyr Met Tyr Asp Ala Val Ser
            595                 600                 605
Glu Phe Glu Gln Phe Ile Asn Arg Asp Pro Ala Ala Leu Asp Ser Ile
            610                 615                 620
Pro Lys Asp Ser Pro Ala Ile Glu Leu Leu Asn Arg Tyr Thr Asn Leu
625                 630                 635                 640
Thr Ala Asn Ile Gln Asn Thr Pro Lys Val Ile Gly Ala Leu Asn Val
                645                 650                 655
Ile Asn Arg Met Ile Asn Glu Ser Ala Gln Asn Gly Ser Leu Asn Val
                660                 665                 670
Thr Glu Glu Ser Ser Pro Gln Glu Met Gln Asn Val Ala Leu Ala Ala
            675                 680                 685
Glu Val Ala Pro Glu Lys Leu Asn Pro Glu Ser Val Asn Val Val Leu
            690                 695                 700
Lys His Ala Ala Asp Gly Arg Ile Lys Leu Asn Asn Arg Gln Ile Ala
705                 710                 715                 720
Ala Leu Gln Asn Ala Ala Ile Leu Lys Gly Ala Arg Glu Tyr Asp
                725                 730                 735
Ala Glu Ala Ala Arg Leu Gly Leu Arg Pro Gln Asp Ile Val Ser Lys
            740                 745                 750
Gln Ile Lys Thr Asp Glu Ser Arg Thr Gln Glu Gly Gln Tyr Ser Ala
            755                 760                 765
Leu Gln His Ala Asn Arg Ile Arg Ser Ala Tyr Asn Ser Gly Asn Phe
            770                 775                 780
Glu Leu Ala Ser Ala Tyr Leu Asn Asp Phe Met Gln Phe Ala Gln His
785                 790                 795                 800
Met Gln Asn Lys Val Gly Ala Leu Asn Glu His Leu Val Thr Gly Asn
                805                 810                 815
Ala Asp Lys Asn Lys Ser Val His Tyr Gln Ala Leu Thr Ala Asp Arg
```

```
                       820             825             830
Glu Trp Val Arg Ser Arg Thr Gly Leu Gly Val Asn Pro Tyr Asp Thr
            835                 840                 845
Lys Ser Val Lys Phe Ala Gln Gln Val Ala Leu Glu Ala Lys Thr Val
            850                 855                 860
Ala Asp Ile Ala Asn Ala Leu Ala Ser Ala Tyr Pro Glu Leu Lys Val
865                 870                 875                 880
Ser His Ile Lys Val Thr Pro Leu Asp Ser Arg Leu Asn Ala Pro Ala
                885                 890                 895
Ala Glu Val Val Lys Ala Phe Arg Gln Gly Asn Arg Asp Val Ala Ser
            900                 905                 910
Ser Gln Pro Lys Ala Asp Ser Val Asn Gln Val Lys Glu Thr Pro Val
            915                 920                 925
Thr Lys Gln Glu Pro Val Thr Ser Thr Val Gln Thr Lys Thr Pro Val
            930                 935                 940
Ser Glu Ser Val Lys Thr Glu Pro Thr Thr Lys Glu Ser Ser Pro Gln
945                 950                 955                 960
Ala Ile Lys Glu Pro Val Asn Gln Ser Glu Lys Gln Asp Val Asn Leu
                965                 970                 975
Thr Asn Glu Asp Asn Ile Lys Gln Pro Thr Glu Ser Val Lys Glu Thr
            980                 985                 990
Glu Thr Ser Thr Lys Glu Ser Thr Val Thr Glu Glu Leu Lys Glu Gly
            995                1000                1005
Ile Asp Ala Val Tyr Pro Ser Leu Val Gly Thr Ala Asp Ser Lys Ala
    1010                1015                1020
Glu Gly Ile Lys Asn Tyr Phe Lys Leu Ser Phe Thr Leu Pro Glu Glu
1025                1030                1035                1040
Gln Lys Ser Arg Thr Val Gly Ser Glu Ala Pro Leu Lys Asp Val Ala
                1045                1050                1055
Gln Ala Leu Ser Ser Arg Ala Arg Tyr Glu Leu Phe Thr Glu Lys Glu
            1060                1065                1070
Thr Ala Asn Pro Ala Phe Asn Gly Glu Val Ile Lys Arg Tyr Lys Glu
            1075                1080                1085
Leu Met Glu His Gly Glu Gly Ile Ala Asp Ile Leu Arg Ser Arg Leu
            1090                1095                1100
Ala Lys Phe Leu Asn Thr Lys Asp Val Gly Lys Arg Phe Ala Gln Gly
1105                1110                1115                1120
Thr Glu Ala Asn Arg Trp Val Gly Gly Lys Leu Leu Asn Ile Val Glu
                1125                1130                1135
Gln Asp Gly Asp Thr Phe Lys Tyr Asn Glu Gln Leu Leu Gln Thr Ala
            1140                1145                1150
Val Leu Ala Gly Leu Gln Trp Arg Leu Thr Ala Thr Ser Asn Thr Ala
            1155                1160                1165
Ile Lys Asp Ala Lys Asp Val Ala Ala Ile Thr Gly Ile Asp Gln Ala
    1170                1175                1180
Leu Leu Pro Glu Gly Leu Val Glu Gln Phe Asp Thr Gly Met Thr Leu
1185                1190                1195                1200
Thr Glu Ala Val Ser Ser Leu Ala Gln Lys Ile Glu Ser Tyr Trp Gly
                1205                1210                1215
Leu Ser Arg Asn Pro Asn Ala Pro Leu Gly Tyr Thr Lys Gly Ile Pro
            1220                1225                1230
Thr Ala Met Ala Ala Glu Ile Leu Ala Ala Phe Val Glu Ser Thr Asp
            1235                1240                1245
```

```
Val Val Glu Asn Ile Val Asp Met Ser Glu Ile Asp Pro Asp Asn Lys
    1250                1255                1260
Lys Thr Ile Gly Leu Tyr Thr Ile Thr Glu Leu Asp Ser Phe Asp Pro
1265                1270                1275                1280
Ile Asn Ser Phe Pro Thr Ala Ile Glu Glu Ala Val Leu Val Asn Pro
                1285                1290                1295
Thr Glu Lys Met Phe Phe Gly Asp Asp Ile Pro Pro Val Ala Asn Thr
            1300                1305                1310
Gln Leu Arg Asn Pro Ala Val Arg Asn Thr Pro Glu Gln Lys Ala Ala
        1315                1320                1325
Leu Lys Ala Glu Gln Ala Thr Glu Phe Tyr Val His Thr Pro Met Val
    1330                1335                1340
Gln Phe Tyr Glu Thr Leu Gly Lys Asp Arg Ile Leu Glu Leu Met Gly
1345                1350                1355                1360
Ala Gly Thr Leu Asn Lys Glu Leu Leu Asn Asp Asn His Ala Lys Ser
                1365                1370                1375
Leu Glu Gly Lys Asn Arg Ser Val Glu Asp Ser Tyr Asn Gln Leu Phe
            1380                1385                1390
Ser Val Ile Glu Gln Val Arg Ala Gln Ser Glu Asp Ile Ser Thr Val
        1395                1400                1405
Pro Ile His Tyr Ala Tyr Asn Met Thr Arg Val Gly Arg Met Gln Met
    1410                1415                1420
Leu Gly Lys Tyr Asn Pro Gln Ser Ala Lys Leu Val Arg Glu Ala Ile
1425                1430                1435                1440
Leu Pro Thr Lys Ala Thr Leu Asp Leu Ser Asn Gln Asn Asn Glu Asp
                1445                1450                1455
Phe Ser Ala Phe Gln Leu Gly Leu Ala Gln Ala Leu Asp Ile Lys Val
            1460                1465                1470
His Thr Met Thr Arg Glu Val Met Ser Asp Glu Leu Thr Lys Leu Leu
        1475                1480                1485
Glu Gly Asn Leu Lys Pro Ala Ile Asp Met Met Val Glu Phe Asn Thr
    1490                1495                1500
Thr Gly Ser Leu Pro Glu Asn Ala Val Asp Val Leu Asn Thr Ala Leu
1505                1510                1515                1520
Gly Asp Arg Lys Ser Phe Val Ala Leu Met Ala Leu Met Glu Tyr Ser
                1525                1530                1535
Arg Tyr Leu Val Ala Glu Asp Lys Ser Ala Phe Val Thr Pro Leu Tyr
            1540                1545                1550
Val Glu Ala Asp Gly Val Thr Asn Gly Pro Ile Asn Ala Met Met Leu
        1555                1560                1565
Met Thr Gly Gly Leu Phe Thr Pro Asp Trp Ile Arg Asn Ile Ala Lys
    1570                1575                1580
Gly Gly Leu Phe Ile Gly Ser Pro Asn Lys Thr Met Asn Glu His Arg
1585                1590                1595                1600
Ser Thr Ala Asp Asn Asn Asp Leu Tyr Gln Ala Ser Thr Asn Ala Leu
                1605                1610                1615
Met Glu Ser Leu Gly Lys Leu Arg Ser Asn Tyr Ala Ser Asn Met Pro
            1620                1625                1630
Ile Gln Ser Gln Ile Asp Ser Leu Leu Ser Leu Met Asp Leu Phe Leu
        1635                1640                1645
Pro Asp Ile Asn Leu Gly Glu Asn Gly Ala Leu Glu Leu Lys Arg Gly
    1650                1655                1660
```

-continued

```
Ile Ala Lys Asn Pro Leu Thr Ile Thr Ile Tyr Gly Ser Gly Ala Arg
1665                1670                1675                1680

Gly Ile Ala Gly Lys Leu Val Ser Ser Val Thr Asp Ala Ile Tyr Glu
            1685                1690                1695

Arg Met Ser Asp Val Leu Lys Ala Arg Ala Lys Asp Pro Asn Ile Ser
            1700                1705                1710

Ala Ala Met Ala Met Phe Gly Lys Gln Ala Ala Ser Glu Ala His Ala
        1715                1720                1725

Glu Glu Leu Leu Ala Arg Phe Leu Lys Asp Met Glu Thr Leu Thr Ser
    1730                1735                1740

Thr Val Pro Val Lys Arg Lys Gly Val Leu Glu Leu Gln Ser Thr Gly
1745                1750                1755                1760

Thr Gly Ala Lys Gly Lys Ile Asn Pro Lys Thr Tyr Thr Ile Lys Gly
            1765                1770                1775

Glu Gln Leu Lys Ala Leu Gln Glu Asn Met Leu His Phe Phe Val Glu
            1780                1785                1790

Pro Leu Arg Asn Gly Ile Thr Gln Thr Val Gly Glu Ser Leu Val Tyr
        1795                1800                1805

Ser Thr Glu Gln Leu Gln Lys Ala Thr Gln Ile Gln Ser Val Val Leu
    1810                1815                1820

Glu Asp Met Phe Lys Gln Arg Val Gln Glu Lys Leu Ala Glu Lys Ala
1825                1830                1835                1840

Lys Asp Pro Thr Trp Lys Lys Gly Asp Phe Leu Thr Gln Lys Glu Leu
            1845                1850                1855

Asn Asp Ile Gln Ala Ser Leu Asn Asn Leu Ala Pro Met Ile Glu Thr
            1860                1865                1870

Gly Ser Gln Thr Phe Tyr Ile Ala Gly Ser Glu Asn Ala Glu Val Ala
        1875                1880                1885

Asn Gln Val Leu Ala Thr Asn Leu Asp Asp Arg Met Arg Val Pro Met
    1890                1895                1900

Ser Ile Tyr Ala Pro Ala Gln Ala Gly Val Ala Gly Ile Pro Phe Met
1905                1910                1915                1920

Thr Ile Gly Thr Gly Asp Gly Met Met Met Gln Thr Leu Ser Thr Met
            1925                1930                1935

Lys Gly Ala Pro Lys Asn Thr Leu Lys Ile Phe Asp Gly Met Asn Ile
            1940                1945                1950

Gly Leu Asn Asp Ile Thr Asp Ala Ser Arg Lys Ala Asn Glu Ala Val
        1955                1960                1965

Tyr Thr Ser Trp Gln Gly Asn Pro Ile Lys Asn Val Tyr Glu Ser Tyr
    1970                1975                1980

Ala Lys Phe Met Lys Asn Val Asp Phe Ser Lys Leu Ser Pro Glu Ala
1985                1990                1995                2000

Leu Glu Ala Ile Gly Lys Ser Ala Leu Glu Tyr Asp Gln Arg Glu Asn
            2005                2010                2015

Ala Thr Val Asp Asp Ile Ala Asn Ala Ala Ser Leu Ile Glu Arg Asn
            2020                2025                2030

Leu Arg Asn Ile Ala Leu Gly Val Asp Ile Arg His Lys Val Leu Asp
        2035                2040                2045

Lys Val Asn Leu Ser Ile Asp Gln Met Ala Ala Val Gly Ala Pro Tyr
    2050                2055                2060

Gln Asn Asn Gly Lys Ile Asp Leu Ser Asn Met Thr Pro Glu Gln Gln
2065                2070                2075                2080

Ala Asp Glu Leu Asn Lys Leu Phe Arg Glu Glu Leu Glu Ala Arg Lys
```

```
                    2085                2090                2095

Gln Lys Val Ala Lys Ala Arg Ala Glu Val Lys Glu Glu Thr Val Ser
        2100                2105                2110

Glu Lys Glu Pro Val Asn Pro Asp Phe Gly Met Val Gly Arg Glu His
    2115                2120                2125

Lys Ala Ser Gly Val Arg Ile Leu Ser Ala Thr Ala Ile Arg Asn Leu
2130                2135                2140

Ala Lys Ile Ser Asn Leu Pro Ser Thr Gln Ala Ala Thr Leu Ala Glu
2145                2150                2155                2160

Ile Gln Lys Ser Leu Ala Ala Lys Asp Tyr Lys Ile Ile Tyr Gly Thr
        2165                2170                2175

Pro Thr Gln Val Ala Glu Tyr Ala Arg Gln Lys Asn Val Thr Glu Leu
    2180                2185                2190

Thr Ser Gln Glu Met Glu Glu Ala Gln Ala Gly Asn Ile Tyr Gly Trp
        2195                2200                2205

Thr Asn Phe Asp Asp Lys Thr Ile Tyr Leu Val Ser Pro Ser Met Glu
    2210                2215                2220

Thr Leu Ile His Glu Leu Val His Ala Ser Thr Phe Glu Glu Val Tyr
2225                2230                2235                2240

Ser Phe Tyr Gln Gly Asn Glu Val Ser Pro Thr Ser Lys Gln Ala Ile
        2245                2250                2255

Glu Asn Leu Glu Gly Leu Met Glu Gln Phe Arg Ser Leu Asp Ile Ser
    2260                2265                2270

Lys Asp Ser Pro Glu Met Arg Glu Ala Tyr Ala Asp Ala Ile Ala Thr
    2275                2280                2285

Ile Glu Gly His Leu Ser Asn Gly Phe Val Asp Pro Ala Ile Ser Lys
    2290                2295                2300

Ala Ala Ala Leu Asn Glu Phe Met Ala Trp Gly Leu Ala Asn Arg Ala
2305                2310                2315                2320

Leu Ala Ala Lys Gln Lys Arg Thr Ser Ser Leu Val Gln Met Val Lys
        2325                2330                2335

Asp Val Tyr Gln Ala Ile Lys Lys Leu Ile Trp Gly Arg Lys Gln Ala
        2340                2345                2350

Pro Ala Leu Gly Glu Asp Met Phe Ser Asn Leu Leu Phe Asn Ser Ala
    2355                2360                2365

Ile Leu Met Arg Ser Gln Pro Thr Thr Gln Ala Val Ala Lys Asp Gly
    2370                2375                2380

Thr Leu Phe His Ser Lys Ala Tyr Gly Asn Asn Glu Arg Leu Ser Gln
2385                2390                2395                2400

Leu Asn Gln Thr Phe Asp Lys Leu Val Thr Asp Tyr Leu Arg Thr Asp
        2405                2410                2415

Pro Val Thr Glu Val Glu Arg Arg Gly Asn Val Ala Asn Ala Leu Met
        2420                2425                2430

Ser Ala Thr Arg Leu Val Arg Asp Val Gln Ser His Gly Phe Asn Met
    2435                2440                2445

Thr Ala Gln Glu Gln Ser Val Phe Gln Met Val Thr Ala Ala Leu Ala
2450                2455                2460

Thr Glu Ala Ala Ile Asp Pro His Ala Met Ala Arg Ala Gln Glu Leu
2465                2470                2475                2480

Tyr Thr His Val Met Lys His Leu Thr Val Glu His Phe Met Ala Asp
        2485                2490                2495

Pro Asp Ser Thr Asn Pro Ala Asp Arg Tyr Tyr Ala Gln Gln Lys Tyr
    2500                2505                2510
```

```
Asp Thr Ile Ser Gly Ala Asn Leu Val Glu Val Asp Ala Lys Gly Arg
    2515                2520                2525

Thr Ser Leu Leu Pro Thr Phe Leu Gly Leu Ala Met Val Asn Glu Glu
    2530                2535                2540

Leu Arg Ser Ile Ile Lys Glu Met Pro Val Pro Lys Ala Asp Lys Lys
2545                2550                2555                2560

Leu Gly Asn Asp Ile Asp Thr Leu Leu Thr Asn Ala Gly Thr Gln Val
                2565                2570                2575

Met Glu Ser Leu Asn Arg Arg Met Ala Gly Asp Gln Lys Ala Thr Asn
            2580                2585                2590

Val Gln Asp Ser Ile Asp Ala Leu Ser Glu Thr Ile Met Ala Ala Ala
        2595                2600                2605

Leu Lys Arg Glu Ser Phe Tyr Asp Ala Val Ala Thr Pro Thr Gly Asn
    2610                2615                2620

Phe Ile Asp Arg Ala Asn Gln Tyr Val Thr Asp Ser Ile Glu Arg Leu
2625                2630                2635                2640

Ser Glu Thr Val Ile Glu Lys Ala Asp Lys Val Ile Ala Asn Pro Ser
                2645                2650                2655

Asn Ile Ala Ala Lys Gly Val Ala His Leu Ala Lys Leu Thr Ala Ala
            2660                2665                2670

Ile Ala Ser Glu Lys Gln Gly Glu Ile Val Ala Gln Gly Val Met Thr
        2675                2680                2685

Ala Met Asn Gln Gly Lys Val Trp Gln Pro Phe His Asp Leu Val Asn
    2690                2695                2700

Asp Ile Val Gly Arg Thr Lys Thr Asn Ala Asn Val Tyr Asp Leu Ile
2705                2710                2715                2720

Lys Leu Val Lys Ser Gln Ile Ser Gln Asp Arg Gln Gln Phe Arg Glu
                2725                2730                2735

His Leu Pro Thr Val Ile Ala Gly Lys Phe Ser Arg Lys Leu Thr Asp
            2740                2745                2750

Thr Glu Trp Ser Ala Met His Thr Gly Leu Gly Lys Thr Asp Leu Ala
        2755                2760                2765

Val Leu Arg Glu Thr Met Ser Met Ala Glu Ile Arg Asp Leu Leu Ser
    2770                2775                2780

Ser Ser Lys Lys Val Lys Asp Glu Ile Ser Thr Leu Glu Lys Glu Ile
2785                2790                2795                2800

Gln Asn Gln Ala Gly Arg Asn Trp Asn Leu Val Gln Lys Lys Ser Lys
                2805                2810                2815

Gln Leu Ala Gln Tyr Met Ile Met Gly Glu Val Gly Asn Asn Leu Leu
            2820                2825                2830

Arg Asn Ala His Ala Ile Ser Arg Leu Leu Gly Glu Arg Ile Thr Asn
        2835                2840                2845

Gly Pro Val Ala Asp Val Ala Ala Ile Asp Lys Leu Ile Thr Leu Tyr
    2850                2855                2860

Ser Leu Glu Leu Met Asn Lys Ser Asp Arg Asp Leu Leu Ser Glu Leu
2865                2870                2875                2880

Ala Gln Ser Glu Val Glu Gly Met Glu Phe Ser Ile Ala Tyr Met Val
                2885                2890                2895

Gly Gln Arg Thr Glu Glu Met Arg Lys Ala Lys Gly Asp Asn Arg Thr
            2900                2905                2910

Leu Leu Asn His Phe Lys Gly Tyr Ile Pro Val Glu Asn Gln Gln Gly
        2915                2920                2925
```

```
Val Asn Leu Ile Ile Ala Asp Asp Lys Glu Phe Ala Lys Leu Asn Ser
        2930                2935                2940

Gln Ser Phe Thr Arg Ile Gly Thr Tyr Gln Gly Ser Thr Gly Phe Arg
2945                2950                2955                2960

Thr Gly Ser Lys Gly Tyr Tyr Phe Ser Pro Val Ala Ala Arg Ala Pro
        2965                2970                2975

Tyr Ser Gln Gly Ile Leu Gln Asn Val Arg Asn Thr Ala Gly Gly Val
            2980                2985                2990

Asp Ile Gly Thr Gly Phe Thr Leu Gly Thr Met Val Ala Gly Arg Ile
        2995                3000                3005

Thr Asp Lys Pro Thr Val Glu Arg Ile Thr Lys Ala Leu Ala Lys Gly
    3010                3015                3020

Glu Arg Gly Arg Glu Pro Leu Met Pro Ile Tyr Asn Ser Lys Gly Gln
3025                3030                3035                3040

Val Val Ala Tyr Glu Gln Ser Val Asp Pro Asn Met Leu Lys His Leu
        3045                3050                3055

Asn Gln Asp Asn His Phe Ala Lys Met Val Gly Val Trp Arg Gly Arg
        3060                3065                3070

Gln Val Glu Glu Ala Lys Ala Gln Arg Phe Asn Asp Ile Leu Ile Glu
    3075                3080                3085

Gln Leu His Ala Met Tyr Glu Lys Asp Ile Lys Asp Ser Ser Ala Asn
        3090                3095                3100

Lys Ser Gln Tyr Val Asn Leu Leu Gly Lys Ile Asp Asp Pro Val Leu
3105                3110                3115                3120

Ala Asp Ala Ile Asn Leu Met Asn Ile Glu Thr Arg His Lys Ala Glu
        3125                3130                3135

Glu Leu Phe Gly Lys Asp Glu Leu Trp Val Arg Arg Asp Met Leu Asn
        3140                3145                3150

Asp Ala Leu Gly Tyr Arg Ala Ala Ser Ile Gly Asp Val Trp Thr Gly
        3155                3160                3165

Asn Ser Arg Trp Ser Pro Ser Thr Leu Asp Thr Val Lys Lys Met Phe
    3170                3175                3180

Leu Gly Ala Phe Gly Asn Lys Ala Tyr His Val Val Met Asn Ala Glu
3185                3190                3195                3200

Asn Thr Ile Gln Asn Leu Val Lys Asp Ala Lys Thr Val Ile Val Val
        3205                3210                3215

Lys Ser Val Val Pro Ala Val Asn Phe Leu Ala Asn Ile Tyr Gln
        3220                3225                3230

Met Ile Gly Arg Gly Val Pro Val Lys Asp Ile Ala Val Asn Ile Pro
        3235                3240                3245

Arg Lys Thr Ser Glu Ile Asn Gln Tyr Ile Lys Ser Arg Leu Arg Gln
3250                3255                3260

Ile Asp Ala Glu Ala Glu Leu Arg Ala Ala Glu Gly Asn Pro Asn Leu
3265                3270                3275                3280

Val Arg Lys Leu Lys Thr Glu Ile Gln Ser Ile Thr Asp Ser His Arg
        3285                3290                3295

Arg Met Ser Ile Trp Pro Leu Ile Glu Ala Gly Glu Phe Ser Ser Ile
            3300                3305                3310

Ala Asp Ala Gly Ile Ser Arg Asp Asp Leu Leu Val Ala Glu Gly Lys
        3315                3320                3325

Ile His Glu Tyr Met Glu Lys Leu Ala Asn Lys Leu Pro Glu Lys Val
        3330                3335                3340

Arg Asn Ala Gly Arg Tyr Ala Leu Ile Ala Lys Asp Thr Ala Leu Phe
```

|  |  |  |  |
|---|---|---|---|
| 3345 | 3350 | 3355 | 3360 |

Gln Gly Ile Gln Lys Thr Val Glu Tyr Ser Asp Phe Ile Ala Lys Ala
            3365                3370                3375

Ile Ile Tyr Asp Asp Leu Val Lys Arg Lys Lys Lys Ser Ser Ser Glu
        3380                3385                3390

Ala Leu Gly Gln Val Thr Glu Glu Phe Ile Asn Tyr Asp Arg Leu Pro
    3395                3400                3405

Gly Arg Phe Arg Gly Tyr Met Glu Ser Met Gly Leu Met Trp Phe Tyr
    3410                3415                3420

Asn Phe Lys Ile Arg Ser Ile Lys Val Ala Met Ser Met Ile Arg Asn
3425                3430                3435                3440

Asn Pro Val His Ser Leu Ile Ala Thr Val Val Pro Ala Pro Thr Met
            3445                3450                3455

Phe Gly Asn Val Gly Leu Pro Ile Gln Asp Asn Met Leu Thr Met Leu
            3460                3465                3470

Ala Glu Gly Arg Leu Asp Tyr Ser Leu Gly Phe Gly Gln Gly Leu Arg
    3475                3480                3485

Ala Pro Thr Leu Asn Pro Trp Phe Asn Leu Thr His
  3490                3495                3500

<210> SEQ ID NO 3
<211> LENGTH: 3318
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3

| | |
|---|---|
| gaaagtacag ttacagaaga attaaaagaa ggtattgatg ctgtttaccc ttcattggta | 60 |
| ggtactgctg attctaaagc agagggtatt aagaactatt tcaaattgtc ctttaccttg | 120 |
| ccagaagaac agaaatcccg tactgttggt tcagaagcac ctctaaaaga tgtagcccaa | 180 |
| gctctgtctt ctcgtgctcg ttatgaactc tttactgaga agaaactgc taaccctgct | 240 |
| tttaatgggg aagttattaa gcgatacaaa gaactcatgg aacatgggga aggtattgct | 300 |
| gatattcttc gctcccgtct ggctaagttc cttaacacta aggatgttgg taaacgtttt | 360 |
| gctcaaggta cagaagccaa ccgttgggta ggtggtaagt tacttaacat tgttgagcag | 420 |
| gatgggata cctttaagta caacgaacaa ttgctacaga ctgctgtatt agcaggtctt | 480 |
| caatggagac ttactgctac cagcaatact gctatcaaag atgcaaaaga tgttgctgct | 540 |
| attactggta ttgaccaagc tctgctgcca gaaggtttag tagagcaatt tgatactggt | 600 |
| atgacactca ctgaagcagt tagttccctg gctcagaaaa ttgagtctta ctggggatta | 660 |
| tctcgtaatc caaatgctcc attgggctat accaaaggca tccctacagc aatggctgct | 720 |
| gaaattctgg ctgcatttgt agagtctact gatgttgtag agaacatcgt ggatatgtca | 780 |
| gaaattgacc cagataacaa gaagactatt ggtctgtaca ccattactga actggattcc | 840 |
| ttcgacccaa ttaatagctt ccctactgct attgaagaag ctgttttagt gaatcctaca | 900 |
| gagaagatgt tctttggtga tgacattcct cctgtagcta atactcagct tcgtaaccct | 960 |
| gctgttcgta atactccaga acagaaggct gcattgaaag cagagcaggc tacagagttc | 1020 |
| tatgtacaca ccccaatggt tcaattctat gagacgttag gtaaagaccg tattctcgaa | 1080 |
| ctgatgggtg ctggtactct gaataaagag ttacttaatg ataaccatgc taaatctctg | 1140 |
| gaaggtaaga accgttcagt agaggactct tacaaccaac tgttctccgt cattgagcag | 1200 |

```
gtaagagcac agagcgaaga catctctact gtacctattc actatgcata caatatgacc    1260
cgtgttggtc gtatgcagat gttaggtaaa tacaatcctc aatcagccaa actggttcgt    1320
gaggccatct tacctactaa agctactttg gatttatcga accagaacaa tgaagacttc    1380
tctgcattcc agttaggtct ggctcaggca ttggacatta aagtccatac tatgactcgt    1440
gaggttatgt ctgacgagtt gactaaatta ctggaaggta atctgaaacc agccattgat    1500
atgatggttg agtttaatac cactggttcc ttaccagaaa acgcagttga tgttctgaat    1560
acagcattag gagataggaa gtcattcgta gcattgatgg ctcttatgga gtattcccgt    1620
tacttagtag cagaggataa atctgcattt gtaactccac tgtatgtaga agcagatggt    1680
gttactaatg gtccaatcaa tgccatgatg ctaatgacag gcggtctgtt tactcctgac    1740
tggattcgta atattgccaa aggggcttg ttcattggtt ctccaaataa gaccatgaat    1800
gagcatcgct ctactgctga caataatgat ttatatcaag catccactaa tgctttgatg    1860
gaatcgttgg gtaagttacg tagtaactat gcctctaata tgcctattca gtctcagata    1920
gacagtcttc tttctctgat ggatttgttt ttaccggata ttaatcttgg tgagaatggt    1980
gctttagaac ttaaacgtgg tattgctaag aacccactga ctattaccat ctatggttct    2040
ggtgctcgtg gtattgcagg taagctggtt agttctgtta ctgatgccat ctatgagcgt    2100
atgtctgatg tactgaaagc tcgtgctaaa gacccaaata tctctgctgc tatggcaatg    2160
tttggtaagc aagctgcttc agaagcacat gctgaagaac ttcttgcccg tttcctgaaa    2220 gatatgaaa cactgacttc tactgttcct gttaaacgta aaggtgtact ggaactacaa    2280
tccacaggta caggagccaa aggaaaaatc aatcctaaga cctataccat taagggcgag    2340
caactgaagg cacttcagga aaatatgctg cacttctttg tagaaccact acgtaatggt    2400
attactcaga ctgtaggtga aagtctggtg tactctactg aacaattaca gaaagctact    2460
cagattcaat ctgtagtgct ggaagatatg ttcaaacagc gagtacaaga gaagctggca    2520
gagaaggcta agacccaac atggaagaaa ggtgatttcc ttactcagaa agaactgaat    2580
gatattcagg cttctctgaa taacttagcc cctatgattg agactggttc tcagactttc    2640
tacattgctg gttcagaaaa tgcagaagta gcaaatcagg tattagctac taaccttgat    2700
gaccgtatgc gtgtaccaat gagtatctat gctccagcac aggccggtgt agcaggtatt    2760
ccatttatga ctattggtac tggtgatggc atgatgatgc aaactctttc cactatgaaa    2820
ggtgcaccaa gaatacccct caaaatcttt gatggtatga acattggttt gaatgacatc    2880
actgatgcca gtcgtaaagc taatgaagct gtttacactt cttggcaggg taaccctatt    2940
aagaatgttt atgaatcata tgctaagttc atgaagaatg tagatttcag caagctgtcc    3000
cctgaagcat tggaagcaat tggtaaatct gctctggaat atgaccaacg tgagaatgct    3060
actgtagatg atattgctaa cgctgcatct ctgattgaac gtaacttacg taatattgca    3120
ctgggtgtag atattcgtca taaggtgctg gataaggtaa atctgtccat tgaccagatg    3180
gctgctgtag gtgctccta tcagaacaac ggtaagattg acctcagcaa tatgacccct    3240
gaacaacagg ctgatgaact gaataaactt ttccgtgaag agttagaagc ccgtaaacaa    3300
aaagtcgcta aggctagg                                                 3318
```

<210> SEQ ID NO 4
<211> LENGTH: 1107
<212> TYPE: PRT
<213> ORGANISM: Artificial Sequence
<220> FEATURE:

<223> OTHER INFORMATION: Description of Artificial Sequence: Synthetic Peptide

<400> SEQUENCE: 4

```
Met Glu Ser Thr Val Thr Glu Glu Leu Lys Glu Gly Ile Asp Ala Val
 1               5                  10                  15

Tyr Pro Ser Leu Val Gly Thr Ala Asp Ser Lys Ala Glu Gly Ile Lys
                20                  25                  30

Asn Tyr Phe Lys Leu Ser Phe Thr Leu Pro Glu Glu Gln Lys Ser Arg
            35                  40                  45

Thr Val Gly Ser Glu Ala Pro Leu Lys Asp Val Ala Gln Ala Leu Ser
     50                  55                  60

Ser Arg Ala Arg Tyr Glu Leu Phe Thr Glu Lys Glu Thr Ala Asn Pro
 65                  70                  75                  80

Ala Phe Asn Gly Glu Val Ile Lys Arg Tyr Lys Glu Leu Met Glu His
                 85                  90                  95

Gly Glu Gly Ile Ala Asp Ile Leu Arg Ser Arg Leu Ala Lys Phe Leu
                100                 105                 110

Asn Thr Lys Asp Val Gly Lys Arg Phe Ala Gln Gly Thr Glu Ala Asn
            115                 120                 125

Arg Trp Val Gly Gly Lys Leu Leu Asn Ile Val Glu Gln Asp Gly Asp
    130                 135                 140

Thr Phe Lys Tyr Asn Glu Gln Leu Leu Gln Thr Ala Val Leu Ala Gly
145                 150                 155                 160

Leu Gln Trp Arg Leu Thr Ala Thr Ser Asn Thr Ala Ile Lys Asp Ala
                165                 170                 175

Lys Asp Val Ala Ala Ile Thr Gly Ile Asp Gln Ala Leu Leu Pro Glu
            180                 185                 190

Gly Leu Val Glu Gln Phe Asp Thr Gly Met Thr Leu Thr Glu Ala Val
        195                 200                 205

Ser Ser Leu Ala Gln Lys Ile Glu Ser Tyr Trp Gly Leu Ser Arg Asn
    210                 215                 220

Pro Asn Ala Pro Leu Gly Tyr Thr Lys Gly Ile Pro Thr Ala Met Ala
225                 230                 235                 240

Ala Glu Ile Leu Ala Ala Phe Val Glu Ser Thr Asp Val Val Glu Asn
                245                 250                 255

Ile Val Asp Met Ser Glu Ile Asp Pro Asp Asn Lys Lys Thr Ile Gly
            260                 265                 270

Leu Tyr Thr Ile Thr Glu Leu Asp Ser Phe Asp Pro Ile Asn Ser Phe
        275                 280                 285

Pro Thr Ala Ile Glu Glu Ala Val Leu Val Asn Pro Thr Glu Lys Met
    290                 295                 300

Phe Phe Gly Asp Asp Ile Pro Pro Val Ala Asn Thr Gln Leu Arg Asn
305                 310                 315                 320

Pro Ala Val Arg Asn Thr Pro Glu Gln Lys Ala Ala Leu Lys Ala Glu
                325                 330                 335

Gln Ala Thr Glu Phe Tyr Val His Thr Pro Met Val Gln Phe Tyr Glu
            340                 345                 350

Thr Leu Gly Lys Asp Arg Ile Leu Glu Leu Met Gly Ala Gly Thr Leu
        355                 360                 365

Asn Lys Glu Leu Leu Asn Asp Asn His Ala Lys Ser Leu Glu Gly Lys
    370                 375                 380

Asn Arg Ser Val Glu Asp Ser Tyr Asn Gln Leu Phe Ser Val Ile Glu
385                 390                 395                 400
```

```
Gln Val Arg Ala Gln Ser Glu Asp Ile Ser Thr Val Pro Ile His Tyr
                405                 410                 415
Ala Tyr Asn Met Thr Arg Val Gly Arg Met Gln Met Leu Gly Lys Tyr
            420                 425                 430
Asn Pro Gln Ser Ala Lys Leu Val Arg Glu Ala Ile Leu Pro Thr Lys
        435                 440                 445
Ala Thr Leu Asp Leu Ser Asn Gln Asn Asn Glu Asp Phe Ser Ala Phe
    450                 455                 460
Gln Leu Gly Leu Ala Gln Ala Leu Asp Ile Lys Val His Thr Met Thr
465                 470                 475                 480
Arg Glu Val Met Ser Asp Glu Leu Thr Lys Leu Leu Glu Gly Asn Leu
                485                 490                 495
Lys Pro Ala Ile Asp Met Met Val Glu Phe Asn Thr Thr Gly Ser Leu
            500                 505                 510
Pro Glu Asn Ala Val Asp Val Leu Asn Thr Ala Leu Gly Asp Arg Lys
        515                 520                 525
Ser Phe Val Ala Leu Met Ala Leu Met Glu Tyr Ser Arg Tyr Leu Val
    530                 535                 540
Ala Glu Asp Lys Ser Ala Phe Val Thr Pro Leu Tyr Val Glu Ala Asp
545                 550                 555                 560
Gly Val Thr Asn Gly Pro Ile Asn Ala Met Met Leu Met Thr Gly Gly
                565                 570                 575
Leu Phe Thr Pro Asp Trp Ile Arg Asn Ile Ala Lys Gly Gly Leu Phe
            580                 585                 590
Ile Gly Ser Pro Asn Lys Thr Met Asn Glu His Arg Ser Thr Ala Asp
        595                 600                 605
Asn Asn Asp Leu Tyr Gln Ala Ser Thr Asn Ala Leu Met Glu Ser Leu
    610                 615                 620
Gly Lys Leu Arg Ser Asn Tyr Ala Ser Asn Met Pro Ile Gln Ser Gln
625                 630                 635                 640
Ile Asp Ser Leu Leu Ser Leu Met Asp Leu Phe Leu Pro Asp Ile Asn
                645                 650                 655
Leu Gly Glu Asn Gly Ala Leu Glu Leu Lys Arg Gly Ile Ala Lys Asn
            660                 665                 670
Pro Leu Thr Ile Thr Ile Tyr Gly Ser Gly Ala Arg Gly Ile Ala Gly
        675                 680                 685
Lys Leu Val Ser Ser Val Thr Asp Ala Ile Tyr Glu Arg Met Ser Asp
    690                 695                 700
Val Leu Lys Ala Arg Ala Lys Asp Pro Asn Ile Ser Ala Ala Met Ala
705                 710                 715                 720
Met Phe Gly Lys Gln Ala Ser Glu Ala His Ala Glu Glu Leu Leu
                725                 730                 735
Ala Arg Phe Leu Lys Asp Met Glu Thr Leu Thr Ser Thr Val Pro Val
            740                 745                 750
Lys Arg Lys Gly Val Leu Glu Leu Gln Ser Thr Gly Thr Gly Ala Lys
        755                 760                 765
Gly Lys Ile Asn Pro Lys Thr Tyr Thr Ile Lys Gly Glu Gln Leu Lys
    770                 775                 780
Ala Leu Gln Glu Asn Met Leu His Phe Phe Val Glu Pro Leu Arg Asn
785                 790                 795                 800
Gly Ile Thr Gln Thr Val Gly Glu Ser Leu Val Tyr Ser Thr Glu Gln
                805                 810                 815
```

Leu Gln Lys Ala Thr Gln Ile Gln Ser Val Val Leu Glu Asp Met Phe
            820                 825                 830

Lys Gln Arg Val Gln Glu Lys Leu Ala Glu Lys Ala Lys Asp Pro Thr
        835                 840                 845

Trp Lys Lys Gly Asp Phe Leu Thr Gln Lys Glu Leu Asn Asp Ile Gln
    850                 855                 860

Ala Ser Leu Asn Asn Leu Ala Pro Met Ile Glu Thr Gly Ser Gln Thr
865                 870                 875                 880

Phe Tyr Ile Ala Gly Ser Glu Asn Ala Glu Val Ala Asn Gln Val Leu
                885                 890                 895

Ala Thr Asn Leu Asp Asp Arg Met Arg Val Pro Met Ser Ile Tyr Ala
            900                 905                 910

Pro Ala Gln Ala Gly Val Ala Gly Ile Pro Phe Met Thr Ile Gly Thr
        915                 920                 925

Gly Asp Gly Met Met Met Gln Thr Leu Ser Thr Met Lys Gly Ala Pro
    930                 935                 940

Lys Asn Thr Leu Lys Ile Phe Asp Gly Met Asn Ile Gly Leu Asn Asp
945                 950                 955                 960

Ile Thr Asp Ala Ser Arg Lys Ala Asn Glu Ala Val Tyr Thr Ser Trp
                965                 970                 975

Gln Gly Asn Pro Ile Lys Asn Val Tyr Glu Ser Tyr Ala Lys Phe Met
            980                 985                 990

Lys Asn Val Asp Phe Ser Lys Leu Ser Pro Glu Ala Leu Glu Ala Ile
        995                 1000                1005

Gly Lys Ser Ala Leu Glu Tyr Asp Gln Arg Glu Asn Ala Thr Val Asp
    1010                1015                1020

Asp Ile Ala Asn Ala Ala Ser Leu Ile Glu Arg Asn Leu Arg Asn Ile
1025                1030                1035                1040

Ala Leu Gly Val Asp Ile Arg His Lys Val Leu Asp Lys Val Asn Leu
                1045                1050                1055

Ser Ile Asp Gln Met Ala Ala Val Gly Ala Pro Tyr Gln Asn Asn Gly
            1060                1065                1070

Lys Ile Asp Leu Ser Asn Met Thr Pro Glu Gln Gln Ala Asp Glu Leu
        1075                1080                1085

Asn Lys Leu Phe Arg Glu Glu Leu Glu Ala Arg Lys Gln Lys Val Ala
    1090                1095                1100

Lys Ala Arg
1105

<210> SEQ ID NO 5
<211> LENGTH: 3432
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5 atgggggtt ctcatcatca tcatcatcat ggtatggcta gcatgactgg tggacagcaa      60
atgggtcggg atctgtacga cgatgacgat aaggatccga gctcgagatc tgaaagtaca     120
gttacagaag aattaaaaga aggtattgat gctgtttacc cttcattggt aggtactgct     180
gattctaaag cagagggtat taagaactat ttcaaattgt cctttacctt accagaagaa     240
cagaaatccc gtactgttgg ttcagaagca cctctaaaag atgtagccca agctctgtct     300
tctcgtgctc gttatgaact ctttactgag aaagaaactg ctaaccctgc ttttaatggg     360

```
gaagttatta agcgatacaa agaactcatg gaacatgggg aaggtattgc tgatattctt    420
cgctcccgtc tggctaagtt ccttaacact aaggatgttg gtaaacgttt tgctcaaggt    480
acagaagcca accgttgggt aggtggtaag ttacttaaca ttgttgagca ggatggggat    540
acctttaagt acaacgaaca attgctacag actgctgtat tagcaggtct tcaatggaga    600
cttactgcta ccagcaatac tgctatcaaa gatgcaaaag atgttgctgc tattactggt    660
attgaccaag ctctgctgcc agaaggttta gtagagcaat tgatactgg tatgacactc     720
actgaagcag ttagttccct ggctcagaaa attgagtctt actggggatt atctcgtaat    780
ccaaatgctc cattgggcta taccaaaggc atccctacag caatggctgc tgaaattctg    840
gctgcatttg tagagtctac tgatgttgta gagaacatcg tggatatgtc agaaattgac    900
ccagataaca agaagactat tggtctgtac accattactg aactggattc cttcgaccca    960
attaatagct tccctactgc tattgaagaa gctgttttag tgaatcctac agagaagatg   1020
ttctttggtg atgacattcc tcctgtagct aatactcagc ttcgtaaccc tgctgttcgt   1080
aatactccag aacagaaggc tgcattgaaa gcagagcagg ctacagagtt ctatgtacac   1140
accccaatgg ttcaattcta tgagacgtta ggtaaagacc gtattctcga actgatgggt   1200
gctggtactc tgaataaaga gttacttaat gataaccatg ctaaatctct ggaaggtaag   1260
aaccgttcag tagaggactc ttacaaccaa ctgttctccg tcattgagca ggtaagagca   1320
cagagcgaag acatctctac tgtacctatt cactatgcat acaatatgac ccgtgttggt   1380
cgtatgcaga tgttaggtaa atacaatcct caatcagcca aactggttcg tgaggccatc   1440
ttacctacta agctactttt ggatttatcg aaccagaaca atgaagactt ctctgcattc   1500
cagttaggtc tggctcaggc attggacatt aaagtccata ctatgactcg tgaggttatg   1560
tctgacgagt tgactaaatt actggaaggt aatctgaaac cagccattga tatgatggtt   1620
gagtttaata ccactggttc cttaccagaa aacgcagttg atgttctgaa tacagcatta   1680
ggagatagga agtcattcgt agcattgatg gctcttatgg agtattcccg ttacttagta   1740
gcagaggata atctgcatt tgtaactcca ctgtatgtag aagcagatgg tgttactaat    1800
ggtccaatca atgccatgat gctaatgaca ggcggtctgt ttactcctga ctggattcgt   1860
aatattgcca aagggggctt gttcattggt tctccaaata gaccatgaa tgagcatcgc    1920
tctactgctg acaataatga tttatatcaa gcatccacta atgctttgat ggaatcgttg   1980
ggtaagttac gtagtaacta tgcctctaat atgcctattc agtctcagat agacagtctt   2040
ctttctctga tggatttgtt tttaccggat attaatcttg gtgagaatgg tgctttagaa   2100
cttaaacgtg gtattgctaa gaacccactg actattacca tctatggttc tggtgctcgt   2160
ggtattgcag gtaagctggt tagttctgtt actgatgcca tctatgagcg tatgtctgat   2220
gtactgaaag ctcgtgctaa agacccaaat atctctgctg ctatggcaat gtttggtaag   2280
caagctgctt cagaagcaca tgctgaagaa cttcttgccc gtttcctgaa agatatggaa   2340
acactgactt ctactgttcc tgttaaacgt aaaggtgtac tggaactaca atccacaggt   2400
acaggagcca aggaaaaaat caatcctaag acctatacca ttaagggcga gcaactgaag   2460
gcacttcagg aaaatatgct gcacttcttt gtagaaccac tacgtaatgg tattactcag   2520
actgtaggtg aaagtctggt gtactctact gaacaattac agaaagctac tcagattcaa   2580
tctgtagtgc tggaagatat gttcaaacag cgagtacaag agaagctggc agagaaggct   2640
aaagacccaa catggaagaa aggtgatttc cttactcaga aagaactgaa tgatattcag   2700
```

-continued

```
gcttctctga ataacttagc ccctatgatt gagactggtt ctcagacttt ctacattgct    2760
ggttcagaaa atgcagaagt agcaaatcag gtattagcta ctaaccttga tgaccgtatg    2820
cgtgtaccaa tgagtatcta tgctccagca caggccggtg tagcaggtat tccatttatg    2880
actattggta ctggtgatgg catgatgatg caaactcttt ccactatgaa aggtgcacca    2940
aagaataccc tcaaaatctt tgatggtatg aacattggtt tgaatgacat cactgatgcc    3000
agtcgtaaag ctaatgaagc tgtttacact tcttggcagg gtaaccctat taagaatgtt    3060
tatgaatcat atgctaagtt catgaagaat gtagatttca gcaagctgtc ccctgaagca    3120
ttggaagcaa ttggtaaatc tgctctggaa tatgaccaac gtgagaatgc tactgtagat    3180
gatattgcta acgctgcatc tctgattgaa cgtaacttac gtaatattgc actgggtgta    3240
gatattcgtc ataaggtgct ggataaggta atctgtcca ttgaccagat ggctgctgta    3300
ggtgctcctt atcagaacaa cggtaagatt gacctcagca atatgacccc tgaacaacag    3360
gctgatgaac tgaataaact tttccgtgaa gagttagaag cccgtaaaca aaaagtcgct    3420
aaggctaggt aa                                                       3432
```

<210> SEQ ID NO 6
<211> LENGTH: 1143
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 6

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
             20                  25                  30

Pro Ser Ser Arg Ser Glu Ser Thr Val Thr Glu Glu Leu Lys Glu Gly
         35                  40                  45

Ile Asp Ala Val Tyr Pro Ser Leu Val Gly Thr Ala Asp Ser Lys Ala
     50                  55                  60

Glu Gly Ile Lys Asn Tyr Phe Lys Leu Ser Phe Thr Leu Pro Glu Glu
 65                  70                  75                  80

Gln Lys Ser Arg Thr Val Gly Ser Glu Ala Pro Leu Lys Asp Val Ala
                 85                  90                  95

Gln Ala Leu Ser Ser Arg Ala Arg Tyr Glu Leu Phe Thr Glu Lys Glu
            100                 105                 110

Thr Ala Asn Pro Ala Phe Asn Gly Glu Val Ile Lys Arg Tyr Lys Glu
        115                 120                 125

Leu Met Glu His Gly Glu Gly Ile Ala Asp Ile Leu Arg Ser Arg Leu
    130                 135                 140

Ala Lys Phe Leu Asn Thr Lys Asp Val Gly Lys Arg Phe Ala Gln Gly
145                 150                 155                 160

Thr Glu Ala Asn Arg Trp Val Gly Gly Lys Leu Leu Asn Ile Val Glu
                165                 170                 175

Gln Asp Gly Asp Thr Phe Lys Tyr Asn Glu Gln Leu Leu Gln Thr Ala
            180                 185                 190

Val Leu Ala Gly Leu Gln Trp Arg Leu Thr Ala Thr Ser Asn Thr Ala
        195                 200                 205

Ile Lys Asp Ala Lys Asp Val Ala Ala Ile Thr Gly Ile Asp Gln Ala
    210                 215                 220
```

-continued

```
Leu Leu Pro Glu Gly Leu Val Glu Gln Phe Asp Thr Gly Met Thr Leu
225                 230                 235                 240

Thr Glu Ala Val Ser Ser Leu Ala Gln Lys Ile Glu Ser Tyr Trp Gly
                245                 250                 255

Leu Ser Arg Asn Pro Asn Ala Pro Leu Gly Tyr Thr Lys Gly Ile Pro
            260                 265                 270

Thr Ala Met Ala Ala Glu Ile Leu Ala Ala Phe Val Glu Ser Thr Asp
        275                 280                 285

Val Val Glu Asn Ile Val Asp Met Ser Glu Ile Asp Pro Asp Asn Lys
    290                 295                 300

Lys Thr Ile Gly Leu Tyr Thr Ile Thr Glu Leu Asp Ser Phe Asp Pro
305                 310                 315                 320

Ile Asn Ser Phe Pro Thr Ala Ile Glu Glu Ala Val Leu Val Asn Pro
                325                 330                 335

Thr Glu Lys Met Phe Phe Gly Asp Asp Ile Pro Pro Val Ala Asn Thr
            340                 345                 350

Gln Leu Arg Asn Pro Ala Val Arg Asn Thr Pro Glu Gln Lys Ala Ala
        355                 360                 365

Leu Lys Ala Glu Gln Ala Thr Glu Phe Tyr Val His Thr Pro Met Val
    370                 375                 380

Gln Phe Tyr Glu Thr Leu Gly Lys Asp Arg Ile Leu Glu Leu Met Gly
385                 390                 395                 400

Ala Gly Thr Leu Asn Lys Glu Leu Leu Asn Asp Asn His Ala Lys Ser
                405                 410                 415

Leu Glu Gly Lys Asn Arg Ser Val Glu Asp Ser Tyr Asn Gln Leu Phe
            420                 425                 430

Ser Val Ile Glu Gln Val Arg Ala Gln Ser Glu Asp Ile Ser Thr Val
        435                 440                 445

Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560

Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
```

-continued

```
                645                 650                 655
Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
            675                 680                 685

Pro Asp Ile Asn Leu Gly Glu Asn Gly Ala Leu Glu Leu Lys Arg Gly
            690                 695                 700

Ile Ala Lys Asn Pro Leu Thr Ile Thr Ile Tyr Gly Ser Gly Ala Arg
705                 710                 715                 720

Gly Ile Ala Gly Lys Leu Val Ser Ser Val Thr Asp Ala Ile Tyr Glu
                725                 730                 735

Arg Met Ser Asp Val Leu Lys Ala Arg Ala Lys Asp Pro Asn Ile Ser
                740                 745                 750

Ala Ala Met Ala Met Phe Gly Lys Gln Ala Ala Ser Glu Ala His Ala
                755                 760                 765

Glu Glu Leu Leu Ala Arg Phe Leu Lys Asp Met Glu Thr Leu Thr Ser
            770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
                820                 825                 830

Pro Leu Arg Asn Gly Ile Thr Gln Thr Val Gly Glu Ser Leu Val Tyr
            835                 840                 845

Ser Thr Glu Gln Leu Gln Lys Ala Thr Gln Ile Gln Ser Val Val Leu
850                 855                 860

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
                885                 890                 895

Asn Asp Ile Gln Ala Ser Leu Asn Asn Leu Ala Pro Met Ile Glu Thr
            900                 905                 910

Gly Ser Gln Thr Phe Tyr Ile Ala Gly Ser Glu Asn Ala Glu Val Ala
            915                 920                 925

Asn Gln Val Leu Ala Thr Asn Leu Asp Asp Arg Met Arg Val Pro Met
            930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
            980                 985                 990

Gly Leu Asn Asp Ile Thr Asp Ala Ser Arg Lys Ala Asn Glu Ala Val
            995                 1000                1005

Tyr Thr Ser Trp Gln Gly Asn Pro Ile Lys Asn Val Tyr Glu Ser Tyr
    1010                1015                1020

Ala Lys Phe Met Lys Asn Val Asp Phe Ser Lys Leu Ser Pro Glu Ala
1025                1030                1035                1040

Leu Glu Ala Ile Gly Lys Ser Ala Leu Glu Tyr Asp Gln Arg Glu Asn
                1045                1050                1055

Ala Thr Val Asp Asp Ile Ala Asn Ala Ala Ser Leu Ile Glu Arg Asn
            1060                1065                1070
```

```
Leu Arg Asn Ile Ala Leu Gly Val Asp Ile Arg His Lys Val Leu Asp
        1075                1080                1085

Lys Val Asn Leu Ser Ile Asp Gln Met Ala Ala Val Gly Ala Pro Tyr
    1090                1095                1100

Gln Asn Asn Gly Lys Ile Asp Leu Ser Asn Met Thr Pro Glu Gln Gln
1105                1110                1115                1120

Ala Asp Glu Leu Asn Lys Leu Phe Arg Glu Glu Leu Glu Ala Arg Lys
                1125                1130                1135

Gln Lys Val Ala Lys Ala Arg
        1140

<210> SEQ ID NO 7
<211> LENGTH: 3432
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7 atgggggggtt ctcatcatca tcatcatcat ggtatggcta gcatgactgg tggacagcaa      60
atgggtcggg atctgtacga cgatgacgat aaggatccga gctcgagatc tgaaagtaca     120
gttacagaag aattaaaaga aggtattgat gctgtttacc cttcattggt aggtactgct     180
gattctaaag cagagggtat taagaactat ttcaaattgt cctttacctt accagaagaa     240
cagaaatccc gtactgttgg ttcagaagca cctctaaaag atgtagccca agctctgtct     300
tctcgtgctc gttatgaact ctttactgag aaagaaactg ctaaccctgc ttttaatggg     360
gaagttatta agcgatacaa agaactcatg gaacatgggg aaggtattgc tgatattctt     420
cgctcccgtc tggctaagtt ccttaacact aaggatgttg gtaaacgttt tgctcaaggt     480
acagaagcca accgttgggt aggtggtaag ttacttaaca ttgttgagca ggatggggat     540
acctttaagt acaacgaaca attgctacag actgctgtat tagcaggtct tcaatggaga     600
cttactgcta ccagcaatac tgctatcaaa gatgcaaaag atgttgctgc tattactggt     660
attgaccaag ctctgctgcc agaaggttta gtagagcaat tgatactgg tatgacactc     720 actgaagcag ttagttccct ggctcagaaa ttgagtctt actggggatt atctcgtaat     780
ccaaatgctc cattgggcta taccaaaggc atccctacag caatggctgc tgaaattctg     840
gctgcatttg tagagtctac tgatgttgta gagaacatcg tggatatgtc agaaattgac     900
ccagataaca gaagactat tggtctgtac accattactg aactggattc cttcgaccca     960
attaatagct tccctactgc tattgaagaa gctgttttag tgaatcctac agagaagatg    1020
ttctttggtg atgacattcc tcctgtagct aatactcagc ttcgtaaccc tgctgttcgt    1080
aatactccag aacagaaggc tgcattgaaa gcagagcagg ctacagagtt ctatgtacac    1140
accccaatgg ttcaattcta tgagacgtta ggtaaagacc gtattctcga actgatgggt    1200
gctggtactc tgaataaaga gttacttaat gataaccatg ctaaatctct ggaaggtaag    1260
aaccgttcag tagaggactc ttacaaccaa ctgttctccg tcattgagca ggtaagagca    1320
cagagcgaag acatctctac tgtacctatt cactatgcat acaatatgac ccgtgttggt    1380
cgtatgcaga tgttaggtaa atacaatcct caatcagcca aactggttcg tgaggccatc    1440
ttacctacta agctactttt ggatttatcg aaccagaaca atgaagactt ctctgcattc    1500
cagttaggtc tggctcaggc attggacatt aaagtccata ctatgactcg tgaggttatg    1560
```

| | | |
|---|---|---|
| tctgacgagt tgactaaatt actggaaggt aatctgaaac cagccattga tatgatggtt | 1620 | |
| gagtttaata ccactggttc cttaccagaa aacgcagttg atgttctgaa tacagcatta | 1680 | |
| ggagatagga agtcattcgt agcattgatg gctcttatgg agtattcccg ttacttagta | 1740 | |
| gcagaggata aatctgcatt tgtaactcca ctgtatgtag aagcagatgg tgttactaat | 1800 | |
| ggtccaatca atgccatgat gctaatgaca ggcggtctgt ttactcctga ctggattcgt | 1860 | |
| aatattgcca aggggggctt gttcattggt ctccaaata agaccatgaa tgagcatcgc | 1920 | |
| tctactgctg acaataatga tttatatcaa gcatccacta atgctttgat ggaatcgttg | 1980 | |
| ggtaagttac gtagtaacta tgcctctaat atgcctattc agtctcagat agacagtctt | 2040 | |
| ctttctctga tggatttgtt tttaccggat attaatcttg gtgagaatgg tgctttagaa | 2100 | |
| cttaaacgtg gtattgctaa gaacccactg actattacca tcttcggttc tggtgctcgt | 2160 | |
| ggtattgcag gtaagctggt tagttctgtt actgatgcca tctatgagcg tatgtctgat | 2220 | |
| gtactgaaag ctcgtgctaa agacccaaat atctctgctg ctatggcaat gtttggtaag | 2280 | |
| caagctgctt cagaagcaca tgctgaagaa cttcttgccc gtttcctgaa agatatggaa | 2340 | |
| acactgactt ctactgttcc tgttaaacgt aaaggtgtac tggaactaca atccacaggt | 2400 | |
| acaggagcca aggaaaaat caatcctaag acctatacca ttaagggcga gcaactgaag | 2460 | |
| gcacttcagg aaaatatgct gcacttcttt gtagaaccac tacgtaatgg tattactcag | 2520 | |
| actgtaggtg aaagtctggt gtactctact gaacaattac agaaagctac tcagattcaa | 2580 | |
| tctgtagtgc tggaagatat gttcaaacag cgagtacaag agaagctggc agagaaggct | 2640 | |
| aaagacccaa catggaagaa aggtgatttc cttactcaga agaactgaa tgatattcag | 2700 | |
| gcttctctga ataacttagc ccctatgatt gagactggtt ctcagacttt ctacattgct | 2760 | |
| ggttcagaaa atgcagaagt agcaaatcag gtattagcta ctaaccttga tgaccgtatg | 2820 | |
| cgtgtaccaa tgagtatcta tgctccagca caggccggtg tagcaggtat tccatttatg | 2880 | |
| actattggta ctggtgatgg catgatgatg caaactcttt ccactatgaa aggtgcacca | 2940 | |
| aagaataccc tcaaaatctt tgatggtatg aacattggtt tgaatgacat cactgatgcc | 3000 | |
| agtcgtaaag ctaatgaagc tgtttacact tcttggcagg gtaaccctat taagaatgtt | 3060 | |
| tatgaatcat atgctaagtt catgaagaat gtagatttca gcaagctgtc ccctgaagca | 3120 | |
| ttggaagcaa ttggtaaatc tgctctggaa tatgaccaac gtgagaatgc tactgtagat | 3180 | |
| gatattgcta cgctgcatc tctgattgaa cgtaacttac gtaatattgc actgggtgta | 3240 | |
| gatattcgtc ataaggtgct ggataaggta aatctgtcca ttgaccagat ggctgctgta | 3300 | |
| ggtgctcctt atcagaacaa cggtaagatt gacctcagca atatgacccc tgaacaacag | 3360 | |
| gctgatgaac tgaataaact tttccgtgaa gagttagaag cccgtaaaca aaaagtcgct | 3420 | |
| aaggctaggt aa | 3432 | |

<210> SEQ ID NO 8
<211> LENGTH: 1143
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Gly Gly Ser His His His His His His Gly Met Ala Ser Met Thr
 1               5                  10                  15

Gly Gly Gln Gln Met Gly Arg Asp Leu Tyr Asp Asp Asp Asp Lys Asp

-continued

```
                20                  25                  30
Pro Ser Ser Arg Ser Glu Ser Thr Val Thr Glu Glu Leu Lys Glu Gly
            35                  40                  45
Ile Asp Ala Val Tyr Pro Ser Leu Val Gly Thr Ala Asp Ser Lys Ala
50                  55                  60
Glu Gly Ile Lys Asn Tyr Phe Lys Leu Ser Phe Thr Leu Pro Glu Glu
65                  70                  75                  80
Gln Lys Ser Arg Thr Val Gly Ser Glu Ala Pro Leu Lys Asp Val Ala
                85                  90                  95
Gln Ala Leu Ser Ser Arg Ala Arg Tyr Glu Leu Phe Thr Glu Lys Glu
            100                 105                 110
Thr Ala Asn Pro Ala Phe Asn Gly Glu Val Ile Lys Arg Tyr Lys Glu
            115                 120                 125
Leu Met Glu His Gly Gly Ile Ala Asp Ile Leu Arg Ser Arg Leu
            130                 135                 140
Ala Lys Phe Leu Asn Thr Lys Asp Val Gly Lys Arg Phe Ala Gln Gly
145                 150                 155                 160
Thr Glu Ala Asn Arg Trp Val Gly Gly Lys Leu Leu Asn Ile Val Glu
                165                 170                 175
Gln Asp Gly Asp Thr Phe Lys Tyr Asn Glu Gln Leu Leu Gln Thr Ala
            180                 185                 190
Val Leu Ala Gly Leu Gln Trp Arg Leu Thr Ala Thr Ser Asn Thr Ala
            195                 200                 205
Ile Lys Asp Ala Lys Asp Val Ala Ala Ile Thr Gly Ile Asp Gln Ala
210                 215                 220
Leu Leu Pro Glu Gly Leu Val Glu Gln Phe Asp Thr Gly Met Thr Leu
225                 230                 235                 240
Thr Glu Ala Val Ser Ser Leu Ala Gln Lys Ile Glu Ser Tyr Trp Gly
                245                 250                 255
Leu Ser Arg Asn Pro Asn Ala Pro Leu Gly Tyr Thr Lys Gly Ile Pro
            260                 265                 270
Thr Ala Met Ala Ala Glu Ile Leu Ala Ala Phe Val Glu Ser Thr Asp
            275                 280                 285
Val Val Glu Asn Ile Val Asp Met Ser Glu Ile Asp Pro Asp Asn Lys
290                 295                 300
Lys Thr Ile Gly Leu Tyr Thr Ile Thr Glu Leu Asp Ser Phe Asp Pro
305                 310                 315                 320
Ile Asn Ser Phe Pro Thr Ala Ile Glu Glu Ala Val Leu Val Asn Pro
                325                 330                 335
Thr Glu Lys Met Phe Phe Gly Asp Asp Ile Pro Pro Val Ala Asn Thr
            340                 345                 350
Gln Leu Arg Asn Pro Ala Val Arg Asn Thr Pro Glu Gln Lys Ala Ala
            355                 360                 365
Leu Lys Ala Glu Gln Ala Thr Glu Phe Tyr Val His Thr Pro Met Val
            370                 375                 380
Gln Phe Tyr Glu Thr Leu Gly Lys Asp Arg Ile Leu Glu Leu Met Gly
385                 390                 395                 400
Ala Gly Thr Leu Asn Lys Glu Leu Leu Asn Asp Asn His Ala Lys Ser
                405                 410                 415
Leu Glu Gly Lys Asn Arg Ser Val Glu Asp Ser Tyr Asn Gln Leu Phe
            420                 425                 430
Ser Val Ile Glu Gln Val Arg Ala Gln Ser Glu Asp Ile Ser Thr Val
            435                 440                 445
```

```
Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560

Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
                645                 650                 655

Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
        675                 680                 685

Pro Asp Ile Asn Leu Gly Glu Asn Gly Ala Leu Glu Leu Lys Arg Gly
    690                 695                 700

Ile Ala Lys Asn Pro Leu Thr Ile Thr Ile Phe Gly Ser Gly Ala Arg
705                 710                 715                 720

Gly Ile Ala Gly Lys Leu Val Ser Ser Val Thr Asp Ala Ile Tyr Glu
                725                 730                 735

Arg Met Ser Asp Val Leu Lys Ala Arg Ala Lys Asp Pro Asn Ile Ser
            740                 745                 750

Ala Ala Met Ala Met Phe Gly Lys Gln Ala Ala Ser Glu Ala His Ala
        755                 760                 765

Glu Glu Leu Leu Ala Arg Phe Leu Lys Asp Met Glu Thr Leu Thr Ser
    770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
            820                 825                 830

Pro Leu Arg Asn Gly Ile Thr Gln Thr Val Gly Glu Ser Leu Val Tyr
        835                 840                 845

Ser Thr Glu Gln Leu Gln Lys Ala Thr Gln Ile Gln Ser Val Val Leu
    850                 855                 860
```

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
            885                 890                 895

Asn Asp Ile Gln Ala Ser Leu Asn Asn Leu Ala Pro Met Ile Glu Thr
        900                 905                 910

Gly Ser Gln Thr Phe Tyr Ile Ala Gly Ser Glu Asn Ala Glu Val Ala
    915                 920                 925

Asn Gln Val Leu Ala Thr Asn Leu Asp Asp Arg Met Arg Val Pro Met
930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
            980                 985                 990

Gly Leu Asn Asp Ile Thr Asp Ala Ser Arg Lys Ala Asn Glu Ala Val
        995                 1000                1005

Tyr Thr Ser Trp Gln Gly Asn Pro Ile Lys Asn Val Tyr Glu Ser Tyr
    1010                1015                1020

Ala Lys Phe Met Lys Asn Val Asp Phe Ser Lys Leu Ser Pro Glu Ala
1025                1030                1035                1040

Leu Glu Ala Ile Gly Lys Ser Ala Leu Glu Tyr Asp Gln Arg Glu Asn
                1045                1050                1055

Ala Thr Val Asp Asp Ile Ala Asn Ala Ala Ser Leu Ile Glu Arg Asn
            1060                1065                1070

Leu Arg Asn Ile Ala Leu Gly Val Asp Ile Arg His Lys Val Leu Asp
        1075                1080                1085

Lys Val Asn Leu Ser Ile Asp Gln Met Ala Ala Val Gly Ala Pro Tyr
    1090                1095                1100

Gln Asn Asn Gly Lys Ile Asp Leu Ser Asn Met Thr Pro Glu Gln Gln
1105                1110                1115                1120

Ala Asp Glu Leu Asn Lys Leu Phe Arg Glu Glu Leu Glu Ala Arg Lys
                1125                1130                1135

Gln Lys Val Ala Lys Ala Arg
        1140

<210> SEQ ID NO 9
<211> LENGTH: 69
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tcccagacaa aaggttaaga tttcatacag gattggatgc attacttcat ccaaaagaag    60
cggagcttc                                                            69

<210> SEQ ID NO 10
<211> LENGTH: 69
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10

```
tgggagagaa aaggttaaga tttgatagag gattggatgg attagttgat ggaaaagaag    60
cggagcttc                                                           69

<210> SEQ ID NO 11
<211> LENGTH: 69
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
tccctgtctt ttggttttgt tttctttctg gtttggttgc ttttcttctt ccaaaagaag    60
cggagcttc                                                           69

<210> SEQ ID NO 12
<211> LENGTH: 69
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tcccacacaa aaccttaaca tttcatacac cattccatcc attacttcat ccaaaagaag    60
cggagcttc                                                           69

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
acccagacaa aaggaaaaga aaacaaacag gaaaggaagc aaaacaacaa ccaaaagaag    60
cggagcttc                                                           69

<210> SEQ ID NO 14
<211> LENGTH: 10617
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14 atgggggtt ctcatcatca tcatcatcat ggtatggcta gcatgactgg tggacagcaa      60
atgggtcggg atctgtacga cgatgacgat aaggatccga gctcgagatc tatgtcagta   120
tttgatagac tggctgggtt cgcagacagc gtaaccaatg caaagcaagt tgacgtctct   180
actgcaaccg cccagaagaa agctgaacaa ggtgtcacta ctcctcttgt ttctcctgat   240
gctgcttatc aaatgcaagc tgcccgtact ggtaatgttg gggctaatgc atttgaacca   300
gggacagtgc aatcagattt catgaatctg accccaatgc aaatcatgaa taagtatggg   360
gttgagcaag gcttacaact tatcaatgct cgtgctgatg cagggaacca ggtattcaat   420
gattcagtta ctacaagaac tcctggggaa gaactggggg atattgctac tggtgttggc   480
cttggttttg ttaatacccct tgggggcatt ggtgctcttg ggggcaggctt actcaacgat   540
```

```
gatgcaggtg ctgttgttgc tcaacaattg agtaagttta atgatgctgt tcatgctacc      600
caaagccagg cattacaaga taaacgtaag ctctttgctg ctcgtaactt aatgaatgaa      660
gtagagagtg aacgtcagta tcaaacagat aagaaagaag cactaatga catagtagct      720 tccttatcta aatttggacg tgattttgta ggttcaattg agaatgctgc tcaaactgac      780
tctattattt ctgatgggtt agcagaaggg gtaggttctc tattaggtgc tggtcctgta      840 ttaagggtg catctttact gggtaaagca gttgttccag caaatactct tcgtagtgct      900
gcattggctg gtgctattga tgcaggtact ggtactcagt cactggctcg tattgcctct      960
actgtaggta gagctgcacc gggtatggtt ggtgttggtg caatggaagc tggtggtgca     1020
taccaacaaa ctgctgatga aattatgaag atgagtctta aagacttaga gaagtctcct     1080
gtttatcagc aacatattaa agatggtatg tccccctgaac aggctcgtcg tcagactgca    1140
tctgaaactg gtcttactgc tgctgctatt caattaccta ttgctgctgc aaccggtcct     1200
ctggtatccc gttttgagat ggctcctttc cgtgctggct ctttaggtgc tgtaggtatg     1260
aaccttgccc gtgaaacagt ggaagaaggt gttcagggtg ctacaggcca actggctcag     1320
aatattgcac agcaacaaaa cattgataag aaccaagacc tgcttaaagg tgtcggtaca     1380
caggctggtt taggtgctct ttatggcttt ggttctgctg gtgttgtaca ggctccggct     1440
ggtgctgctc gtttagcagg tgctgcaact gctcctgtat tgcgtaccac aatggctggt     1500
gttaaagctg ctggtagtgt agcaggtaag gttgtttctc ctattaagaa tactttagta     1560
gctcgtggtg aacgggttat gaagcagaat gaagaagcat ctcctgttgc tgatgactat     1620
gttgcacagg cagcacaaga agctatggct caagcaccag aagcagaagt tactattcgt     1680
gatgctgttg aagcaactga tgctactcca gaacagaaag ttgcagcaca ccagtatgtt     1740
tctgacttaa tgaatgctac tcgttttaat cctgaaaatt atcaggaagc accagagcat     1800
attcgtaatg ctgtagctgg ttctactgac caagtacagg ttattcagaa gttagcagac     1860
ttagttaaca cattagatga atctaatcct caagcactga tggaagctgc atcttatatg     1920
tatgatgctg tttcagagtt tgagcagttc attaaccgtg accctgctgc actggatagc     1980
attcctaaag attctccggc tattgagtta ctcaaccgtt atacgaatct gacagctaat     2040
attcagaaca caccaaaagt aattggtgca ctgaatgtta ttaatcgaat gattaatgaa     2100
tctgctcaga atggttcttt gaatgtgact gaagaatcca gtccacagga aatgcagaac     2160
gtagcattag ctgctgaagt agcccctgaa aagctcaatc cagatctgt aaatgttgtt      2220 cttaaacatg ctgctgatgg tcgtattaaa ctgaataatc gccagattgc tgccctccag     2280
aatgctgctg caatcctgaa gggggcacgg gaatatgatg cagaagctgc ccgtcttgga     2340
ttacgtcctc aagacattgt gagtaaacag attaaaacgg atgagagcag aactcaggaa     2400
ggacaatact ctgcgttgca acatgcgaat aggattcggt ctgcgtataa ctctggtaat     2460
ttcgagttgg cctccgctta cctgaacgac tttatgcagt tcgcccagca catgcagaat     2520
aaggttggag cgttgaatga gcatcttgtt acggggaatg cggataagaa taagtctgtc     2580
cactaccaag ctcttactgc tgacagagaa tgggttcgta gccgtaccgg attggggtc     2640 aatccctatg acactaagtc ggttaaattt gcccagcaag ttgctcttga agcgaaaacg     2700
gtagcggata ttgctaatgc cctcgcttcg gcttacccgg aactgaaggt cagtcatata     2760
aaagttactc cattggattc acgtcttaac gctcctgctg ctgaggtggt caaggcattc     2820
cgtcaaggca atcgagacgt tgcttcttct caaccgaaag ctgactccgt gaatcaggtt     2880
aaagaaactc ctgttacaaa acaggaacca gttacatcta ctgtacagac taagactcct     2940
```

```
gttagtgaat ctgttaaaac agaacctact actaaagagt ctagcccaca ggctataaaa    3000
gaacctgtga accagtctga aaaacaggat gttaacctta ctaatgagga caacatcaag    3060
caacctactg aatctgttaa agaaactgaa acttctacaa aagaaagtac agttacagaa    3120
gaattaaaag aaggtattga tgctgtttac ccttcattgg taggtactgc tgattctaaa    3180
gcagagggta ttaagaacta tttcaaattg tcctttacct taccagaaga acagaaatcc    3240
cgtactgttg gttcagaagc acctctaaaa gatgtagccc aagctctgtc ttctcgtgct    3300
cgttatgaac tctttactga gaaagaaact gctaaccctg cttttaatgg ggaagttatt    3360
aagcgataca aagaactcat ggaacatggg gaaggtattg ctgatattct tcgctcccgt    3420
ctggctaagt tccttaacac taaggatgtt ggtaaacgtt ttgctcaagg tacagaagcc    3480
aaccgttggg taggtggtaa gttacttaac attgttgagc aggatgggga tacctttaag    3540
tacaacgaac aattgctaca gactgctgta ttagcaggtc ttcaatggag acttactgct    3600
accagcaata ctgctatcaa agatgcaaaa gatgttgctg ctattactgg tattgaccaa    3660
gctctgctgc cagaaggttt agtagagcaa tttgatactg gtatgacact cactgaagca    3720
gttagttccc tggctcagaa aattgagtct tactggggat tatctcgtaa tccaaatgct    3780
ccattgggct ataccaaagg catccctaca gcaatggctg ctgaaattct ggctgcattt    3840
gtagagtcta ctgatgttgt agagaacatc gtggatatgt cagaaattga cccagataac    3900
aagaagacta ttggtctgta caccattact gaactggatt ccttcgaccc aattaatagc    3960
ttccctactg ctattgaaga agctgtttta gtgaatccta cagagaagat gttctttggt    4020
gatgacattc ctcctgtagc taatactcag cttcgtaacc ctgctgttcg taatactcca    4080
gaacagaagg ctgcattgaa agcagagcag gctacagagt tctatgtaca caccccaatg    4140
gttcaattct atgagacgtt aggtaaagac cgtattctcg aactgatggg tgctggtact    4200
ctgaataaag agttacttaa tgataaccat gctaaatctc tggaaggtaa gaaccgttca    4260
gtagaggact cttacaacca actgttctcc gtcattgagc aggtaagagc acagagcgaa    4320
gacatctcta ctgtacctat tcactatgca tacaatatga cccgtgttgg tcgtatgcag    4380
atgttaggta aatacaatcc tcaatcagcc aaactggttc gtgaggccat cttacctact    4440
aaagctactt tggattttatc gaaccagaac aatgaagact tctctgcatt ccagttaggt    4500
ctggctcagg cattggacat taaagtccat actatgactc gtgaggttat gtctgacgag    4560
ttgactaaat tactgaagg taatctgaaa ccagccattg atatgatggt tgagtttaat    4620
accactggtt ccttaccaga aaacgcagtt gatgttctga atacagcatt aggagatagg    4680
aagtcattcg tagcattgat ggctcttatg gagtattccc gttacttagt agcagaggat    4740
aaatctgcat ttgtaactcc actgtatgta gaagcagatg gtgttactaa tggtccaatc    4800
aatgccatga tgctaatgac aggcggtctg tttactcctg actggattcg taatattgcc    4860 aaaggggggct tgttcattgg ttctccaaat aagaccatga atgagcatcg ctctactgct    4920
gacaataatg atttatatca agcatccact aatgctttga tggaatcgtt gggtaagtta    4980
cgtagtaact atgcctctaa tatgcctatt cagtctcaga tagacagtct tctttctctg    5040
atggatttgt tttaccgga tattaatctt ggtgagaatg gtgctttaga acttaaacgt    5100
ggtattgcta agaacccact gactattacc atctatggtt ctggtgctcg tggtattgca    5160
ggtaagctgg ttagttctgt tactgatgcc atctatgagc gtatgtctga tgtactgaaa    5220
gctcgtgcta aagacccaaa tatctctgct gctatggcaa tgtttggtaa gcaagctgct    5280
```

```
tcagaagcac atgctgaaga acttcttgcc cgtttcctga aagatatgga aacactgact    5340
tctactgttc ctgttaaacg taaaggtgta ctggaactac aatccacagg tacaggagcc    5400
aaaggaaaaa tcaatcctaa gacctatacc attaagggcg agcaactgaa ggcacttcag    5460
gaaaatatgc tgcacttctt tgtagaacca ctacgtaatg gtattactca gactgtaggt    5520
gaaagtctgg tgtactctac tgaacaatta cagaaagcta ctcagattca atctgtagtg    5580
ctggaagata tgttcaaaca gcgagtacaa gagaagctgg cagagaaggc taaagaccca    5640
acatggaaga aaggtgattt ccttactcag aaagaactga atgatattca ggcttctctg    5700
aataacttag cccctatgat tgagactggt tctcagactt tctacattgc tggttcagaa    5760
aatgcagaag tagcaaatca ggtattagct actaaccttg atgaccgtat gcgtgtacca    5820
atgagtatct atgctccagc acaggccggt gtagcaggta ttccatttat gactattggt    5880
actggtgatg gcatgatgat gcaaactctt ccactatga aggtgcacc aaagaatacc     5940
ctcaaaatct tgatggtat gaacattggt ttgaatgaca tcactgatgc cagtcgtaaa     6000
gctaatgaag ctgtttacac ttcttggcag ggtaaccta ttaagaatgt ttatgaatca     6060
tatgctaagt tcatgaagaa tgtagatttc agcaagctgt cccctgaagc attggaagca    6120
attggtaaat ctgctctgga atatgaccaa cgtgagaatg ctactgtaga tgatattgct    6180
aacgctgcat ctctgattga acgtaactta cgtaatattg cactgggtgt agatattcgt    6240
cataaggtgc tggataaggt aaatctgtcc attgaccaga tggctgctgt aggtgctcct    6300
tatcagaaca cggtaagat tgacctcagc aatatgaccc tgaacaaca ggctgatgaa      6360
ctgaataaac ttttccgtga agagttagaa gcccgtaaac aaaaagtcgc taaggctagg    6420
gctgaagtca agaagaaac tgtttctgaa aagaaccag tgaatccaga ctttggtatg     6480
gtaggccgtg agcataaggc atctggtgtt cgtatcctgt ctgctactgc tattcgtaat    6540
ctggctaaga ttagtaatct gccatctact caggcagcta ctcttgcgga gattcagaaa    6600
tcactggcag ctaaagacta taagattatc tacggtacac ctactcaggt tgcagagtat    6660
gctcgtcaga agaatgttac tgaattgact tctcaggaaa tggaagaagc tcaggcaggt    6720
aatatttatg gctggactaa cttcgatgat aagaccattt atctggttag cccatctatg    6780
gaaaccctca ttcatgaact ggttcatgcc tctaccttcg aggaagtta ttccttctat     6840
cagggtaatg aagtaagccc tacttctaag caggctattg agaaccttga aggtctgatg    6900
gaacagttcc gttctctgga tatttccaaa gattctccag aaatgagaga agcatatgct    6960
gatgctattg caactatcga aggtcatttg agtaatggat ttgttgaccc agctatctct    7020
aaagctgctg ctcttaatga gtttatggct tgggggttag ctaaccgtgc tcttgctgct    7080
aaacagaaga gaacatcttc actggttcaa atggtgaaag atgtttatca ggctattaag    7140
aaattgattt ggggacgtaa acaagctcct gcattgggag aagatatgtt ctccaatctg    7200
ctgtttaact ctgcaattct gatgcgtagc caacctacaa ctcaggcagt agctaaagat    7260
ggcacactgt tccatagcaa agcatatggt aataatgaac gtctgtctca gttgaaccag    7320
actttcgata aactggtaac tgattaccct cgtactgacc cagttacaga agtagaacgt    7380
cgtggcaatg tggctaatgc attaatgagt gctactcgac tggttcgtga tgttcagtct    7440
catggcttca atatgactgc tcaggaacag tctgtattcc agatggttac tgctgcatta    7500
gcaactgaag ctgcgattga cccacatgct atggctcgtg ctcaggaact ttatacccat    7560
gtaatgaaac accttacggt agagcatttc atggctgacc ctgatagtac taaccctgct    7620
gaccgttact atgctcaaca gaaatatgac accatctctg gtgctaatct ggttgaagta    7680
```

```
gatgccaaag gtagaaccag tctgttacct acattcctgg gtctggctat ggttaatgaa    7740
gaactacgtt caatcattaa agaaatgcct gtacctaaag cagataagaa attagggaat    7800
gatatagata ctctgcttac caatgcaggt actcaggtaa tggaatctct gaaccgtcgt    7860
atggctggtg accagaaagc tactaatgtt caggacagta ttgatgcttt gtcagaaaca    7920
atcatgctg ctgctttgaa acgagagtcc ttctatgatg ctgtagcaac ccctaccggt    7980
aacttcattg accgtgctaa tcagtacgta acggatagca ttgaacggtt atctgaaact    8040
gttattgaga aggcagataa ggtaattgct aacccttcta atatagctgc taaaggtgtt    8100
gctcatctgg ctaaactgac tgctgctatt gcatctgaaa acagggtga atagtggct    8160
cagggtgtta tgactgctat gaaccagggt aaagtatggc aacctttcca tgacttagtt    8220
aatgacattg ttggccgtac taagactaat gccaatgtct atgacttaat caaattggtt    8280
aagagccaga tttctcaaga ccgtcagcaa ttccgtgagc atttacctac agtcattgct    8340
ggtaagttct ctcgtaaatt gactgatacc gaatggtctg caatgcatac tggtttaggt    8400
aaaacagatt tagctgttct acgtgaaact atgagcatgg ctgaaattag agatttactc    8460
tcttcatcca agaaagtgaa agatgaaatc tctactctgg aaaagagat tcagaaccaa    8520
gcaggtagaa actggaatct ggttcagaag aaatctaagc aactggctca atacatgatt    8580
atggggaag taggtaataa cctccttcgt aatgcccatg ctattagtcg tttgttaggt    8640
gaacgtatta ctaatggtcc tgtggcagat gtagctgcta ttgataagct cattactttg    8700
tactctctgg aattgatgaa taagtctgac cgtgacctt tgtcagaatt ggctcaatca    8760
gaagtggaag gtatggagtt ctccattgct tatatggttg gtcaacgtac tgaagagatg    8820
cgtaaagcta aaggtgataa ccgtactctg ctgaatcact ttaaaggcta tatccctgta    8880
gagaaccagc aaggtgtgaa tttgattatt gctgacgata agagtttgc taagttaaat    8940
agccaatcct ttactcgtat tggtacttat caggggagca ctggtttccg tactggttct    9000
aaaggttatt acttcagccc agtagctgcc cgtgcccctt actctcaggg tattcttcag    9060
aacgttcgta atactgctgg tggtgtggat attggtactg gctttacgtt aggcactatg    9120
gttgctgggc gtattactga caaaccaacc gtagagcgta ttaccaaagc tctggctaaa    9180
ggtgagcgtg ggcgtgaacc actgatgcca atttataaca gcaaaggtca ggtagttgct    9240
tatgaacaat ccgttgaccc taatatgttg aagcacctaa accaagacaa tcactttgct    9300
aagatggttg gtgtatggcg tggtcgtcag gtggaagagg ctaaagcaca acgttttaat    9360
gacattctca ttgagcaatt acatgctatg tatgagaaag acattaaaga ctccagtgct    9420
aataaatctc aatatgtaaa cctgttaggt aaaattgatg acccagtact ggctgatgcg    9480
attaacctga tgaacattga actcgtcat aaggccgaag aactcttcgg taaagatgag    9540
ttatgggttc gtagggatat gctgaatgat gcacttggct atcgtgctgc atctattggt    9600
gatgtgtgga ccggtaactc tcgttggtca cctagcaccc ttgatactgt taagaagatg    9660
ttcctcggtg cattcggtaa taaggcatat catgtagtaa tgaatgctga aaataccatt    9720
cagaacttag tgaaggacgc taagacagta attgttgtta aatctgttgt agtaccggca    9780
gttaacttcc ttgctaacat ctaccagatg attggacgtg gtgttcctgt taagatatt    9840
gctgtgaaca ttcctcgtaa gacgtcagag attaatcagt atattaaatc tcgtttacgt    9900
cagattgatg cggaagcaga gctacgtgct gctgaaggta accctaatct ggttcgtaaa    9960
cttaaaactg agattcaatc tattactgat agtcatcgtc gtatgagtat ctggcctttg   10020
```

-continued

```
attgaagcag gtgagttctc ttctattgct gatgctggta ttagtcgtga tgacctgtta    10080
gtagctgaag gtaagattca tgagtacatg gaaaaacttg ctaataaact tccagaaaaa    10140
gtacgtaatg ctggccgtta cgctcttatt gctaaggaca ctgctctgtt ccagggtatc    10200
cagaaaacag tagagtattc agactttatt gctaaagcca tcatctatga tgatttagtg    10260
aaacgtaaga aaaatcttc ttctgaagca ttaggtcagg taactgaaga gtttattaac    10320
tatgacagat tgcctggtcg tttccgtggc tatatggaaa gtatgggtct gatgtggttc    10380
tacaacttta aaattcgttc cattaaagtt gctatgagca tgattagaaa caacccagta    10440
cattctctga ttgctacagt agtacctgct cctaccatgt ttggtaacgt aggtctacca    10500
attcaggaca acatgctaac catgctggct gaaggaagac tggattactc attaggcttc    10560
ggacaaggat taagagcacc taccctcaat ccttggttca accttactca ctaataa       10617
```

<210> SEQ ID NO 15
<211> LENGTH: 3537
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 15

```
Met Gly Gly Ser His His His His His Gly Met Ala Ser Met Thr
  1               5                  10                  15

Gly Gly Gln Gln Met Gly Arg Asp Leu Tyr Asp Asp Asp Lys Asp
                 20                  25                  30

Pro Ser Ser Arg Ser Met Ser Val Phe Asp Arg Leu Ala Gly Phe Ala
                 35                  40                  45

Asp Ser Val Thr Asn Ala Lys Gln Val Asp Val Ser Thr Ala Thr Ala
         50                  55                  60

Gln Lys Lys Ala Glu Gln Gly Val Thr Thr Pro Leu Val Ser Pro Asp
 65                  70                  75                  80

Ala Ala Tyr Gln Met Gln Ala Ala Arg Thr Gly Asn Val Gly Ala Asn
                 85                  90                  95

Ala Phe Glu Pro Gly Thr Val Gln Ser Asp Phe Met Asn Leu Thr Pro
                100                 105                 110

Met Gln Ile Met Asn Lys Tyr Gly Val Glu Gly Leu Gln Leu Ile
            115                 120                 125

Asn Ala Arg Ala Asp Ala Gly Asn Gln Val Phe Asn Asp Ser Val Thr
        130                 135                 140

Thr Arg Thr Pro Gly Glu Glu Leu Gly Asp Ile Ala Thr Gly Val Gly
145                 150                 155                 160

Leu Gly Phe Val Asn Thr Leu Gly Gly Ile Gly Ala Leu Gly Ala Gly
                165                 170                 175

Leu Leu Asn Asp Asp Ala Gly Ala Val Val Ala Gln Gln Leu Ser Lys
                180                 185                 190

Phe Asn Asp Ala Val His Ala Thr Gln Ser Gln Ala Leu Gln Asp Lys
            195                 200                 205

Arg Lys Leu Phe Ala Ala Arg Asn Leu Met Asn Glu Val Glu Ser Glu
    210                 215                 220

Arg Gln Tyr Gln Thr Asp Lys Lys Glu Gly Thr Asn Asp Ile Val Ala
225                 230                 235                 240

Ser Leu Ser Lys Phe Gly Arg Asp Phe Val Gly Ser Ile Glu Asn Ala
                245                 250                 255
```

```
Ala Gln Thr Asp Ser Ile Ile Ser Asp Gly Leu Ala Glu Gly Val Gly
            260                 265                 270

Ser Leu Leu Gly Ala Gly Pro Val Arg Gly Ala Ser Leu Leu Gly
        275                 280                 285

Lys Ala Val Val Pro Ala Asn Thr Leu Arg Ser Ala Ala Leu Ala Gly
            290                 295                 300

Ala Ile Asp Ala Gly Thr Gly Thr Gln Ser Leu Ala Arg Ile Ala Ser
305                 310                 315                 320

Thr Val Gly Arg Ala Ala Pro Gly Met Val Gly Val Gly Ala Met Glu
                325                 330                 335

Ala Gly Gly Ala Tyr Gln Gln Thr Ala Asp Glu Ile Met Lys Met Ser
                340                 345                 350

Leu Lys Asp Leu Glu Lys Ser Pro Val Tyr Gln Gln His Ile Lys Asp
            355                 360                 365

Gly Met Ser Pro Glu Gln Ala Arg Arg Gln Thr Ala Ser Glu Thr Gly
            370                 375                 380

Leu Thr Ala Ala Ala Ile Gln Leu Pro Ile Ala Ala Thr Gly Pro
385                 390                 395                 400

Leu Val Ser Arg Phe Glu Met Ala Pro Phe Arg Ala Gly Ser Leu Gly
                405                 410                 415

Ala Val Gly Met Asn Leu Ala Arg Glu Thr Val Glu Glu Gly Val Gln
                420                 425                 430

Gly Ala Thr Gly Gln Leu Ala Gln Asn Ile Ala Gln Gln Asn Ile
            435                 440                 445

Asp Lys Asn Gln Asp Leu Leu Lys Gly Val Gly Thr Gln Ala Gly Leu
            450                 455                 460

Gly Ala Leu Tyr Gly Phe Gly Ser Ala Gly Val Val Gln Ala Pro Ala
465                 470                 475                 480

Gly Ala Ala Arg Leu Ala Gly Ala Ala Thr Ala Pro Val Leu Arg Thr
                485                 490                 495

Thr Met Ala Gly Val Lys Ala Ala Gly Ser Val Ala Gly Lys Val Val
            500                 505                 510

Ser Pro Ile Lys Asn Thr Leu Val Ala Arg Gly Glu Arg Val Met Lys
            515                 520                 525

Gln Asn Glu Glu Ala Ser Pro Val Ala Asp Asp Tyr Val Ala Gln Ala
            530                 535                 540

Ala Gln Glu Ala Met Ala Gln Ala Pro Glu Ala Glu Val Thr Ile Arg
545                 550                 555                 560

Asp Ala Val Glu Ala Thr Asp Ala Thr Pro Glu Gln Lys Val Ala Ala
                565                 570                 575

His Gln Tyr Val Ser Asp Leu Met Asn Ala Thr Arg Phe Asn Pro Glu
            580                 585                 590

Asn Tyr Gln Glu Ala Pro Glu His Ile Arg Asn Ala Val Ala Gly Ser
            595                 600                 605

Thr Asp Gln Val Gln Val Ile Gln Lys Leu Ala Asp Leu Val Asn Thr
            610                 615                 620

Leu Asp Glu Ser Asn Pro Gln Ala Leu Met Glu Ala Ser Tyr Met
625                 630                 635                 640

Tyr Asp Ala Val Ser Glu Phe Glu Gln Phe Ile Asn Arg Asp Pro Ala
                645                 650                 655

Ala Leu Asp Ser Ile Pro Lys Asp Ser Pro Ala Ile Glu Leu Leu Asn
                660                 665                 670

Arg Tyr Thr Asn Leu Thr Ala Asn Ile Gln Asn Thr Pro Lys Val Ile
```

-continued

```
                675                 680                 685
Gly Ala Leu Asn Val Ile Asn Arg Met Ile Asn Glu Ser Ala Gln Asn
            690                 695                 700
Gly Ser Leu Asn Val Thr Glu Glu Ser Ser Pro Gln Glu Met Gln Asn
705                 710                 715                 720
Val Ala Leu Ala Ala Glu Val Ala Pro Glu Lys Leu Asn Pro Glu Ser
                725                 730                 735
Val Asn Val Val Leu Lys His Ala Ala Asp Gly Arg Ile Lys Leu Asn
                740                 745                 750
Asn Arg Gln Ile Ala Ala Leu Gln Asn Ala Ala Ile Leu Lys Gly
                755                 760                 765
Ala Arg Glu Tyr Asp Ala Glu Ala Ala Arg Leu Gly Leu Arg Pro Gln
        770                 775                 780
Asp Ile Val Ser Lys Gln Ile Lys Thr Asp Glu Ser Arg Thr Gln Glu
785                 790                 795                 800
Gly Gln Tyr Ser Ala Leu Gln His Ala Asn Arg Ile Arg Ser Ala Tyr
                805                 810                 815
Asn Ser Gly Asn Phe Glu Leu Ala Ser Ala Tyr Leu Asn Asp Phe Met
            820                 825                 830
Gln Phe Ala Gln His Met Gln Asn Lys Val Gly Ala Leu Asn Glu His
        835                 840                 845
Leu Val Thr Gly Asn Ala Asp Lys Asn Lys Ser Val His Tyr Gln Ala
    850                 855                 860
Leu Thr Ala Asp Arg Glu Trp Val Arg Ser Arg Thr Gly Leu Gly Val
865                 870                 875                 880
Asn Pro Tyr Asp Thr Lys Ser Val Lys Phe Ala Gln Gln Val Ala Leu
                885                 890                 895
Glu Ala Lys Thr Val Ala Asp Ile Ala Asn Ala Leu Ala Ser Ala Tyr
                900                 905                 910
Pro Glu Leu Lys Val Ser His Ile Lys Val Thr Pro Leu Asp Ser Arg
            915                 920                 925
Leu Asn Ala Pro Ala Ala Glu Val Val Lys Ala Phe Arg Gln Gly Asn
    930                 935                 940
Arg Asp Val Ala Ser Ser Gln Pro Lys Ala Asp Ser Val Asn Gln Val
945                 950                 955                 960
Lys Glu Thr Pro Val Thr Lys Gln Glu Pro Val Thr Ser Thr Val Gln
                965                 970                 975
Thr Lys Thr Pro Val Ser Glu Ser Val Lys Thr Glu Pro Thr Thr Lys
            980                 985                 990
Glu Ser Ser Pro Gln Ala Ile Lys Glu Pro Val Asn Gln Ser Glu Lys
            995                 1000                1005
Gln Asp Val Asn Leu Thr Asn Glu Asp Asn Ile Lys Gln Pro Thr Glu
    1010                1015                1020
Ser Val Lys Glu Thr Glu Thr Ser Thr Lys Glu Ser Thr Val Thr Glu
1025                1030                1035                1040
Glu Leu Lys Glu Gly Ile Asp Ala Val Tyr Pro Ser Leu Val Gly Thr
                1045                1050                1055
Ala Asp Ser Lys Ala Glu Gly Ile Lys Asn Tyr Phe Lys Leu Ser Phe
                1060                1065                1070
Thr Leu Pro Glu Glu Gln Lys Ser Arg Thr Val Gly Ser Glu Ala Pro
        1075                1080                1085
Leu Lys Asp Val Ala Gln Ala Leu Ser Ser Arg Ala Arg Tyr Glu Leu
    1090                1095                1100
```

```
Phe Thr Glu Lys Glu Thr Ala Asn Pro Ala Phe Asn Gly Glu Val Ile
1105                1110                1115                1120

Lys Arg Tyr Lys Glu Leu Met Glu His Gly Glu Gly Ile Ala Asp Ile
            1125                1130                1135

Leu Arg Ser Arg Leu Ala Lys Phe Leu Asn Thr Lys Asp Val Gly Lys
        1140                1145                1150

Arg Phe Ala Gln Gly Thr Glu Ala Asn Arg Trp Val Gly Gly Lys Leu
    1155                1160                1165

Leu Asn Ile Val Glu Gln Asp Gly Asp Thr Phe Lys Tyr Asn Glu Gln
1170                1175                1180

Leu Leu Gln Thr Ala Val Leu Ala Gly Leu Gln Trp Arg Leu Thr Ala
1185                1190                1195                1200

Thr Ser Asn Thr Ala Ile Lys Asp Ala Lys Asp Val Ala Ala Ile Thr
            1205                1210                1215

Gly Ile Asp Gln Ala Leu Leu Pro Glu Gly Leu Val Glu Gln Phe Asp
        1220                1225                1230

Thr Gly Met Thr Leu Thr Glu Ala Val Ser Ser Leu Ala Gln Lys Ile
    1235                1240                1245

Glu Ser Tyr Trp Gly Leu Ser Arg Asn Pro Asn Ala Pro Leu Gly Tyr
1250                1255                1260

Thr Lys Gly Ile Pro Thr Ala Met Ala Ala Glu Ile Leu Ala Ala Phe
1265                1270                1275                1280

Val Glu Ser Thr Asp Val Val Glu Asn Ile Val Asp Met Ser Glu Ile
            1285                1290                1295

Asp Pro Asp Asn Lys Lys Thr Ile Gly Leu Tyr Thr Ile Thr Glu Leu
        1300                1305                1310

Asp Ser Phe Asp Pro Ile Asn Ser Phe Pro Thr Ala Ile Glu Glu Ala
    1315                1320                1325

Val Leu Val Asn Pro Thr Glu Lys Met Phe Phe Gly Asp Asp Ile Pro
1330                1335                1340

Pro Val Ala Asn Thr Gln Leu Arg Asn Pro Ala Val Arg Asn Thr Pro
1345                1350                1355                1360

Glu Gln Lys Ala Ala Leu Lys Ala Glu Gln Ala Thr Glu Phe Tyr Val
            1365                1370                1375

His Thr Pro Met Val Gln Phe Tyr Glu Thr Leu Gly Lys Asp Arg Ile
        1380                1385                1390

Leu Glu Leu Met Gly Ala Gly Thr Leu Asn Lys Glu Leu Leu Asn Asp
    1395                1400                1405

Asn His Ala Lys Ser Leu Glu Gly Lys Asn Arg Ser Val Glu Asp Ser
1410                1415                1420

Tyr Asn Gln Leu Phe Ser Val Ile Glu Gln Val Arg Ala Gln Ser Glu
1425                1430                1435                1440

Asp Ile Ser Thr Val Pro Ile His Tyr Ala Tyr Asn Met Thr Arg Val
            1445                1450                1455

Gly Arg Met Gln Met Leu Gly Lys Tyr Asn Pro Gln Ser Ala Lys Leu
        1460                1465                1470

Val Arg Glu Ala Ile Leu Pro Thr Lys Ala Thr Leu Asp Leu Ser Asn
    1475                1480                1485

Gln Asn Asn Glu Asp Phe Ser Ala Phe Gln Leu Gly Leu Ala Gln Ala
1490                1495                1500

Leu Asp Ile Lys Val His Thr Met Thr Arg Glu Val Met Ser Asp Glu
1505                1510                1515                1520
```

-continued

```
Leu Thr Lys Leu Leu Glu Gly Asn Leu Lys Pro Ala Ile Asp Met Met
            1525                1530                1535

Val Glu Phe Asn Thr Thr Gly Ser Leu Pro Glu Asn Ala Val Asp Val
        1540                1545                1550

Leu Asn Thr Ala Leu Gly Asp Arg Lys Ser Phe Val Ala Leu Met Ala
    1555                1560                1565

Leu Met Glu Tyr Ser Arg Tyr Leu Val Ala Glu Asp Lys Ser Ala Phe
1570                1575                1580

Val Thr Pro Leu Tyr Val Glu Ala Asp Gly Val Thr Asn Gly Pro Ile
1585                1590                1595                1600

Asn Ala Met Met Leu Met Thr Gly Gly Leu Phe Thr Pro Asp Trp Ile
            1605                1610                1615

Arg Asn Ile Ala Lys Gly Gly Leu Phe Ile Gly Ser Pro Asn Lys Thr
        1620                1625                1630

Met Asn Glu His Arg Ser Thr Ala Asp Asn Asn Asp Leu Tyr Gln Ala
    1635                1640                1645

Ser Thr Asn Ala Leu Met Glu Ser Leu Gly Lys Leu Arg Ser Asn Tyr
1650                1655                1660

Ala Ser Asn Met Pro Ile Gln Ser Gln Ile Asp Ser Leu Leu Ser Leu
1665                1670                1675                1680

Met Asp Leu Phe Leu Pro Asp Ile Asn Leu Gly Glu Asn Gly Ala Leu
            1685                1690                1695

Glu Leu Lys Arg Gly Ile Ala Lys Asn Pro Leu Thr Ile Thr Ile Tyr
        1700                1705                1710

Gly Ser Gly Ala Arg Gly Ile Ala Gly Lys Leu Val Ser Ser Val Thr
    1715                1720                1725

Asp Ala Ile Tyr Glu Arg Met Ser Asp Val Leu Lys Ala Arg Ala Lys
1730                1735                1740

Asp Pro Asn Ile Ser Ala Ala Met Ala Met Phe Gly Lys Gln Ala Ala
1745                1750                1755                1760

Ser Glu Ala His Ala Glu Glu Leu Leu Ala Arg Phe Leu Lys Asp Met
            1765                1770                1775

Glu Thr Leu Thr Ser Thr Val Pro Val Lys Arg Lys Gly Val Leu Glu
        1780                1785                1790

Leu Gln Ser Thr Gly Thr Gly Ala Lys Gly Lys Ile Asn Pro Lys Thr
    1795                1800                1805

Tyr Thr Ile Lys Gly Glu Gln Leu Lys Ala Leu Gln Glu Asn Met Leu
1810                1815                1820

His Phe Phe Val Glu Pro Leu Arg Asn Gly Ile Thr Gln Thr Val Gly
1825                1830                1835                1840

Glu Ser Leu Val Tyr Ser Thr Glu Gln Leu Gln Lys Ala Thr Gln Ile
            1845                1850                1855

Gln Ser Val Val Leu Glu Asp Met Phe Lys Gln Arg Val Gln Glu Lys
        1860                1865                1870

Leu Ala Glu Lys Ala Lys Asp Pro Thr Trp Lys Lys Gly Asp Phe Leu
    1875                1880                1885

Thr Gln Lys Glu Leu Asn Asp Ile Gln Ala Ser Leu Asn Asn Leu Ala
1890                1895                1900

Pro Met Ile Glu Thr Gly Ser Gln Thr Phe Tyr Ile Ala Gly Ser Glu
1905                1910                1915                1920

Asn Ala Glu Val Ala Asn Gln Val Leu Ala Thr Asn Leu Asp Asp Arg
            1925                1930                1935

Met Arg Val Pro Met Ser Ile Tyr Ala Pro Ala Gln Ala Gly Val Ala
```

-continued

```
                1940                1945                1950
Gly Ile Pro Phe Met Thr Ile Gly Thr Gly Asp Gly Met Met Met Gln
       1955                1960                1965
Thr Leu Ser Thr Met Lys Gly Ala Pro Lys Asn Thr Leu Lys Ile Phe
       1970                1975                1980
Asp Gly Met Asn Ile Gly Leu Asn Asp Ile Thr Asp Ala Ser Arg Lys
1985                1990                1995                2000
Ala Asn Glu Ala Val Tyr Thr Ser Trp Gln Gly Asn Pro Ile Lys Asn
            2005                2010                2015
Val Tyr Glu Ser Tyr Ala Lys Phe Met Lys Asn Val Asp Phe Ser Lys
         2020                2025                2030
Leu Ser Pro Glu Ala Leu Glu Ala Ile Gly Lys Ser Ala Leu Glu Tyr
       2035                2040                2045
Asp Gln Arg Glu Asn Ala Thr Val Asp Ile Ala Asn Ala Ala Ser
    2050                2055                2060
Leu Ile Glu Arg Asn Leu Arg Asn Ile Ala Leu Gly Val Asp Ile Arg
2065                2070                2075                2080
His Lys Val Leu Asp Lys Val Asn Leu Ser Ile Asp Gln Met Ala Ala
            2085                2090                2095
Val Gly Ala Pro Tyr Gln Asn Asn Gly Lys Ile Asp Leu Ser Asn Met
         2100                2105                2110
Thr Pro Glu Gln Gln Ala Asp Glu Leu Asn Lys Leu Phe Arg Glu Glu
       2115                2120                2125
Leu Glu Ala Arg Lys Gln Lys Val Ala Lys Ala Arg Ala Glu Val Lys
       2130                2135                2140
Glu Glu Thr Val Ser Glu Lys Glu Pro Val Asn Pro Asp Phe Gly Met
2145                2150                2155                2160
Val Gly Arg Glu His Lys Ala Ser Gly Val Arg Ile Leu Ser Ala Thr
            2165                2170                2175
Ala Ile Arg Asn Leu Ala Lys Ile Ser Asn Leu Pro Ser Thr Gln Ala
         2180                2185                2190
Ala Thr Leu Ala Glu Ile Gln Lys Ser Leu Ala Ala Lys Asp Tyr Lys
       2195                2200                2205
Ile Ile Tyr Gly Thr Pro Thr Gln Val Ala Glu Tyr Ala Arg Gln Lys
       2210                2215                2220
Asn Val Thr Glu Leu Thr Ser Gln Glu Met Glu Glu Ala Gln Ala Gly
2225                2230                2235                2240
Asn Ile Tyr Gly Trp Thr Asn Phe Asp Asp Lys Thr Ile Tyr Leu Val
            2245                2250                2255
Ser Pro Ser Met Glu Thr Leu Ile His Glu Leu Val His Ala Ser Thr
         2260                2265                2270
Phe Glu Glu Val Tyr Ser Phe Tyr Gln Gly Asn Glu Val Ser Pro Thr
       2275                2280                2285
Ser Lys Gln Ala Ile Glu Asn Leu Glu Gly Leu Met Glu Gln Phe Arg
       2290                2295                2300
Ser Leu Asp Ile Ser Lys Asp Ser Pro Glu Met Arg Glu Ala Tyr Ala
2305                2310                2315                2320
Asp Ala Ile Ala Thr Ile Glu Gly His Leu Ser Asn Gly Phe Val Asp
            2325                2330                2335
Pro Ala Ile Ser Lys Ala Ala Ala Leu Asn Glu Phe Met Ala Trp Gly
         2340                2345                2350
Leu Ala Asn Arg Ala Leu Ala Ala Lys Gln Lys Arg Thr Ser Ser Leu
       2355                2360                2365
```

```
Val Gln Met Val Lys Asp Val Tyr Gln Ala Ile Lys Lys Leu Ile Trp
    2370            2375                2380

Gly Arg Lys Gln Ala Pro Ala Leu Gly Glu Asp Met Phe Ser Asn Leu
2385            2390                2395                2400

Leu Phe Asn Ser Ala Ile Leu Met Arg Ser Gln Pro Thr Thr Gln Ala
            2405                2410                2415

Val Ala Lys Asp Gly Thr Leu Phe His Ser Lys Ala Tyr Gly Asn Asn
            2420                2425                2430

Glu Arg Leu Ser Gln Leu Asn Gln Thr Phe Asp Lys Leu Val Thr Asp
            2435                2440                2445

Tyr Leu Arg Thr Asp Pro Val Thr Glu Val Glu Arg Arg Gly Asn Val
            2450                2455                2460

Ala Asn Ala Leu Met Ser Ala Thr Arg Leu Val Arg Asp Val Gln Ser
2465            2470                2475                2480

His Gly Phe Asn Met Thr Ala Gln Glu Gln Ser Val Phe Gln Met Val
            2485                2490                2495

Thr Ala Ala Leu Ala Thr Glu Ala Ala Ile Asp Pro His Ala Met Ala
            2500                2505                2510

Arg Ala Gln Glu Leu Tyr Thr His Val Met Lys His Leu Thr Val Glu
            2515                2520                2525

His Phe Met Ala Asp Pro Asp Ser Thr Asn Pro Ala Asp Arg Tyr Tyr
            2530                2535                2540

Ala Gln Gln Lys Tyr Asp Thr Ile Ser Gly Ala Asn Leu Val Glu Val
2545            2550                2555                2560

Asp Ala Lys Gly Arg Thr Ser Leu Leu Pro Thr Phe Leu Gly Leu Ala
            2565                2570                2575

Met Val Asn Glu Glu Leu Arg Ser Ile Ile Lys Glu Met Pro Val Pro
            2580                2585                2590

Lys Ala Asp Lys Lys Leu Gly Asn Asp Ile Asp Thr Leu Leu Thr Asn
            2595                2600                2605

Ala Gly Thr Gln Val Met Glu Ser Leu Asn Arg Arg Met Ala Gly Asp
    2610                2615                2620

Gln Lys Ala Thr Asn Val Gln Asp Ser Ile Asp Ala Leu Ser Glu Thr
2625            2630                2635                2640

Ile Met Ala Ala Ala Leu Lys Arg Glu Ser Phe Tyr Asp Ala Val Ala
            2645                2650                2655

Thr Pro Thr Gly Asn Phe Ile Asp Arg Ala Asn Gln Tyr Val Thr Asp
            2660                2665                2670

Ser Ile Glu Arg Leu Ser Glu Thr Val Ile Glu Lys Ala Asp Lys Val
            2675                2680                2685

Ile Ala Asn Pro Ser Asn Ile Ala Ala Lys Gly Val Ala His Leu Ala
    2690                2695                2700

Lys Leu Thr Ala Ala Ile Ala Ser Glu Lys Gln Gly Glu Ile Val Ala
2705            2710                2715                2720

Gln Gly Val Met Thr Ala Met Asn Gln Gly Lys Val Trp Gln Pro Phe
            2725                2730                2735

His Asp Leu Val Asn Asp Ile Val Gly Arg Thr Lys Thr Asn Ala Asn
            2740                2745                2750

Val Tyr Asp Leu Ile Lys Leu Val Lys Ser Gln Ile Ser Gln Asp Arg
            2755                2760                2765

Gln Gln Phe Arg Glu His Leu Pro Thr Val Ile Ala Gly Lys Phe Ser
    2770                2775                2780
```

-continued

```
Arg Lys Leu Thr Asp Thr Glu Trp Ser Ala Met His Thr Gly Leu Gly
2785                2790                2795                2800

Lys Thr Asp Leu Ala Val Leu Arg Glu Thr Met Ser Met Ala Glu Ile
            2805                2810                2815

Arg Asp Leu Leu Ser Ser Ser Lys Lys Val Lys Asp Glu Ile Ser Thr
                2820                2825                2830

Leu Glu Lys Glu Ile Gln Asn Gln Ala Gly Arg Asn Trp Asn Leu Val
            2835                2840                2845

Gln Lys Lys Ser Lys Gln Leu Ala Gln Tyr Met Ile Met Gly Glu Val
        2850                2855                2860

Gly Asn Asn Leu Leu Arg Asn Ala His Ala Ile Ser Arg Leu Leu Gly
2865                2870                2875                2880

Glu Arg Ile Thr Asn Gly Pro Val Ala Asp Val Ala Ala Ile Asp Lys
            2885                2890                2895

Leu Ile Thr Leu Tyr Ser Leu Glu Leu Met Asn Lys Ser Asp Arg Asp
            2900                2905                2910

Leu Leu Ser Glu Leu Ala Gln Ser Glu Val Glu Gly Met Glu Phe Ser
        2915                2920                2925

Ile Ala Tyr Met Val Gly Gln Arg Thr Glu Glu Met Arg Lys Ala Lys
        2930                2935                2940

Gly Asp Asn Arg Thr Leu Leu Asn His Phe Lys Gly Tyr Ile Pro Val
2945                2950                2955                2960

Glu Asn Gln Gln Gly Val Asn Leu Ile Ile Ala Asp Asp Lys Glu Phe
            2965                2970                2975

Ala Lys Leu Asn Ser Gln Ser Phe Thr Arg Ile Gly Thr Tyr Gln Gly
            2980                2985                2990

Ser Thr Gly Phe Arg Thr Gly Ser Lys Gly Tyr Tyr Phe Ser Pro Val
        2995                3000                3005

Ala Ala Arg Ala Pro Tyr Ser Gln Gly Ile Leu Gln Asn Val Arg Asn
    3010                3015                3020

Thr Ala Gly Gly Val Asp Ile Gly Thr Gly Phe Thr Leu Gly Thr Met
3025                3030                3035                3040

Val Ala Gly Arg Ile Thr Asp Lys Pro Thr Val Glu Arg Ile Thr Lys
            3045                3050                3055

Ala Leu Ala Lys Gly Glu Arg Gly Arg Glu Pro Leu Met Pro Ile Tyr
            3060                3065                3070

Asn Ser Lys Gly Gln Val Val Ala Tyr Glu Gln Ser Val Asp Pro Asn
        3075                3080                3085

Met Leu Lys His Leu Asn Gln Asp Asn His Phe Ala Lys Met Val Gly
    3090                3095                3100

Val Trp Arg Gly Arg Gln Val Glu Glu Ala Lys Ala Gln Arg Phe Asn
3105                3110                3115                3120

Asp Ile Leu Ile Glu Gln Leu His Ala Met Tyr Glu Lys Asp Ile Lys
            3125                3130                3135

Asp Ser Ser Ala Asn Lys Ser Gln Tyr Val Asn Leu Leu Gly Lys Ile
            3140                3145                3150

Asp Asp Pro Val Leu Ala Asp Ala Ile Asn Leu Met Asn Ile Glu Thr
        3155                3160                3165

Arg His Lys Ala Glu Glu Leu Phe Gly Lys Asp Glu Leu Trp Val Arg
    3170                3175                3180

Arg Asp Met Leu Asn Asp Ala Leu Gly Tyr Arg Ala Ala Ser Ile Gly
    3185                3190                3195                3200

Asp Val Trp Thr Gly Asn Ser Arg Trp Ser Pro Ser Thr Leu Asp Thr
```

```
                    3205                3210                3215

Val Lys Lys Met Phe Leu Gly Ala Phe Gly Asn Lys Ala Tyr His Val
            3220                3225                3230

Val Met Asn Ala Glu Asn Thr Ile Gln Asn Leu Val Lys Asp Ala Lys
        3235                3240                3245

Thr Val Ile Val Val Lys Ser Val Val Pro Ala Val Asn Phe Leu
    3250                3255                3260

Ala Asn Ile Tyr Gln Met Ile Gly Arg Gly Val Pro Val Lys Asp Ile
3265                3270                3275                3280

Ala Val Asn Ile Pro Arg Lys Thr Ser Glu Ile Asn Gln Tyr Ile Lys
            3285                3290                3295

Ser Arg Leu Arg Gln Ile Asp Ala Glu Ala Glu Leu Arg Ala Ala Glu
        3300                3305                3310

Gly Asn Pro Asn Leu Val Arg Lys Leu Lys Thr Glu Ile Gln Ser Ile
    3315                3320                3325

Thr Asp Ser His Arg Arg Met Ser Ile Trp Pro Leu Ile Glu Ala Gly
    3330                3335                3340

Glu Phe Ser Ser Ile Ala Asp Ala Gly Ile Ser Arg Asp Asp Leu Leu
3345                3350                3355                3360

Val Ala Glu Gly Lys Ile His Glu Tyr Met Glu Lys Leu Ala Asn Lys
            3365                3370                3375

Leu Pro Glu Lys Val Arg Asn Ala Gly Arg Tyr Ala Leu Ile Ala Lys
        3380                3385                3390

Asp Thr Ala Leu Phe Gln Gly Ile Gln Lys Thr Val Glu Tyr Ser Asp
    3395                3400                3405

Phe Ile Ala Lys Ala Ile Ile Tyr Asp Asp Leu Val Lys Arg Lys Lys
    3410                3415                3420

Lys Ser Ser Ser Glu Ala Leu Gly Gln Val Thr Glu Glu Phe Ile Asn
3425                3430                3435                3440

Tyr Asp Arg Leu Pro Gly Arg Phe Arg Gly Tyr Met Glu Ser Met Gly
            3445                3450                3455

Leu Met Trp Phe Tyr Asn Phe Lys Ile Arg Ser Ile Lys Val Ala Met
        3460                3465                3470

Ser Met Ile Arg Asn Asn Pro Val His Ser Leu Ile Ala Thr Val Val
    3475                3480                3485

Pro Ala Pro Thr Met Phe Gly Asn Val Gly Leu Pro Ile Gln Asp Asn
    3490                3495                3500

Met Leu Thr Met Leu Ala Glu Gly Arg Leu Asp Tyr Ser Leu Gly Phe
3505                3510                3515                3520

Gly Gln Gly Leu Arg Ala Pro Thr Leu Asn Pro Trp Phe Asn Leu Thr
            3525                3530                3535

His

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 16
ggcattactt catccaaaag aagcggagct tc                                  32

<210> SEQ ID NO 17
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ggccatccat tacttcatcc aaaagaagcg gagcttc                          37

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggatccaaaa gaagcggagc ttc                                         23

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ggcattactt catccaaaag aagctgagct tc                               32

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ggcattactt catccaaaag aagcggagc                                   29

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
ggaggctcct cggagtctcc tttt                                        24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
ggactacctt cgggtagtcc ttttt                                       25

<210> SEQ ID NO 23
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
agaagggggc tactaagccc tcttcttatt ttt                                    33

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
aagctgctcc gcagctttt                                                    19

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
aaggctatcc ctacgggggt agcctttatt ttttt                                  35

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
gccctccttg tgagggcttt tt                                                22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
caacgaagcg ttgaatacct                                                   20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
ttcttcgagg cgaagaaaac ct                                                22

<210> SEQ ID NO 29
<211> LENGTH: 20
<212> TYPE: DNA
```

-continued

```
<213> ORGANISM: Artificial Sequence
<220> FEATURE:
<223> OTHER INFORMATION: Description of Artificial Sequence:  Synthetic
      Primer

<400> SEQUENCE: 29
cgacgaggcg tcgaaaacca                                                       20
```